US012512190B2

(12) United States Patent
Ashmore et al.

(10) Patent No.: US 12,512,190 B2
(45) Date of Patent: Dec. 30, 2025

(54) SYSTEMS AND METHODS FOR DOCUMENTING EMERGENCY CARE

(71) Applicant: ZOLL Medical Corporation, Chelmsford, MA (US)

(72) Inventors: Tracy N. Ashmore, Frederick, CO (US); Annemarie E. Silver, Bedford, MA (US); Patricia A. Daggett, Billerica, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 258 days.

(21) Appl. No.: 17/442,880

(22) PCT Filed: Mar. 27, 2020

(86) PCT No.: PCT/US2020/025171
§ 371 (c)(1),
(2) Date: Sep. 24, 2021

(87) PCT Pub. No.: WO2020/205495
PCT Pub. Date: Oct. 8, 2020

(65) Prior Publication Data

US 2022/0157418 A1 May 19, 2022

Related U.S. Application Data

(60) Provisional application No. 62/826,278, filed on Mar. 29, 2019.

(51) Int. Cl.
*G16H 10/60* (2018.01)
*G16H 40/63* (2018.01)

(52) U.S. Cl.
CPC ............ *G16H 10/60* (2018.01); *G16H 40/63* (2018.01)

(58) Field of Classification Search
None
See application file for complete search history.

(56) References Cited

U.S. PATENT DOCUMENTS 5,437,284 A 8/1995 Verrier et al.
5,687,738 A 11/1997 Shapiro et al.
(Continued)

FOREIGN PATENT DOCUMENTS

WO 2011/126823 10/2011
WO 2012/100219 7/2012
(Continued)

OTHER PUBLICATIONS

Eftestøl et al., Towards the Automated Analysis and Database Development of Defibrillator Data from Cardiac Arrest, BioMed Research International (2014), 276965, https://doi.org/10.1155/2014/276965 (Year: 2014).*

(Continued)

*Primary Examiner* — Jonathon A. Szumny
*Assistant Examiner* — Nicholas Akogyeram, II
(74) *Attorney, Agent, or Firm* — Finch & Maloney PLLC

(57) ABSTRACT

A system for documenting emergency medical events related to treatment of a patient is provided. The system includes a medical device configured to obtain physiological information from the patient and generate a first plurality of log entries that mark events that occur during treatment of the patient. The system also includes a mobile device configured to receive input for generating a second plurality of log entries that mark events that occur during treatment, establish a communicative connection with the medical device to access the first plurality of time-stamped log entries, and present, during the treatment of the patient, a single consolidated event log that includes the first plurality of log entries and the second plurality of log entries.

33 Claims, 53 Drawing Sheets

(56) References Cited

U.S. PATENT DOCUMENTS 5,785,043 A 7/1998 Cyrus et al.
6,609,023 B1 8/2003 Fischell et al.
7,194,300 B2 3/2007 Korzinov
7,462,153 B2 12/2008 Bostian et al.
7,502,643 B2 3/2009 Farringdon et al.
8,494,576 B1 7/2013 Bye et al.
8,542,827 B2 9/2013 Razzell
8,668,644 B2 3/2014 Ong et al.
8,932,220 B2 1/2015 Ong et al.
8,951,193 B2 2/2015 Ong et al.
9,125,050 B2 9/2015 Taylor et al.
9,154,191 B2 10/2015 Shimshoni
9,167,968 B2 10/2015 Saeed et al.
9,295,429 B2 3/2016 Ong et al.
9,420,957 B2 8/2016 Ong et al.
9,687,195 B2 6/2017 Sims et al.
9,737,656 B2 8/2017 Rosinko
10,055,549 B2 8/2018 Chung et al.
2004/0064062 A1 4/2004 Zhou et al.
2004/0215090 A1 10/2004 Erkkila et al.
2004/0267570 A1 12/2004 Becker
2005/0165321 A1 7/2005 Fischell et al.
2005/0192846 A1 9/2005 De Zwart et al.
2005/0234354 A1 10/2005 Rowlandson et al.
2005/0234355 A1 10/2005 Rowlandson
2006/0062734 A1* 3/2006 Melker .................. G16H 80/00 424/10.1
2006/0084883 A1 4/2006 Linker
2006/0234202 A1 10/2006 Brown
2007/0208266 A1 9/2007 Hadley
2008/0167567 A1 7/2008 Bashour et al.
2008/0188763 A1 8/2008 John et al.
2008/0221633 A1 9/2008 Linker
2009/0006127 A1* 1/2009 Bahar .................... G06Q 10/10 705/2
2009/0054741 A1 2/2009 McAleer
2009/0093686 A1 4/2009 Hu et al.
2009/0146822 A1 6/2009 Soliman
2009/0198513 A1* 8/2009 Hamadeh ............... G16H 30/20 705/2
2009/0228061 A1 9/2009 Lian et al.
2009/0234410 A1 9/2009 Libbus et al.
2009/0275848 A1 11/2009 Brockway et al.
2010/0004710 A1* 1/2010 Kellum ................ A61B 5/0002 607/5
2010/0030034 A1 2/2010 Schulhauser et al.
2010/0030293 A1 2/2010 Sarkar et al.
2010/0280335 A1 11/2010 Carlson et al.
2010/0298718 A1 11/2010 Gilham et al.
2011/0137131 A1 6/2011 Adourian et al.
2011/0184296 A1 7/2011 Vajdic et al.
2011/0201511 A1 8/2011 Hayes et al.
2011/0202486 A1 8/2011 Fung et al.
2012/0022336 A1 1/2012 Teixeira
2012/0289153 A1 11/2012 Dobyns
2013/0087609 A1 4/2013 Nichol et al.
2013/0176230 A1* 7/2013 Georgiev ............... G08C 17/02 345/173
2013/0197924 A1 8/2013 Kocis et al.
2013/0197942 A1 8/2013 Chiu et al.
2013/0291060 A1* 10/2013 Moore ................ G06F 21/6254 726/1
2013/0331719 A1 12/2013 Freeman et al.
2014/0181535 A1 6/2014 Smith et al.
2014/0249601 A1* 9/2014 Bachinski .......... A61N 1/36034 607/59
2014/0257122 A1 9/2014 Ong et al.
2015/0018702 A1 1/2015 Galloway et al.
2015/0088020 A1 3/2015 Dreisbach et al.
2015/0094552 A1 4/2015 Golda et al.
2015/0100335 A1* 4/2015 Englehard .............. G16H 40/63 705/2
2015/0111493 A1 4/2015 Berkema et al.
2015/0118966 A1 4/2015 Locker et al.
2015/0164349 A1 6/2015 Gopalakrishnan et al.
2015/0223752 A1* 8/2015 Kurtz ................... A61B 5/4839 434/262
2015/0227694 A1* 8/2015 Grimley ................. G16H 15/00 705/3
2015/0304478 A1* 10/2015 Kim ....................... G16H 40/63 455/414.3
2015/0342489 A1 12/2015 Bhaumik et al.
2015/0351647 A1* 12/2015 Dantu ................ A61B 5/02438 601/41
2015/0359466 A1* 12/2015 Tilvis .................... H04W 4/025 600/595
2016/0093205 A1 3/2016 Boyer
2016/0120430 A1 5/2016 Bayasi et al.
2016/0135706 A1 5/2016 Sullivan et al.
2016/0193437 A1 7/2016 Bao et al.
2016/0196387 A1 7/2016 Whannel et al.
2016/0248792 A1 8/2016 Tidwell et al.
2017/0041315 A1 2/2017 Giobbi
2017/0252571 A1* 9/2017 Dascoli ................ A61N 1/3925
2017/0296107 A1 10/2017 Reid et al.
2017/0325091 A1 11/2017 Freeman et al.
2018/0028409 A1* 2/2018 Doshi ................... A61J 7/0427
2019/0019573 A1 1/2019 Lake et al.
2019/0079943 A1* 3/2019 Snavely ............ G06F 16/24568
2021/0058760 A1* 2/2021 Hardy ................... H04W 4/029

FOREIGN PATENT DOCUMENTS

WO WO-2014141081 A1 * 9/2014 ............. G16H 40/63
WO 2020/205495 10/2020

OTHER PUBLICATIONS

Chen, et al., "The Kaiser Permanente Electronic Health Record: Transforming And Streamlining Modalities of Care," HealthAffairs, vol. 28, No. 2, Mar./Apr. 2009. 28 pages.
International Search Report and Written Opinion received for PCT/US2020/025171. Mail Date: Jul. 28, 2020. 30 pages.
ZOLL Data Systems, "CodeNet Writer," Getting Started Guide-Version 5.20, Jan. 18, 2011. 86 pages.
ZOLL Data Systems, "ZOLL Code Writer User Guide," Version 5.80. (2016), 21 pages.
Lewicke, et al., "Sleep versus wake classification from heart rate variability using computational intelligence: consideration of rejection in classification models," IEEE Transactions on Biomedical Engineering, Dec. 26, 2007, 55(1):108-18.
Li et al., "An algorithm used for ventricular fibrillation detection without interrupting chest compression," IEEE Transactions on Biomedical Engineering, Jan. 1, 2012 59(1):78-86.
Williamson, et al., "Forecasting respiratory collapse: theory and practice for averting life-threatening infant apneas," Respiratory Physiology & Neurobiology, Nov. 1, 2013, 189(2):223-3 I.
International Search Report and Written Opinion received for PCT/US2015/060730. Mail Date: Mar. 16, 2016. 20 pages.
International Preliminary Report on Patentability received for PCT/US2015/060730. Mail Date: May 26, 2017. 17 pages.
Extended European Search Report received for EP Application No. 21168424.6, dated Sep. 14, 2021. 9 pages.
NXP, NFC for embedded applications, Your critical link for the Internet of Things, 2014, 20 pages.
Extended European Search Report in European Application No. 20784919.1, dated Nov. 16, 2022 (9 pages).
International Preliminary Report on Patentability received for PCT/US2020/025171. Mail Date: Oct. 14, 2021. 25 pages.
1 European Examination Report in European Application No. 20784919.1, dated Aug. 19, 2025 (11 pages).

* cited by examiner

3400

Arrest Survival
Displays the percentage of cardiac arrest cases that survival outcome.

Export:
PDF

Date range: 5/1/2018 - 7/31/2018
Report type: Arrest Survival
Case Type: Cardiac arrest
Patient age group: No filter
Event witnessed: No filter
Event location: No filter
ROSC duration: No filter
First pulseless rhythm: No filter Arrest Survival (%)
Total arrests: 8

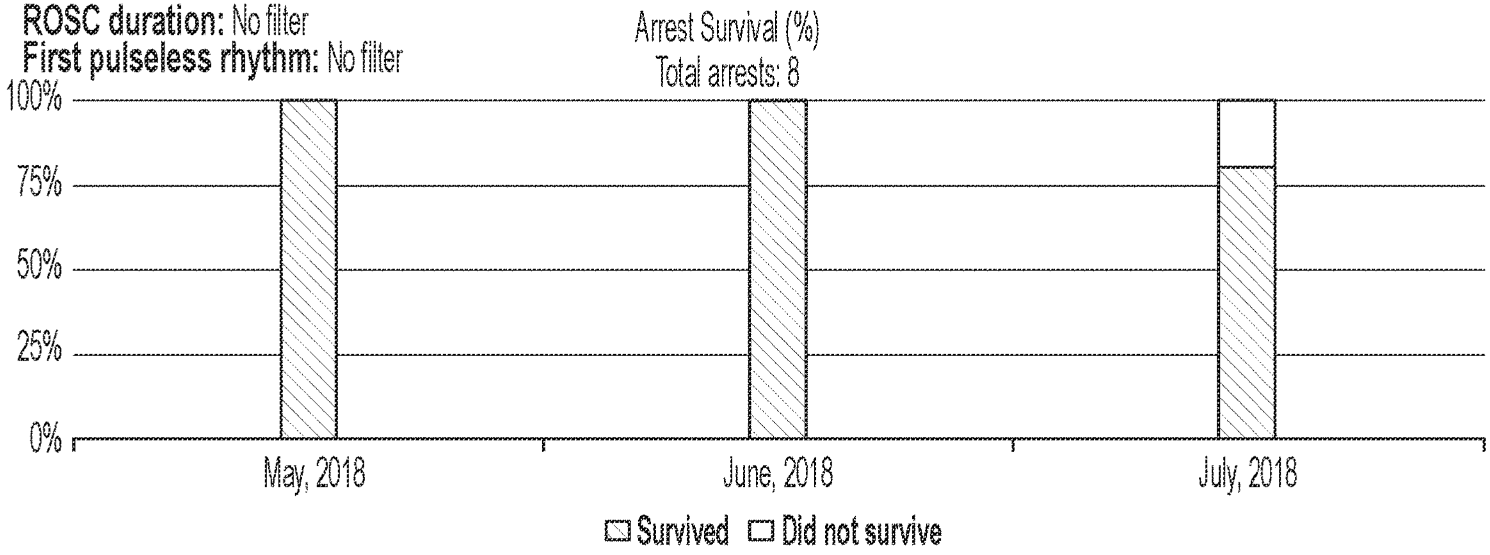

| Month | Survived arrest | Total arrests | % Survival |
|---|---|---|---|
| May, 2018 | 1 | 1 | 100 |
| June, 2018 | 2 | 2 | 100 |
| July, 2018 | 4 | 5 | 80 |

Average survival rate: 93%

FIG. 34

| Monthly CPR Metrics | Targets | Oct 2018 | Nov 2018 | Dec 2018 |
|---|---|---|---|---|
| Total Arrests (# w/ Shocks) | | 4 (3) | 2 (1) | 2 (2) |
| Avg. Compression Quality (%) | ≥ 60% | 16 | 1 | 47 |
| Avg. Depth (cm.) | 5 to 6 cm | 4.57 | 8.13 | 4.57 |
| Avg. Rate (cpm) | 100 to 120 cpm | 81 | 91 | 116 |
| Avg. CCRV (mm/s) | ≥ 0 mm/s | 233 | 306 | 245 |
| In Target - Depth (%) | ≥ 60 % | 20 | 5 | 47 |
| In Target - Rate (%) | ≥ 60 % | 50 | 38 | 87 |
| Avg. CCF (%) | ≥ 60 % | 52 | 51 | 83 |
| Avg. Pre-shock Pause (sec.) | ≤ 5 sec. | 12 | 14 | 9 |
| Avg. Post-shock Pause (sec.) | ≤ 5 sec. | 8 | 7 | 2 |
| Avg. Vent. T-Vol. | 500-600 mL | 610 | 420 | 560 |
| Avg. Vent. Rate | 10-12 bpm | 10.2 | 11.4 | 14.2 |
| In Target-Vent. T-Vol. (%) | ≥ 60 % | 50 | 35 | 78 |
| In Target-Vent. Rate (%) | ≥ 60 % | 60 | 85 | 34 |

SYSTEMS AND METHODS FOR DOCUMENTING EMERGENCY CARE

RELATED APPLICATIONS

The present application relates to U.S. patent application Ser. No. 14/941,302, filed Nov. 13, 2015, published as U.S. Publication No. 2016/0135706, and titled "Medical Premonitory Event Estimation", which is hereby incorporated herein by reference in its entirety. The present application relates to U.S. patent application Ser. No. 15/464,515, filed Mar. 21, 2017, published as U.S. Publication No. 2017/0325091 and titled "Establishing Secure Communication at an Emergency Care Scene", which is hereby incorporated herein by reference in its entirety. The present application is a U.S. national stage entry from International Application No. PCT/US2020/025171 filed Mar. 27, 2020, and titled "Systems and Methods for Documenting Emergency Care", which claims the benefit of U.S. Provisional Patent Application Ser. No. 62/826,278, filed Mar. 29, 2019, and titled "Systems and Methods for Documenting Emergency Care", both of which are hereby incorporated herein by reference in their entireties.

BACKGROUND

The present disclosure is directed to systems and methods for documenting emergency medical care.

Electronic Health Record (EHR) systems enable medical practitioners to document patient encounters. EHR systems receive and store a variety of patient information, such as medical history prior to an encounter, symptoms that lead to the encounter, any diagnosis identified during the encounter, treatments prescribed as a result of the encounter, and outcomes resulting from the treatments. EHR systems have been widely adopted within the medical community. The widespread use of EHR systems has streamlined sharing of patient information among practitioners in some situations, which in turn has resulted in higher quality emergency care.

EHR systems include endpoint devices that provide practitioners with access to patient information at the point of care. These endpoint devices implement interfaces that are necessarily complex due to the volume and structural relationships inherent in patient information. However, these interfaces meet the needs of many practitioners and are generally considered only a minor nuisance in view of the wealth of information available to practitioners via EHR systems.

SUMMARY

In at least one example, a system for providing documentation of emergency medical events related to treatment of a patient is provided. The system includes a medical device having and at least one first processor and memory configured to obtain physiological information from the patient, and generate a first plurality of time-stamped log entries that mark events that occur during treatment of the patient; and a mobile computing device having a user interface and at least one second processor and memory configured to: receive a plurality of inputs via the user interface for generating a second plurality of time-stamped log entries that mark further events that occur during treatment of the patient, establish a communicative connection with the medical device to access the first plurality of time-stamped log entries, and present, during the treatment of the patient, a single consolidated event log via the user interface that includes a first plurality of events associated with the first plurality of time-stamped log entries and a second plurality of events associated with the second plurality of time-stamped log entries.

In the system, the at least one second processor and memory can be further configured to enable a first type of interaction via the user interface with the first plurality of events, and enable a second type of interaction via the user interface with the second plurality of events. The system can further comprise at least one additional computing device configured to establish a communicative connection with the medical device to access the first plurality of time-stamped log entries, and establish a communicative connection with the mobile computing device to access the second plurality of time-stamped log entries. The at least one additional computing device can have an additional user interface and can be configured to present via the additional user interface a first plurality of events associated with the first plurality of time-stamped log entries and a second plurality of events associated with the second plurality of time-stamped log entries. In the system, the at least one additional computing device can be configured to enable the first type of interaction via the additional user interface with the first plurality of events; and enable the second type of interaction via the additional user interface with the second plurality of events.

In the system, the mobile computing device can be configured to establish the communicative connection with the medical device based on a proximity-based detection. The mobile computing device can include at least one sensor for providing the proximity-based detection. The proximity-based detection can include a detection based on a distance of less than 10 cm between the medical device and the mobile computing device. The at least one sensor can include at least one of a camera, an NFC tag, and a RFID tag. The medical device can include a barcode or QR code and the at least one sensor can include the camera for capturing an image of the barcode or QR code to provide the proximity-based detection. The medical device can include an NFC tag corresponding to the NFC tag of the mobile computing device for providing the proximity-based detection. The medical device can include a RFID tag corresponding to the RFID tag of the mobile computing device for providing the proximity-based detection. The medical device can include a defibrillator.

In the system, the medical device can be configured to store patient identification information associated with the first plurality of time-stamped log entries. The mobile computing device can be configured to access the patient identification information via the communicative connection with the medical device. The mobile computing device can be configured to display on the user interface an option to select between an adult documentation mode and a pediatric documentation mode. When the adult documentation mode is selected the user interface can provide adult-specific input options to include in the second plurality of time-stamped log entries and when the pediatric documentation mode is selected the user interface can provide pediatric-specific input options to include in the second plurality of time-stamped log entries.

In the system, the mobile computing device can be configured to display an electrotherapy timer on the user interface indicating a documented time elapsed since electrotherapy has been administered to the patient. The mobile computing device can be configured to display a documented indication of how many times electrotherapy has been administered to the patient. The second plurality of time-stamped log entries can include an electrotherapy entry indicating a documented time that electrotherapy has been administered to the patient. The medical device can be configured to store a plurality of chest compression quality metrics and the mobile computing device can be configured to access the plurality of chest compression quality metrics via the communicative connection with the medical device. The mobile computing device can be configured to present via the user interface a summary of the chest compression quality metrics.

In the system, the mobile computing device can be configured to display a CPR timer on the user interface indicating a documented time elapsed since chest compressions have been initiated. The CPR timer can provide a notification after 2 minutes have elapsed on the CPR timer. The notification can include at least one of flashing, highlighting, and changing color of the CPR timer. The mobile computing device can be configured to display a CPR idle timer on the user interface indicating a documented time elapsed since chest compressions have paused. The CPR idle timer can provide a notification after 10 seconds have elapsed on the CPR idle timer. The notification can include at least one of flashing, highlighting, and changing color of the CPR idle timer. The mobile computing device can be configured to display a documented indication of how many times chest compressions have been initiated and paused.

In the system, the second plurality of time-stamped log entries can include a CPR entry indicating a documented time that chest compressions have been initiated. The mobile computing device can be configured to display a drug timer on the user interface indicating a documented time elapsed since a drug has been administered. The drug timer can provide a notification after 3 minutes have elapsed on the drug timer. The notification can include at least one of flashing, highlighting, and changing color of the drug timer. The mobile computing device can be configured to display a documented indication of how many times a drug has been administered. The second plurality of time-stamped log entries can include a drug entry indicating a documented time that a drug has been administered. The communicative connection can include a direct connection between the medical device and the mobile computing device. The communicative connection can include a connection between the medical device and the mobile computing device via at least one additional computing device.

In at least one example, a system for providing documentation of emergency medical events related to treatment of a patient is provided. The system includes at least one first computing device having at least one first processor and memory configured to store a first plurality of time-stamped log entries that mark events that occurred during treatment of the patient; and a second computing device comprising a mobile computing device having a user interface and at least one second processor and memory configured to receive a plurality of inputs via the user interface for generating a second plurality of time-stamped log entries that mark further events that occurred during treatment of the patient, establish a communicative connection with the at least one first computing device to access the first plurality of time-stamped log entries, present a consolidated event log via the user interface that includes a first plurality of events associated with the first plurality of time-stamped log entries and a second plurality of events associated with to the second plurality of time-stamped log entries, enable a first type of interaction via the user interface with the first plurality of events, and enable a second type of interaction via the user interface with the second plurality of events.

In the system, to enable the first type of interaction can include to disable controls associated with the first plurality of time-stamped log entries. To enable the first of type interaction can include to enable controls associated with the first plurality of time-stamped log entries to receive input and to disable the controls from storing modifications to the first plurality of time-stamped log entries. To enable the first of type interaction can include to enable controls associated with the first plurality of time-stamped log entries to receive input and to enable the controls to modify to the first plurality of time-stamped log entries. To enable the first of type interaction can include to enable controls associated with the first plurality of time-stamped log entries to receive input; display a prompt to confirm modifications to the first plurality of time-stamped log entries indicated by the input; and to enable, in response to receiving confirmation via the prompt, the controls to modify to the first plurality of time-stamped log entries according to the input. To enable the second type of interaction can include to enable controls associated with the second plurality of time-stamped log entries to modify the second plurality of time-stamped log entries. To enable the second type of interaction can include to provide an additional screen comprising enable controls associated with the second plurality of time-stamped log entries; and to enable the controls to modify the second plurality of time-stamped log entries.

The system can further comprise a medical device configured to obtain physiological information from the patient; and generate and transmit to the at least one first computing device the first plurality of time-stamped log entries. The second computing device can be configured to identify the medical device associated with the first plurality of time-stamped log entries based on a proximity-based detection. The second computing device can include at least one sensor for identifying the medical device based on the proximity-based detection. The proximity-based detection can include a detection based on a distance of less than 10 cm between the medical device and the second computing device. The at least one sensor can include one or more of a camera, an NFC tag, and a RFID tag. The medical device can include a barcode or QR code and the at least one sensor can include the camera for capturing an image of the barcode or QR code to provide the proximity-based detection. The medical device can include an NFC tag corresponding to the NFC tag of the second computing device for providing the proximity-based detection. The medical device can include a RFID tag corresponding to the RFID tag of the second computing device for providing the proximity-based detection.

In the system, the at least one first computing device can be configured to store patient identification information associated with the first plurality of time-stamped log entries. The second computing device can be configured to identify the patient associated with the first plurality of time-stamped log entries based on a proximity-based detection. The second computing device can be configured to select the identified patient based on the proximity-based detection to access the patient identification information via the communicative connection with the at least one first computing device. The system can further include a patient identification component for providing the proximity-based detection, wherein the second computing device can include at least one sensor for identifying the patient identification component. The at least one sensor can include at least one of a camera, an NFC tag, and a RFID tag. The patient identification component can include a barcode or QR code and the at least one sensor can include the camera for capturing an image of the barcode or QR code to provide the proximity-based detection. The patient identification component can include an NFC tag corresponding to the NFC tag of the second computing device for providing the proximity-based detection. The patient identification component can include a RFID tag corresponding to the RFID tag of the second computing device for providing the proximity-based detection. The patient identification component can include at least one of a label, wrist band, article of clothing, and wearable item coupled to the patient. The second computing device can be configured to present via the user interface the patient identification information.

In the system, the at least one first computing device can be configured to store a plurality of chest compression quality metrics and the second computing device can be configured to access the plurality of chest compression quality metrics via the communicative connection with the at least one first computing device. The second computing device can be configured to present via the user interface a summary of the chest compression quality metrics. The second computing device can be configured to display on the user interface an option to select between an adult documentation mode and a pediatric documentation mode. When the adult documentation mode is selected the user interface can provide adult-specific input options to include in the second plurality of time-stamped log entries and when the pediatric documentation mode is selected the user interface can provide pediatric-specific input options to include in the second plurality of time-stamped log entries.

In the system, the second computing device can be configured to display an electrotherapy timer on the user interface indicating a documented time elapsed since electrotherapy has been administered to the patient. The second computing device can be configured to display a documented indication of how many times electrotherapy has been administered to the patient. The second plurality of time-stamped log entries can include an electrotherapy entry indicating a documented time that electrotherapy has been administered to the patient. The medical device can include a defibrillator.

In the system, the at least one first computing device can have an additional interface and can be configured to access the second plurality of time-stamped log entries via the communicative connection. The at least one first computing device can be configured to provide, via the additional interface, the first plurality of events and the second plurality of events. The at least one first computing device can be configured to enable the first type of interaction via an additional user interface with the first plurality of events; and enable the second type of interaction via the additional user interface with the second plurality of events.

In at least one example, a system for providing documentation of emergency medical events related to treatment of a patient is provided. The system includes at least one first computing device having a first user interface and at least one first processor and memory configured to store a first plurality of time-stamped log entries that mark events that occurred during treatment of the patient; and a second computing device comprising a mobile computing device having a second user interface and at least one second processor and memory configured to receive a plurality of inputs via the second user interface for generating a second plurality of time-stamped log entries that mark further events that occurred during treatment of the patient, wherein the at least one first computing device is further configured to establish a communicative connection with the second computing device to access the second plurality of time-stamped log entries, present a single consolidated event log via the first user interface that includes a first plurality of events associated with the first plurality of time-stamped log entries and a second plurality of events associated with the second plurality of time-stamped log entries, enable a first type of interaction via the first user interface with the first plurality of events, and enable a second type of interaction via the first user interface with the second plurality of events.

The system can further include a medical device configured to obtain physiological information from the patient; and generate and transmit to the at least one first computing device the first plurality of time-stamped log entries. The second computing device can be configured to identify the medical device associated with the first plurality of time-stamped log entries based on a proximity-based detection. The second computing device can include at least one sensor for identifying the medical device based on the proximity-based detection. The proximity-based detection can include a detection based on a distance of less than 10 cm between the medical device and the second computing device. The at least one sensor can include at least one of a camera, an NFC tag, and a RFID tag. The medical device can include a barcode or QR code and the at least one sensor can include the camera for capturing an image of the barcode or QR code to provide the proximity-based detection. The medical device can include an NFC tag corresponding to the NFC tag of the second computing device for providing the proximity-based detection. The medical device can include a RFID tag corresponding to the RFID tag of the second computing device for providing the proximity-based detection.

In the system, the at least one first computing device can be configured to store patient identification information associated with the first plurality of time-stamped log entries. The second computing device can be configured to identify the patient associated with the first plurality of time-stamped log entries based on a proximity-based detection. The second computing device can be configured to select the identified patient based on the proximity-based detection to access the patient identification information via the communicative connection with the at least one first computing device. The system can further include a patient identification component for providing the proximity-based detection, wherein the second computing device can include at least one sensor for identifying the patient identification component. The at least one sensor can include at least one of a camera, an NFC tag, and a RFID tag. The patient identification component can include a barcode or QR code and the at least one sensor can include the camera for capturing an image of the barcode or QR code to provide the proximity-based detection. The patient identification component can include an NFC tag corresponding to the NFC tag of the second computing device for providing the proximity-based detection. The patient identification component can include a RFID tag corresponding to the RFID tag of the second computing device for providing the proximity-based detection. The patient identification component can include at least one of a label, wrist band, article of clothing, and wearable item coupled to the patient. The at least one first computing device can be configured to present via the first user interface the patient identification information.

In the system, the second computing device can be configured to display on the user interface an option to select between an adult documentation mode and a pediatric documentation mode. When the adult documentation mode is selected the user interface can provide adult-specific input options to include in the second plurality of time-stamped log entries and when the pediatric documentation mode is selected the user interface can provide pediatric-specific input options to include in the second plurality of time-stamped log entries.

In the system, the second computing device can be configured to display an electrotherapy timer on the user interface indicating a documented time elapsed since electrotherapy has been administered to the patient. The second computing device can be configured to display a documented indication of how many times electrotherapy has been administered to the patient. The second plurality of time-stamped log entries can include an electrotherapy entry indicating a documented time that electrotherapy has been administered to the patient. The medical device can include a defibrillator.

In the system, the second computing device can be configured to access the first plurality of time-stamped log entries via the communicative connection. The second computing device can be configured to present via the second user interface the first plurality of events and the second plurality of events. The second computing device can be configured to enable the first type of interaction via the second user interface with the first plurality of events; and enable the second type of interaction via the second user interface with the second plurality of events.

In at least one example, a system for providing documentation of emergency medical events related to treatment of a patient is provided. The system includes a mobile computing device having a user interface and at least one processor and memory configured to receive a plurality of inputs via the user interface for generating a plurality of time-stamped log entries that mark events that occur during treatment of the patient, establish a communicative connection with at least one of a medical device and an additional computing device to access an additional plurality of time-stamped log entries and a plurality of chest compression quality metrics, present a single consolidated event log via the user interface that includes a plurality of events associated with the plurality of time-stamped log entries and an additional plurality of events associated with the additional plurality of time-stamped log entries, and present via the user interface a summary of the chest compression quality metrics.

In the system, the plurality of chest compression quality metrics can include at least one of a percentage of compressions that fall within a target depth, a percentage of compressions that fall within a target rate, an average depth of compressions, an average rate of compressions. The at least one processor and memory can be further configured to access, via the communicative connection, the plurality of chest compression quality metrics during the treatment of the patient. The mobile computing device can be configured to enable a first type of interaction via the user interface with the plurality of events; and enable a second type of interaction via the user interface with the additional plurality of events.

The system can further include a medical device configured to obtain physiological information from the patient; and generate the additional plurality of time-stamped log entries. The mobile computing device can be configured to establish the communicative connection with the medical device based on a proximity-based detection. The mobile computing device can include at least one sensor for providing the proximity-based detection. The proximity-based detection can include a detection based on a distance of less than 10 cm between the medical device and the mobile computing device. The at least one sensor can include at least one of a camera, an NFC tag, and a RFID tag. The medical device can include a defibrillator.

The system an further include the additional computing device configured to store the additional plurality of time-stamped log entries. The additional computing device can have an additional user interface and can be configured to access the plurality of time-stamped log entries via the communicative connection. The additional computing device can be configured to present via the additional user interface the plurality of events and the additional plurality of events. The additional computing device can be configured to enable a first type of interaction via the additional user interface with the plurality of events; and enable a second type of interaction via the additional user interface with the additional plurality of events.

In the system, the mobile computing device can be configured to display on the user interface an option to select between an adult documentation mode and a pediatric documentation mode. When the adult documentation mode is selected the user interface can provide adult-specific input options to include in the plurality of time-stamped log entries and when the pediatric documentation mode is selected the user interface can provide pediatric-specific input options to include in the plurality of time-stamped log entries. The mobile computing device can be configured to display an electrotherapy timer on the user interface indicating a documented time elapsed since electrotherapy has been administered to the patient. The mobile computing device can be configured to display a documented indication of how many times electrotherapy has been administered to the patient. The plurality of time-stamped log entries can include an electrotherapy entry indicating a documented time that electrotherapy has been administered to the patient. The mobile computing device can be configured to display a CPR timer on the user interface indicating a documented time elapsed since chest compressions have been initiated. The CPR timer provides a notification after 2 minutes have elapsed on the CPR timer. The notification can include at least one of flashing, highlighting, and changing color of the CPR timer.

In the system, the mobile computing device can be configured to display a CPR idle timer on the user interface indicating a documented time elapsed since chest compressions have paused. The CPR idle timer provides a notification after 10 seconds have elapsed on the CPR idle timer. The notification can include at least one of flashing, highlighting, and changing color of the CPR idle timer. The mobile computing device can be configured to display a documented indication of how many times chest compressions have been initiated and paused. The plurality of time-stamped log entries can include a CPR entry indicating a documented time that chest compressions have been initiated. The mobile computing device can be configured to display a drug timer on the user interface indicating a documented time elapsed since a drug has been administered. The drug timer can provides a notification after 3 minutes have elapsed on the drug timer. The notification can include at least one of flashing, highlighting, and changing color of the drug timer. The mobile computing device can be configured to display a documented indication of how many times a drug has been administered. The plurality of time-stamped log entries can include a drug entry indicating a documented time that a drug has been administered.

In at least one example, a system for providing documentation of emergency medical events related to treatment of a patient is provided. The system includes a mobile computing device having a user interface and at least one processor and memory configured to receive a plurality of inputs via the user interface for generating a plurality of time-stamped log entries that mark events that occurred during treatment of the patient; display on the user interface an option to select between a first documentation mode and a second documentation mode, wherein when the first documentation mode is selected the user interface provides a first set of input options to include in the plurality of time-stamped log entries, and when the second documentation mode is selected the user interface provides a second set of input options to include in the plurality of time-stamped log entries, the second set being distinct from the first set, establish a communicative connection with at least one of a medical device and another computing device to access an additional plurality of time-stamped log entries; and present a single consolidated event log via the user interface that includes a plurality of events associated with the plurality of time-stamped log entries and an additional plurality of events associated with the additional plurality of time-stamped log entries.

In the system, the first documentation mode can be specific to a first patient characteristic and the second documentation mode can be specific to a second patient characteristic. The first patient characteristic can be a first range of ages and the second patient characteristic can be a second range of ages. The first range of ages can be 8 years old and above and the second range of ages can be less than 8 years old. In certain embodiments, a third range of ages related to neonates (e.g., less than 4-6 weeks old) may also be employed. The first set of input options can include adult-specific input options including at least one of drug dosage for adults and intubation tube size for adult patients. The second set of input options can include pediatric-specific input options comprising intubation tube size for pediatric patients. The second set of input options can include pediatric-specific input options including a technique of administering chest compressions for pediatric patients. The mobile computing device can be configured to enable a first type of interaction via the user interface with the plurality of events; and enable a second type of interaction via the user interface with the additional plurality of events.

The system can further include the medical device configured to obtain physiological information from the patient; and generate the additional plurality of time-stamped log entries. The mobile computing device can be configured to establish the communicative connection with the medical device based on a proximity-based detection. The mobile computing device can include at least one sensor for providing the proximity-based detection. The proximity-based detection can include a detection based on a distance of less than 10 cm between the medical device and the mobile computing device. The at least one sensor can include at least one of a camera, an NFC tag, and a RFID tag. The medical device can include a defibrillator.

The system can further include an additional computing device configured to store an additional plurality of time-stamped log entries. The additional computing device can have an additional user interface and can be configured to access the plurality of time-stamped log entries via the communicative connection. The additional computing device can be configured to present via the additional user interface the plurality of events and the additional plurality of events. The additional computing device can be configured to enable a first type of interaction via the additional user interface with the plurality of events; and enable a second type of interaction via the additional user interface with the additional plurality of events. The mobile computing device can be configured to access a plurality of chest compression quality metrics via the communicative connection with the medical device or an additional computing device. The mobile computing device can be configured to present via the user interface a summary of the chest compression quality metrics. The mobile computing device can be configured to display an electrotherapy timer on the user interface indicating a documented time elapsed since electrotherapy has been administered to the patient. The mobile computing device can be configured to display a documented indication of how many times electrotherapy has been administered to the patient. The plurality of time-stamped log entries can include an electrotherapy entry indicating a documented time that electrotherapy has been administered to the patient.

In the system, the mobile computing device can be configured to display a CPR timer on the user interface indicating a documented time elapsed since chest compressions have been initiated. The CPR timer can provides a notification after 2 minutes have elapsed on the CPR timer. The notification can include at least one of flashing, highlighting, and changing color of the CPR timer. The mobile computing device can be configured to display a CPR idle timer on the user interface indicating a documented time elapsed since chest compressions have paused. The CPR idle timer provides a notification after 10 seconds have elapsed on the CPR idle timer. The notification can include at least one of flashing, highlighting, and changing color of the CPR idle timer. The mobile computing device can be configured to display a documented indication of how many times chest compressions have been initiated and paused. The plurality of time-stamped log entries can include a CPR entry indicating a documented time that chest compressions have been initiated. The mobile computing device can be configured to display a drug timer on the user interface indicating a documented time elapsed since a drug has been administered. The drug timer can provide a notification after 3 minutes have elapsed on the drug timer. The notification can include at least one of flashing, highlighting, and changing color of the drug timer. The mobile computing device can be configured to display a documented indication of how many times a drug has been administered. The plurality of time-stamped log entries can include a drug entry indicating a documented time that a drug has been administered.

In at least one example, a mobile computing device to document emergency medical events related to treatment of a patient is provided. The mobile computing device includes a memory; a touchscreen; and a processor coupled to the memory and the touchscreen and configured to receive a plurality of inputs via the touchscreen for generating a plurality of time-stamped log entries that mark events that occurred during treatment of the patient, and display on the touchscreen an option to select between an adult documentation mode and a pediatric documentation mode, wherein when the adult documentation mode is selected the touchscreen provides adult-specific input options to include in the plurality of time-stamped log entries, and when the pediatric documentation mode is selected the touchscreen provides pediatric-specific input options to include in the plurality of time-stamped log entries.

In the mobile computing device, the adult-specific input options can include at least one of drug dosage for adults and intubation tube size for adult patients. The pediatric-specific input options can include intubation tube size for pediatric patients. The pediatric-specific input options can include a technique of administering chest compressions for pediatric patients. The processor can be further configured to display a CPR timer on the touchscreen indicating a documented time elapsed since chest compressions have been initiated.

The CPR timer can provides a notification after 2 minutes have elapsed on the CPR timer. The notification can include at least one of flashing, highlighting, and changing color of the CPR timer. The processor can be further configured to display a CPR idle timer on the touchscreen indicating a documented time elapsed since chest compressions have paused. The CPR idle timer can provide a notification after 10 seconds have elapsed on the CPR idle timer. The notification can include at least one of flashing, highlighting, and changing color of the CPR idle timer. The processor can be further configured to display a documented indication of how many times chest compressions have been initiated and paused. The plurality of time-stamped log entries can include a CPR entry indicating a documented time that chest compressions have been initiated. The processor can be further configured to display a drug timer on the touchscreen indicating a documented time elapsed since a drug has been administered. The drug timer can provide a notification after 3 minutes have elapsed on the drug timer. The notification can include at least one of flashing, highlighting, and changing color of the drug timer. The processor can be further configured to display a documented indication of how many times a drug has been administered. The plurality of time-stamped log entries can include a drug entry indicating a documented time that a drug has been administered.

In at least one example, a mobile computing device to document emergency medical events related to treatment of a patient is provided. The mobile computing device includes a memory; a touchscreen; and a processor coupled to the memory and the touchscreen and configured to provide a first control to initiate a first screen configured to receive a plurality of inputs via the touchscreen for generating a plurality of time-stamped log entries that mark events that occurred during treatment of the patient; provide a second control to transmit a notification to a device associated with a member of a rapid response team; provide a third control to initiate a second screen configured to receive a plurality of inputs via the touchscreen for recording measurements or assessments of factors used to estimate the risk of a patient undergoing acute physiologic deterioration; and provide a fourth control to display the estimate of the risk of a patient undergoing acute physiologic deterioration.

A system for estimating the risk of a patient undergoing acute physiologic deterioration and detection of medical premonitory events may be referred to herein as an "early warning system". The early warning system may be implemented as the calculation and display of a modified early warning score (MEWS). A modified early warning score (MEWS) is a simple guide used by medical personnel to quickly determine the risk of death of a subject. It is based on data derived from four physiological readings (systolic blood pressure, heart rate, respiratory rate, body temperature) and one observation (level of consciousness). The resulting observations are compared to a normal range to generate a single score. Alternatively, or in addition, the early warning system can be implemented as described further herein In the mobile computing device, the second screen can include a plurality of controls to receive the plurality of inputs. This plurality of controls can include a heart rate control to record a heart rate measurement of the patient; a respiratory rate control to record a respiratory rate measurement of the patient; a blood pressure control to record a blood pressure measurement of the patient; a body temperature control to record a body temperature measurement of the patient; and a neurologic state control to record an assessment of neurologic state of the patient. The second screen includes a control to transmit a notification to a device associated with a member of a code team. The second screen includes another instance of the second control to transmit the notification to the device associated with the member of the rapid response team. The processor can be further configured to display a CPR timer on the touchscreen indicating a documented time elapsed since chest compressions have been initiated. The CPR timer provides a notification after 2 minutes have elapsed on the CPR timer. The notification can include at least one of flashing, highlighting, and changing color of the CPR timer. The processor can be further configured to display a CPR idle timer on the touchscreen indicating a documented time elapsed since chest compressions have paused. The CPR idle timer can provide a notification after 10 seconds have elapsed on the CPR idle timer. The notification can include at least one of flashing, highlighting, and changing color of the CPR idle timer. The processor can be further configured to display a documented indication of how many times chest compressions have been initiated and paused. The plurality of time-stamped log entries can include a CPR entry indicating a documented time that chest compressions have been initiated. The processor can be further configured to display a drug timer on the touchscreen indicating a documented time elapsed since a drug has been administered. The drug timer can provide a notification after 3 minutes have elapsed on the drug timer. The notification can include at least one of flashing, highlighting, and changing color of the drug timer. The processor can be further configured to display a documented indication of how many times a drug has been administered. The plurality of time-stamped log entries can include a drug entry indicating a documented time that a drug has been administered.

In at least one example, a system for providing documentation of emergency medical events related to treatment of a patient is provided. The system includes a mobile computing device comprising a user interface, a first network interface configured to couple with a network, and at least one processor and memory coupled with the user interface and the first network interface and configured to receive a plurality of inputs via the user interface for generating a first plurality of time-stamped log entries marking first events that occur during the treatment of the patient, establish a first communicative connection with the network via the first network interface, receive, via the first communicative connection, a second plurality of time-stamped log entries generated by a medical device, the second plurality of time-stamped log entries marking second events that occur during the treatment of the patient, and present, during the treatment of the patient, a consolidated event log via the user interface that includes a first plurality of events associated with the first plurality of time-stamped log entries and a second plurality of events associated with to the second plurality of time-stamped log entries.

The system can further include the medical device. The medical device can include a second network interface; at least one sensor configured to couple to the patient; and one or more first processors and memory coupled with the second network interface and the at least one sensor and configured to store, in the memory, the second plurality of time-stamped log entries marking the second events that occur during the treatment of the patient, establish a second communicative connection with the network via the second network interface, and transmit, via the second communicative connection during the treatment of the patient, the second plurality of time-stamped log entries to a device coupled with the network.

The system can further include the device coupled to the network. The device can include the medical device and/or a server computer distinct from the medical device and the mobile computing device. The second plurality of time-stamped log entries can document a cardiopulmonary resuscitation (CPR) start time, a CPR end time, a type of CRP compressions delivered, a type of cardiac rhythm detected, a delivery time of a therapeutic shock, an amount of energy delivered within the therapeutic shock, and/or a number of therapeutic shocks delivered within an intervention. The mobile computing device can further include a sensor coupled with the at least one processor and the at least one processor and memory can be further configured to identify one or more physical objects based on a proximity-based detection. The one or more physical objects comprise medication, an endotracheal tube, an IV bag, and/or a badge of a physician. The plurality of inputs can include a selection of a vital signs control and the at least one processor is further configured to parse the second plurality of time-stamped log entries to identify entries comprising measurements of vital signs of the patient; and store, in the vital signs control, the measurements of the vital signs. The at least one processor can be further configured to transmit, via the first communicative connection, information stored in the consolidated event log to an electronic health records system distinct from the mobile computing device.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples disclosed herein and are incorporated in and constitute a part of this specification. However, the figures are not intended to limit the scope of the disclosure. The figures, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIG. 34 is a view of an arrest survival report screen provided by a log analysis application in accordance with at least one example disclosed herein.

DETAILED DESCRIPTION

Figure 1:
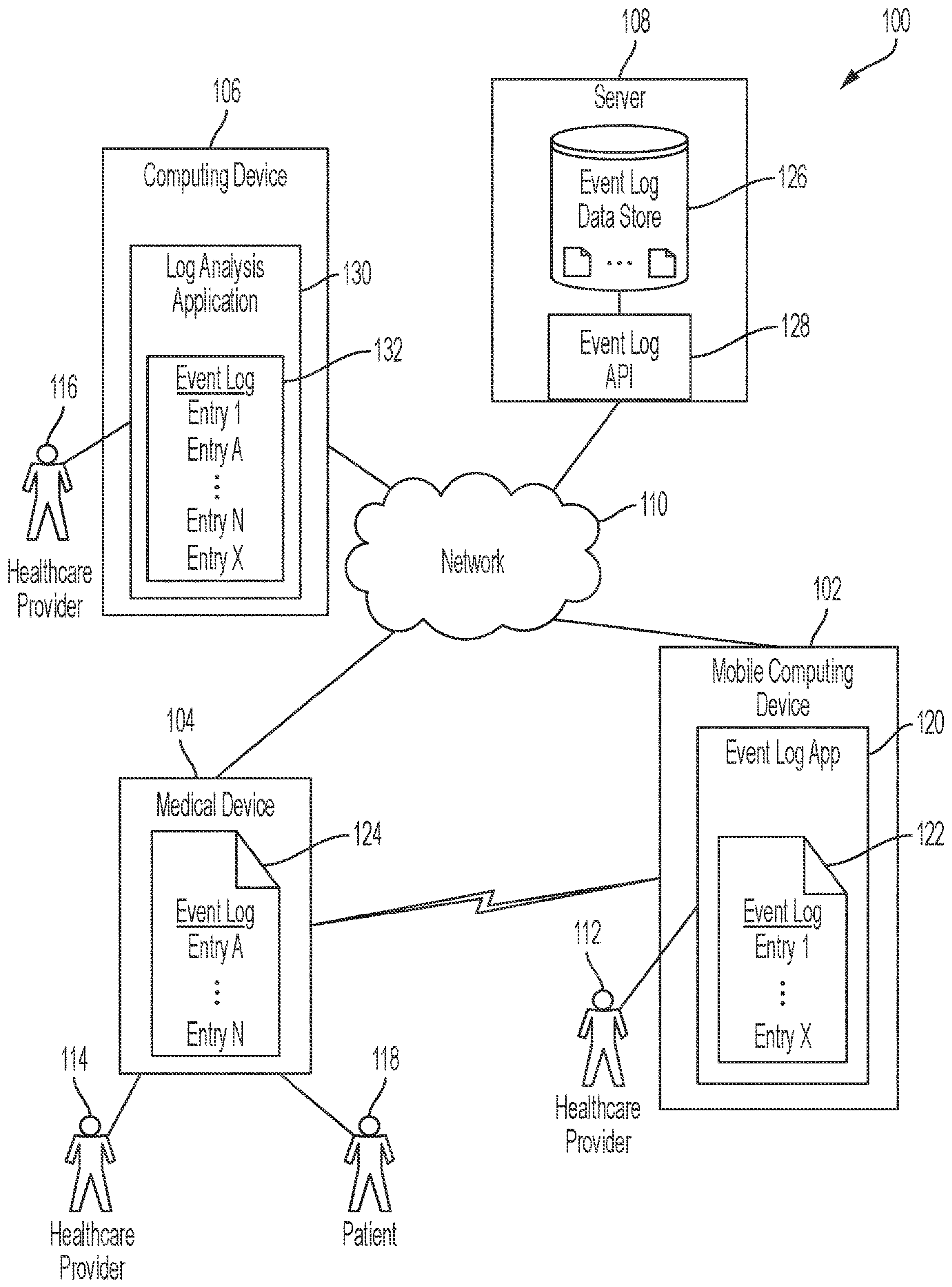
FIG. 1 is a block diagram illustrating a distributed system configured to document emergency care provided to a patient in accordance with at least one example disclosed herein.

While EHR systems provide a host of benefits, conventional interfaces and supporting processes of EHR systems have limitations, in some applications. For example, user interfaces presented by EHR endpoint devices are not ideal with respect to the convenient and expedient entry of data within the context of some emergency medical care procedures. Take, for instance, the running of a code blue.

Within the context of a hospital, a code blue refers to an event in which a patient has suffered cardiopulmonary arrest and requires immediate treatment. Many hospitals staff code teams whose responsibility it is to respond to a code blue by rushing to the patient and running an advanced cardiac life support code focused on the patient. Each of the individuals who make up the code team is a highly skilled healthcare provider, and each typically has a specific role to play during the code. Given that timeliness and accuracy of diagnosis and intervention is of the essence to achieve a successful outcome to the code blue, code teams work with a high degree of speed and urgency. Unfortunately, the complex user interfaces provided by EHR endpoints are often not well suited to match the speed and urgency with which code teams work and further are not conducive to accurate diagnosis, treatment, or recording of diagnosis and treatment information.

Aspects of the present disclosure are also applicable to other emergency situations in which, for example, rapid response or emergency medical teams are called upon to provide urgent medical care to deteriorating patients in order to prevent cardiopulmonary arrests from occurring. A rapid response team (RRT), also known as a medical emergency team (MET), medical emergency response team (MERT), and high acuity response team (HART), is a team of health care providers that responds to hospitalized patients with either early signs of deterioration or an elevated risk of a medical premonitory event (MPE) to prevent respiratory or cardiac arrest. The health care providers are trained in respiratory therapy, early resuscitation interventions and advanced life support and may include a physician, nurse, pharmacist, or respiratory therapist. The RRT, MET, MERT, HART or critical care outreach team (CCOT) are all different forms of the response component of the rapid response system. As is the case with code teams, EHR interfaces are often ill suited for use by RRTs to acquire accurate diagnosis and treatment information.

Thus, and in accordance with at least some of the examples described herein, systems and methods are provided that are specialized to the task of documenting emergency care during emergency medical treatment, such as for code events and/or other emergency situations. In some of these examples, these systems and methods include an event log application installed on a mobile computing device that is configured to provide a set of user interface screens that are tailored to easily, quickly, conveniently, and accurately record events and sometimes determine additional event details encountered during the emergency medical treatment. These interface screens can be provided, for example, via a touchscreen of a mobile computing device executing the event log application.

More specifically, in some examples, the event log application is configured to provide screens including controls that are labeled and associated with events commonly encountered during emergency medical treatment. For instance, events such as administration of CPR, epinephrine (EPI), and/or an electrotherapeutic shocks are commonly encountered while running a code blue and examples directed toward documenting a code blue have controls dedicated to recording these events. Many of these processes culminate in the storage of a date/time stamped entry that documents occurrence of specific events in an event log. The event log, in turn, documents the treatment provided to a patient and/or events that have occurred during the course of patient care.

In some examples, the event log application is further configured to respond to input selecting a control by executing a process that is associated with the control. For instance, in some examples, controls associated with administration of CPR, EPI, and shocks include timers and/or counters that are reset and/or incremented via execution of the process associated with the control. Further these processes can provide notifications after a threshold amount of time has elapsed since the control was last selected. For instance, the event log application can provide, via the CPR control, a notification (e.g., flashing icon, color change, textual prompt) after 2 minutes has passed since CPR chest compressions were started or after 10 seconds has elapsed since CPR was paused. This notification after a predefined period of time, typically 2 minutes, of chest compressions is to remind the user that an interval of CPR has passed and that another phase in treating the patient may be required, such as a period of electrocardiogram (ECG) analysis to determine whether the patient is in need of electrotherapy (e.g., defibrillation shock) or a short pause for one or more positive pressure ventilation breaths to be applied. Once this pause (e.g., for ECG analysis and/or ventilations) has passed, then chest compressions should immediately resume. Accordingly, the notification after 10 seconds of a pause in chest compressions may be appropriate to remind the user that chest compressions should resume. Similarly, in some examples, the event log application can provide, via the EPI control, a notification after 3 minutes has passed since EPI was last administered. Such a notification may be appropriate to remind the user that a subsequent dosage of EPI is to be administered. These notifications can include causing the control to flash, become highlighted, change color, prompt with text, and/or provide another visual indication. Or, in some cases, an audible and/or haptic notification may be provided by the mobile computing device.

In some examples, to further ease treatment documentation in specific situations, the event log application is configured to provide controls that enable a healthcare provider to change the documentation mode of the event log application to either adult mode or pediatric mode. While operating in adult mode, the event log application alters features of certain screens and controls to facilitate entries that mark events directed to events encountered when treating an adult. For instance, controls associated and labeled with approaches to CPR that are only available to adults are visible only while the event log application is operating in adult mode. Conversely, while operating in pediatric mode, the event log application alters features of certain screens and controls to facilitate entries that mark events directed to events encountered when treating a child. For instance, controls associated with approaches to CPR that are only available to children are visible only while the event log application is operating in pediatric mode.

In certain examples, the event log application is configured with controls to display a variety of information before, during, and after emergency treatment of a patient. For instance, in some examples, once the appropriate connections are made to acquire the relevant information, the event log application is configured to display patient identification information to the healthcare provider via a patient information screen. Further, in at least one example, the event log application is configured to display CPR quality metrics for manual chest compressions (e.g., chest compression metrics such as percentage of chest compressions that fall within a target depth, amount/percentage of compressions that fall within a target rate, an average depth of compressions, an average rate of compressions, etc.) and/or for manual ventilations (e.g., ventilation metrics such as percentage of ventilations that fall with a target tidal volume, amount/percentage of ventilations that fall within a target ventilation rate, average tidal volume, average ventilation rate, etc.) to the healthcare provider via a screen of the user interface. Further, in some examples, the event log application software is configured to provide screens with controls to receive MEWS factors and display MEWS scores calculated based on the MEWS factors. Further these screens may include a control that responds to input selecting the control by calling a rapid response or code team to, for example, the location of the mobile computing device.

In some examples, the event log application is configured to provide screens with controls to receive data entry from the user as necessary for the detection and estimation of MPEs and the display of that estimation. Alternatively or additionally, in some examples, the event log application is configured to acquire physiological data, such as ECG, SpO2, etc., via communication with a defibrillator/monitor in real time for input to the detection and estimation of the MPE. The Oxford English Dictionary defines 'premonition' as 'a strong feeling of something about to happen, esp. something unpleasant.' The Latin roots of 'premonition' are prae, before +monere, warn. As used herein, 'premonitory' means an indication that something has a likelihood or probability of occurring, and a 'medical premonitory event,' or MPE, means a medical event that has a likelihood or probability of occurring for a subject. The detection and estimation of medical premonitory events may thus be used as an early warning system to provide an individual and/or a medical professional time to prepare for a medical event, for example, to prepare for a potentially adverse or fatal degradation in the medical condition of a subject or patient, to potentially mitigate or avoid the adverse effects of the degradation, or even potentially completely avoid the degradation or event by timely, appropriate treatment.

Figure 51:
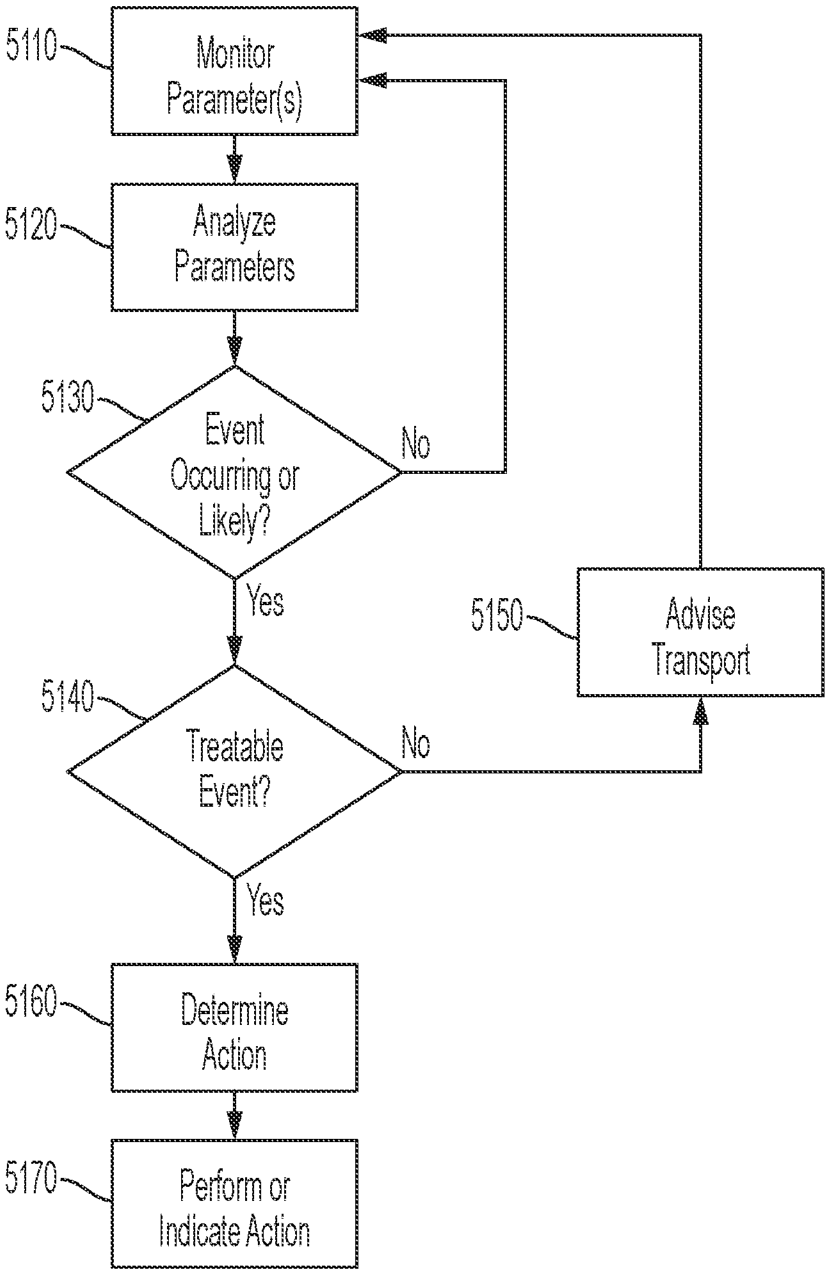
FIG. 51 is a flow chart of a medical premonitory event estimation and detection method in accordance with at least one example disclosed herein.

In some examples, the estimation of a medical premonitory event may take the form of a probability of the event occurring. FIG. 51 is a flow chart of a method that may be implemented by any medical device or medical support device at the location of a patient, such as, for example, a monitor/defibrillator, automated external defibrillator (AED), or a wearable medical device, such as a LifeVest® wearable cardioverter defibrillator. In stage 5110, the medical device or the medical support device monitors one or more parameters of a subject. The one or more parameters may be predictive of an oncoming cardiac event and/or may be used to calculate an event estimation of risk score for a medical event of the subject. The one or more parameters may include one or more parameters associated with the subject's ECG or electroencephalography ("EEG"), the heart rate or change in heart rate of the subject, blood pressure of the subject, tidal CO2, SpO2, SMO2, cerebral blood flow, brain oxygen level, tissue pH, reaction of the subject's heart to tilting of the subject, and/or ultrasound images of the subject's heart. In stage 5120, the parameters are analyzed by a control unit of the medical device or medical support device, for example, to calculate an event estimation of risk score or to determine if there is a high likelihood of an impending cardiac event and/or if a cardiac event is occurring.

The event estimation of risk score may be calculated in a variety of different ways. For example, the event estimation of risk score may be calculated based on one or more measured physiological parameters of the subject, for example, one or more parameters associated with the subject's ECG or EEG, blood pressure, heart rate or change in heart rate, tidal CO2, SpO2, SMO2, cerebral blood flow, brain oxygen level, tissue pH, reaction of the subject's heart to tilting of the subject, and/or ultrasound images of the subject's heart.

Machine learning processes may be used along with the above-mentioned parameters and/or historical data about the subject to calculate the event estimation of risk score. For instance, in one example, a machine learning classifier is trained on training metrics comprising at least one of cardiac electrophysiology metrics (e.g., as enumerated above) of a plurality of subjects and at least one of demographic metrics and medical history metrics of the plurality of subjects. In some implementations, the machine learning classifier can be trained on a large population, for example, a population that can range from several thousand to tens of thousands of patient records comprising electrophysiology, demographic, and medical history information. The machine learning tool can include but is not limited to classification and regression tree decision models, such as random forest and gradient boosting, (e.g., implemented using R or any other statistical/mathematical programming language). Any other classification based machine learning tool can be used, including neural networks and support vector machines.

Because the machine learning tool may be computationally intensive, some or all of the processing for the machine learning tool may be performed on a server that is separate from a device (e.g., the mobile computing device 102 of FIG. 1). Decision thresholds of the classifier may be trained using machine learning. For example, the classifier may be a random forest classifier that uses a number of decision trees, in order to improve the classification rate. Decision tree learning is a method commonly used in data mining to create a model that predicts the value of a target variable based on several input variables. Each interior node in a decision tree corresponds to one of the input variables and each leaf represents a value of the target variable given the values of the input variables represented by the path from the root to the leaf. A decision tree thus provides a simple representation for classifying examples and is one of the most successful techniques for supervised classification learning.

If the control unit determines in stage 5130 that there is no cardiac event occurring and that there is not a high likelihood of an impending cardiac event, e.g., the event estimation of risk score is below a threshold, then the device returns to stage 5110 to monitor the parameters of the subject. In some embodiments, different parameters of the subject may be monitored at different times, for example, sequentially.

If, in stage 5130, the control unit determines a cardiac event is occurring or that there is a high likelihood of an impending cardiac event, the control determines in stage 5140 whether the cardiac event is treatable, for example, whether an intervention may be effective to treat the cardiac event or to reduce the chance or severity of the impending cardiac event. If it is determined by the control unit in stage 5140 that the type of cardiac event the subject is experiencing cannot currently be treated by any intervention available to the medical device or by a first responder or if no intervention available to the medical device or to a first responder is currently capable of reducing the chance or severity of the impending cardiac event, the device may advise in stage 5150 that the subject be transported to a facility, for example, a hospital for treatment and/or monitoring, and the device returns to stage 5110 to monitor the parameters of the subject. The parameters of the subject may be recorded so that if the subject reaches a hospital or another source of treatment, which may have capabilities beyond that of the medical device, the history of the subject may be reviewed to determine an appropriate treatment.

If, in stage 5140, the control unit determines that the cardiac event that is occurring may be treated by an intervention available to the medical device or a first responder or that an intervention available to the medical device or first responder is capable of reducing the chance or severity of an impending cardiac event, the device, in stage 5160, makes a determination of an available action (e.g., intervention) to provide to the subject. In some implementations, the device considers multiple potential interventions, but may provide the best type of available intervention to the subject.

In stage 5170, the device performs or indicates the determined intervention, for example, by administering automated chest compressions, defibrillation, and/or automated drug delivery. If the selected intervention is one that the device cannot perform on its own, the device may provide an indication to a first responder, for example, through a display or a speaker of what intervention to administer to the subject or communicate the recommended treatment to another type of life support device that is capable of performing the recommended intervention.

In some examples, the detection and estimation of medical premonitory events may take the form of an early warning score (EWS), such as the Modified Early Warning Score (MEWS) or National Early Warning Score (NEWS). An EWS is a guide used by medical services to quickly and accurately determine the degree of illness of a patient. It is typically based on the vital signs (respiratory rate, oxygen saturation, temperature, blood pressure, pulse/heart rate, AVPU response). EWSs were developed in the late 1990s when studies showed that in-hospital deterioration and cardiac arrest was often preceded by a period of increasing abnormalities in the vital signs. In some examples, the event log application is configured to provide screens with controls to receive inputs such as Early Warning Score (EWS) factors or other demographic patient clinical information as well as physiologic data used for calculating an EWS or other MPE estimation as well as display EWS or MPE estimations.

In certain examples, the event log application is further configured to provide screens that include a control that responds to input selecting the control by calling an RRT or code team to, for example, the location of the mobile computing device. In some examples, if either the EWS or MPE estimation value exceeds a threshold, the event log application may trigger an alarm. In one example, the alarm may be on the mobile computing device locally; in another example, the alarm may be generated via a communication from the event log application to a server that, in turn, sends out an alarm to one or more remote devices also in communication with the server. The remote devices may be a watch, phone, tablet, central station monitor, etc. The alarm on the remote device may cause the remote device to sound an audible voice prompt, a tactile haptic vibration or annunciation and to display where the patient is located, what the EWS or MPE estimation is, along with pertinent patient information such as name, age, room number, other demographic information, pertinent vital signs such as SpO2, respiration, heart rate, etc. Other information such as caregiver information may also be provided, for example, caregiver identity, level of medical expertise/training, shift under which the caregiver is working, time at which the caregiver arrived at the patient, amongst others. It may be more expedient for such information to be automatically provided so that manual entry is not required. There may further be a control on the remote device that responds to the alarm, indicating to the event log application on the device at the patient that an RRT team or team member is en route.

In some examples, the event log application is configured to receive event logs from other source devices involved in the emergency medical treatment of the patient and merge those event logs with its event log to create a consolidated event log as part of an overall summary of the event. In these examples, the event log application is further configured to provide a representation of the consolidated event log to a healthcare provider via a screen and associated set of controls. The event log application is configured to enable different types of interactions with consolidated event log entries depending on the source of each entry. For instance, where the source of an event log entry is the event log application, the event log application can allow editing and/or deleting of the event log entry in response to receiving input selecting its associated control. In another example, where the source of an event log entry is a source other than the event log application (e.g., a medical device used to treat the patient during the emergency medical treatment that automatically records event log entries such as the detection of a shockable rhythm and the administration of a defibrillation shock), the event log application can disable the control associated with the entry, thereby preventing it from being edited or deleted from the patient record. Additionally or alternatively, the event log application can respond to selection of the control associated with the entry with an indication of the selection but without providing any mechanism to edit or delete the entry. In still another example, the event log application can respond to selection of the control associated with the entry with a request for confirmation before allowing the entry to be edited or deleted. These restrictions on editing or deleting entries enable the systems and methods described therein to maintain the integrity of the record, where more than one source is available. This represents an improvement over other systems and methods.

In some examples, the event log application is configured to identify a source device (e.g., medical device, defibrillator, patient monitor), via a proximity-based detection process. For instance, in some examples, the event log application is configured to identify a source device via an image acquired by a camera of the mobile computing device. In these examples, the event log application may scan the image for a QR code or barcode that identifies the source device and that is affixed or displayed by the source device. In certain examples, the event log application is configured to identify a source device via a near-field communication (NFC) tag or a radio frequency identification (RFID) tag. In these examples, both the medical device and the mobile computing device may include NFC or RFID tags that correspond to, and are detectable by, one another. This detection may occur, for example, when the corresponding tags come within 10 cm of one another. Once the source device is identified, then the event log application may be able to access records generated by the source device, either directly from the source device or from another computing device which has stored thereon the generated records from the source device.

In some examples, the event log application is configured to apply the image and radio frequency-based identification techniques described above to identify a patient based on a component (e.g. QR code, barcode, NFC tag, RFID tag, etc.) attached to the patient. In some examples, the component may be included in a label, wrist band, article of clothing or other wearable item associated with the patient. Similarly with respect to accessing of records from the source device, when the patient is identified, the event log application may be able to access relevant patient information, for example, from another computing device that has stored thereon a patient record having the relevant patient information (e.g., an EHR system). Further, the event log application can, in some examples, initiate provision selected portions of the event log to an EHR system via one or more EHR APIs, such as those provided by Allscripts, AthenaHealth, and eClinicalWorks, amongst others. For instance, in some examples, the event log application can transmit a provision request to the event log API that causes the event log API to provide the selected portions of the event log to the EHR system via the appropriate EHR API. Alternatively or additionally, the event log application can transmit the selected portions of the event log directly to the EHR system via the appropriate EHR API.

In some examples, the event log application is configured to establish a communication connection with a source device identified via the proximity-based detection process. In these examples, the event log application is configured to exchange data, such as event logs and metadata descriptive of the event logs, with the source device via the communication connection. In some examples, the event log application is also configured to identify the patient being treated via patient identification information stored within the event log transferred from the source device.

In some examples, the event log application is configured to interoperate, via a communication connection, with an event log application program interface (API) that is executed by a separate computing device (e.g., a server). The server and event log API are described further below. As with the communicative connection described above, the event log application is configured to exchange a variety of data (e.g., event logs and metadata descriptive of the event logs) with the event log API via the communication connection between it and the event log API.

In some examples, the systems and methods described herein include medical devices (e.g., defibrillators) that are configured to acquire and/or calculate a variety of information, such as identification information and/or physiologic information for a patient undergoing emergency treatment and CPR quality metrics. Examples of patient identification information include name, social security number, EHR identification number, and the like. Examples of patient physiologic information include heart rate, respiration rate, blood pressure, ECG waveform, oxygen saturation, and the like. In these examples, the medical devices store this information within an event log. Further, in these examples, the medical devices are configured to transmit event logs that they generate to either the event log application or a separate server for subsequent processing and consolidation.

In some examples, the systems and methods described herein include the separate server. In these examples, the server executes an event log API to process event logs generated by the event log application and/or other sources devices. More specifically, in these examples, the event log API is configured to receive, parse, store, retrieve, and transmit copies of event logs. For instance, in one example, the event log API stores event logs within an event log data store implemented locally to the server. In some examples, the event log API monitors for requests originated and transmitted by the event log application and/or the source devices. Additionally or alternatively, in some examples, the event log API originates and transmits requests to the event log application and/or the source devices to execute the processes described herein.

In some examples, the systems and method described herein include a computing device separate from the mobile computing device, the other source devices, and the server. In these examples, the computing device is configured to interoperate with the event log API to retrieve and display consolidated event logs to another healthcare provider. Further, in these examples, the computing device is configured to retrieve and display reports including a variety of metrics calculated either by the medical device or the event log API.

In at least one example, an overall system for providing documentation of emergency medical events is provided. The system includes a mobile computing device with a user interface and one or more processors. The user interface can include a touchscreen. The one or more processors and memory of the mobile computing device is configured to receive input from a healthcare provider while a patient is being treated by a team including the healthcare provider. The team can be, for example, a rapid response team or a code team. The input can indicate events that occur during the treatment. In response to receiving the input, the mobile computing device can generate an event log of time-stamped log entries that mark or document the events.

In some examples, the mobile computing device includes a network interface configured to establish communicative connections with a network. This network can include one or more other devices, such as medical devices and remote servers. These other devices can store other event logs of time-stamped log entries that mark or document the events that occur during the treatment, and thus provide additional points of view of the treatment. The mobile computing device can retrieve these other event logs and consolidate them with its own event log. The mobile computing device can present events from this consolidated event log to the healthcare provider via the user interface.

In some examples, the mobile computing device is configured to present each time-stamped log entry in an event log (consolidated or single-sourced) within a corresponding control within the user interface. The mobile computing device can enable various types of interactions via these controls. For instance, the user interface can restrict editing of entries produced by devices other than the mobile device. These restrictions can be implemented by disabling controls, partially disabling controls to receive input but not store modifications in their corresponding time-stamped log entries or prompting for confirmation of changes to time-stamped log entries.

In some examples, the other devices that can store event logs of time-stamped log entries include medical devices and remote servers. These other devices can establish networks and communicative connections with the mobile computing device. A medical device can obtain physiological information from the patient, store the physiological information within the time-stamped log entries, and transmit the time-stamped log entries to other devices connected to the network, such as the remote server and the mobile computing device. The medical device can be a defibrillator. A remote server can store patient identification information. The remote server can also store chest compression and/or ventilation quality metrics. These chest compression quality metrics can include a percentage of compressions that fall within a target depth, a percentage of compressions that fall within a target rate, an average depth of compressions, and an average rate of compressions. The ventilation quality metrics may include a percentage of ventilations that fall with a target tidal volume, an amount/percentage of ventilations that fall within a target ventilation rate, an average tidal volume, and an average ventilation rate. The remote server can include a network interface through which it can access time-stamped log entries stored on the mobile computing device or the medical device. The remote server can provide, via an additional user interface, events corresponding to the time-stamped log entries. Further the remote server can provide the various types of interactions described above via the additional user interface.

In some examples, the mobile computing device is configured to establish network connections with other devices where the mobile computing device determines that the other devices are in close proximity to the mobile computing device. For instance, using this proximity-based detection the mobile computing device can identify and establish communicative connections with the medical device. The mobile computing device can perform proximity-based detection using a sensor included in the mobile computing device. This sensor can detect a medical device where the medical device is within 10 cm of the sensor. The sensor can include a camera, NFC tag, or an RFID tag. Where the sensor is a camera, the medical device can include a barcode or QR code. Where the sensor is an NFC tag, the medical device can include a corresponding NFC tag. Where the sensor is an RFID tag, the medical device can include a corresponding RFID tag.

In some examples using proximity-based detection, the mobile computing device is configured to identify the patient being treated. The mobile computing device can select the identified patient by using a proximity-based detection to access, via a communicative connection, the patient identification information stored on the medical device. The proximity-based detection used to select the identified patient can be provided for by a patient identification component, such as badge, label, wristband, article of clothing or other wearable item associated with the patient. The mobile computing device can include a sensor configured to identify the patient identification component. This sensor can include a camera, NFC tag, or an RFID tag. Where the sensor is a camera, the patient identification component can include a barcode or QR code. Where the sensor is an NFC tag, the patient identification component can include a corresponding NFC tag. Where the sensor is an RFID tag, the patient identification component can include a corresponding RFID tag.

In some examples, the mobile computing device is configured to access, via the communicative connection, patient identification information and chest compression and/or ventilation quality metrics stored on other devices (e.g., a medical device, a remote server, etc.) connected to the network. The mobile computing device can present patient identification information via the user interface. The mobile computing device can present a summary of chest compression and/or ventilation quality metrics via the user interface.

In some examples, the mobile computing device can be configured to operation in a first documentation mode or a second documentation mode. These documentation modes can be specific to patient characteristics, such as the age of the patient or size of the patient. For instance, in one example, the mobile computing device can be configured to operate in a pediatric mode or an adult mode. The pediatric mode can be selected for patients under 8 years old. The adult mode can be selected for patients 8 years old and older. In certain embodiments, a neonatal mode (e.g., for patients less than 4-6 weeks old) may also be employed. When operating in the pediatric mode, the mobile computing device tailors its user interface to ease the selection of pediatric-specific input options for log entries and parameters. When operating in the adult mode, the mobile computing device tailors its user interface to ease the selection of adult-specific input options for log entries and parameters. These pediatric-specific (and optionally neonatal-specific) and adult-specific input options can specify, for example, intubation tube sizes, CPR compression techniques, drug contraindications (e.g., in the form of a warning marker for certain drug contraindications) and/or drug dosages. For neonatal mode, the chest compression technique selections may include encircling hands and two-finger techniques. The mobile computing device is configured to display an option, via the user interface, to enable a healthcare provider to select either mode. With respect to size, a measurement of patient chest size may be input into the mobile computing device, and certain parameters such as the target compression depth and recommended compression technique may be adjusted. For example, for a smaller chest size, the target compression depth may decrease, and for a larger chest size, the target compression depth may increase; or the suggested compression technique may change to encircling hands. A height measurement may be input into the mobile computing device, and a target ventilation tidal volume may be appropriately adjusted. For example, an input of a taller height may result in the target ventilation tidal volume increasing, or conversely an input of a shorter height may result in the target ventilation tidal volume decreasing.

In some examples, the mobile computing device is configured to display an electrotherapy timer on the user interface. The electrotherapy timer can indicate a documented time elapsed since electrotherapy was administered to the patient. The mobile computing device can display a documented indication of how many times electrotherapy has been administered to the patient. The time-stamped log entries generated by mobile computing device can include an electrotherapy entry indicating a documented time that electrotherapy has been administered to the patient.

In some examples, the mobile computing device is configured to display a CPR timer on the user interface. The CPR timer can indicate a documented time elapsed since chest compressions were initiated. The CPR timer can provide a notification after 2 minutes have elapsed since chest compressions were initiated. The notification can include flashing, highlighting, and/or changing color of the CPR timer.

In some examples, the mobile computing device is configured to display a CPR idle timer on the user interface. The CPR idle timer can indicate a documented time elapsed since chest compressions were paused. The CPR idle timer can provide a notification after 10 seconds have elapsed since chest compressions were paused. The notification can include flashing, highlighting, and/or changing color of the CPR idle timer.

In some examples, the mobile computing device is configured to display a drug or medication timer on the user interface. The drug timer can indicate a documented time elapsed since the drug was last administered. The drug timer can provide a notification after 3 minutes have elapsed since chest compressions were paused. The notification can include flashing, highlighting, and/or changing color of the drug timer.

In some examples, the mobile computing device is configured to display a documented indication of the number of times chest compressions have been initiated and paused. The mobile computing device can record a CPR entry indicating a documented time that chest compressions were initiated. In some examples, the mobile computing device is configured to display a documented indication of the number of times a drug has been administered. The mobile computing device can record a drug entry indicating a documented time that a drug was administered.

In some examples, the mobile computing device is configured to display one or more screen with controls that enable calculation and display of a MEWS for a patient. These controls can receive input from a healthcare provider to record measurements and/or assessments of MEWS factors. These controls can include a heart rate control, a respiratory control, a blood pressure control, a body temperature control, a urine production control, and a neurologic state control. These screens can further include notification controls that enable a healthcare provider to summon a rapid response team or a code team to the location of the patient at the push of a button. The mobile computing device is configured to transmit a notification to either a device associated with a rapid response team member or a code team member in response to receiving a selection of the corresponding control.

Emergency Care Documentation System

FIG. 1 illustrates an example of a distributed system 100 of components configured to record emergency care. As shown in FIG. 1, the distributed system 100 includes a mobile computing device 102, a medical device 104, a computing device 106, and a server 108 that are configured to communicatively couple with one another directly or indirectly via, for example, a network 110. The mobile computing device 102 is associated with and used by a healthcare provider 112. The mobile computing device 102 includes and implements an event log application 120 that is programmed to generate an event log 122 via, for example, user input that documents care provided to a patient 118. The medical device 104 is associated with a healthcare provider 114 and the patient 118. The medical device 104 is configured to monitor and/or treat the patient 118 and is programmed to generate an event log 124, automatically generated or via user input, that documents the monitoring and/or treatment provided to the patient 118 via the medical device 104. The computing device 106 is associated with and used by a healthcare provider 116. The computing device 106 includes and implements a log analysis application 130 that is programmed to access and display a view 132, and metrics descriptive thereof, to the healthcare provider 116. The server 108 includes and implements an event log API 128 and an event log data store 126 that are configured to receive and store event logs that have originated from the mobile computing device 102 and the medical device 104. In some examples, the event log API 128 is further configured to analyze the event log data store 126 to generate the metrics characterizing the view 132 for display by the log analysis application 130. In some examples, the medical device 104, the server 108, and/or the mobile computing device 102 (and their various components) communicate with one another in real time, thereby enable rapid information exchange and event log consolidation while the patient 118 is being monitored and/or treated. Thus, for example, the mobile computing device 102 and/or the server 108 may receive log entries generated from the medical device 104 while the emergency medical event is happening, so that a user of the mobile computing device 102 and/or server 108 is able to see events unfold in real-time. Each of the components of the distributed system 100 illustrated in FIG. 1 is described further below in detail. In addition, various configurations of the distributed system 100 are described further below, for example with reference to FIGS. 2, 29, and 38.

The mobile computing device 102 can include any of a variety of portable computing platforms such as smart phones and/or tablet computers. Particular examples of the mobile computing device 102 are described further below with reference to FIG. 48. Regardless of its particular form factor or constituent components, as shown in FIG. 1, the mobile computing device 102 is configured to implement the event log application 120. The event log application 120, in turn, is configured to generate the event log 122 by interacting with (e.g., receiving input from and/or providing output to) the healthcare provider 112. For example, during operation the event log application 120 interacts with the healthcare provider 112 to document, within the event log 122, care provided to the patient 118. This documentation can describe monitoring and/or treatment provided by the healthcare provider 114 and/or the medical device 104 to the patient 118. As shown in FIG. 1, the event log 122 includes any number of entries 1 through X.

In some examples, the event log application 120 is configured to document a wide variety of events. For instance, in an example in which the healthcare provider 114 runs a code to resuscitate the patient 118, the events documented by the event log application 120 can include CPR administration, delivery of therapeutic electric pulses, provision of medication, occurrence of particular ECG rhythms, return of spontaneous circulation (ROSC), patient vitals information, procedures administered to the patient (e.g., placement of an intubation tube), amongst others. Various types of recordable events including but not limited to those discussed above are described further below. To record certain events, the event log application 120 is configured to provide various screens to the healthcare provider 112. Each screen provided by the event log application 120 includes one or more user interface controls that are configured to receive input data and/or display output data. The event log application 120 is configured to receive input selecting the user interface controls and to execute, in response to receiving a selection of any given control, a process associated with the control. Many of the screens and controls described herein implement innovative features that increase the efficiency of the healthcare provider 112 in documenting emergency care vis-à-vis the state of the art. Examples of some of these screens are described further below with reference to FIGS. 5, 7, 9-17, 19, 21-24, 26-28, 45, and 46.

In some examples, the event log application 120 is configured to exchange event log entries with the medical device 104 and/or the server 108 in real time (e.g., while the patient 118 is undergoing treatment). As such, in some examples, the event log application is able to compile a consolidated event log that includes entries from event logs generated by the event log application and other source devices (e.g., the medical device 104). In some examples, this consolidated event log can be used by the event log application to pre-populate event log entries that can be omitted and/or confirmed by the healthcare provider 112, thereby increasing both the speed and accuracy of healthcare provider 112 in documenting patient treatment. Examples of event log entries and parameters that can be collected in this way include CPR start time (e.g., chest compression start time, ventilation start time), shock time, shock energy, and shock count. Moreover, by acting as central hub of information from all devices involved in treating the patient—while the treatment is ongoing—the event log application informs the healthcare provider's 112 approach to treating the patient 118 and/or directing other healthcare providers (e.g., the healthcare provider 114) in treating the patient 118. This can improve the efficacy of the treatment and improve patient outcomes.

For example, where the event log application 120 is configured for real time exchange of event logs, nurses in an intensive care unit can respond immediately to a patient suffering from cardiac arrest using the medical equipment they have available (e.g. a defibrillator). This treatment can begin prior to arrival of the code team. Where one of the members of the code team has a mobile computing device with the event log application 120 installed, the code team can review the log entries generated by the defibrillator while the code team is en route. These entries can denote the CPR start time/end time, number of shocks delivered, CPR type (e.g., manual chest compressions, manual ventilations, automated compressions via an automated chest compressor, automated ventilations via a ventilation device, etc.), overall location within the CPR protocol, type of rhythm (e.g., shockable or non-shockable), etc., thus informing the code team as to the next action to take upon arrival.

In some examples, the event log application 120 is further configured to enable the healthcare provider 112 to close an event log by performing a number of end log activities. Examples of these end log activities include viewing the consolidated event log generated by the event log application and/or other sources (e.g., medical device(s)), editing previously recorded events, adding additional events or other information germane to the event log, and/or uploading the event log to the event log data store 126 via the network 110 and the event log API 128. In some examples, the event log application 120 is configured to provide screens to the healthcare provider 112 that enable the healthcare provider 112 to review events, edit events, delete events, and/or to enter other information germane to the event log. In certain examples, these screens advantageously enable modification of some entries and prevent modification of other entries. Examples of these screen and others are described further below with reference to FIGS. 19 and 25-28.

To enable the healthcare provider 112 to access log entries from sources other than the event log application 120, some examples of the event log application 120 connect to the medical device 104 and/or to the event log data store 126 to identify and retrieve event logs created by other source devices (e.g., the event log 124 generated by the medical device 104). In these examples, the event log application 120 is configured to initiate communicative connections to the server 108 and/or the medical device 104. Certain examples of screens and processes related to initiation and utilization of these connections are described further below with reference to FIGS. 20-24. Additionally or alternatively, some examples of the event log application 120 upload event logs to the event log data store 126. Examples of processes and screens related to uploading event logs are described further below with reference to FIGS. 6 and 7.

In some examples, the event log application 120 is further configured to provide the healthcare provider 112 with additional functionality related to code blue and other emergency events. For instance, in at least one example, the event log application 120 is configured to enable the healthcare provider 112 to call a code team to run a code for the patient 118 and/or a rapid response team to provide the patient with urgent care. A screen that the event log application 120 is configured to provide in these examples is described further below with reference to FIG. 45.

In some examples, mobile computing device 102 is an early warning system designed to estimate the risk of a patient undergoing acute physiologic deterioration and detect medical premonitory events. The early warning system may be implemented as the calculation and display of a modified early warning score (MEWS). A modified early warning score (MEWS) is a simple guide used by medical personnel to quickly determine the risk of death of a subject. It is based on data derived from four physiological readings (systolic blood pressure, heart rate, respiratory rate, body temperature) and one observation (level of consciousness). The resulting observations are compared to a normal range to generate a single score. In some examples, the event log application 120 is configured to generate an estimate of the risk of the patient 118 undergoing acute physiologic deterioration, which may include a MEWS for the patient 118. Screens that the event log application 120 is configured to provide in these examples are described further below with reference to FIGS. 45 and 46.

Returning to FIG. 1, the computing device 106 can include any of a variety of computing platforms, either stationary or mobile, that include memory, or some other form of data storage, and a processor coupled to the memory to manipulate data stored in the memory. Regardless of its particular form factor or constituent components, as shown in FIG. 1, the computing device 106 is configured to implement the log analysis application 130. The log analysis application 130, in turn, is configured to process an event log that includes entries generated by the event log application 120 and/or the medical device 104. In some examples, the log analysis application 130 is further configured to present metrics and other analysis of event logs to the healthcare provider 116. In some examples, the log analysis application 130 is configured to present these metrics and analysis to the healthcare provider 116 via one or more screens. Some examples of these screens are described further below with reference to FIGS. 32-37.

As shown in FIG. 1, the medical device 104 can include one or more of several types of medical devices, such as the medical devices described further below with reference to FIGS. 49 and 50. For instance the medical device 104 can include a defibrillator. Regardless of its particular configuration, as shown in FIG. 1, the medical device 104 is configured to generate the event log 124 during monitoring and/or treatment of the patient 118. In some examples, the medical device 104 begins recording events upon power-up and, therefore, the event log 124 may include events that occur before, during, and/or after the healthcare provider 114 performs activities in monitoring and/or treating the patient 118 with, or without, the medical device 104.

In some examples illustrated by FIG. 1, the medical device 104 includes a network interface configured to communicate with the network 110 via one or more standards supported by the network 110. Alternatively or additionally, in some examples, the network interface of the medical device 104 is configured to communicate directly with the mobile computing device 102 via a proximal connection. These proximal connections can be implemented via any of a variety of wired and/or wireless standards, such as Universal Serial Bus (USB), BLUETOOTH and/or NFC standards, RFID, among others. Processes executed by the medical device 104, in conjunction with the mobile computing device 102, to establish and utilize proximal connections are described further below with reference to FIGS. 39 and 40.

As illustrated in FIG. 1, the server 108 can include one or more physical and/or virtual servers configured to implement the event log data store 126 and the event log API 128. In some examples, the event log API 128 is configured to receive, process, and respond to commands issued by a client process, such as the event log application 120 and/or the log analysis application 130. The event log API 128 can be implemented using a variety of interoperability standards and architectural styles. For instance, in one example, the event log API 128 is a web services interface implemented using a representational state transfer (REST) architectural style. In this example, the event log API communicates with a client process using Hypertext Transfer Protocol (HTTP) along with JavaScript Object Notation and/or extensible markup language. In some examples, portions of the HTTP communications may be encrypted to increase security. Alternatively or additionally, in some examples, the event log API 128 is implemented as a NET web API that responses to HTTP posts to particular uniform resource locators with data descriptive of the event logs stored in the event log data store 126. Alternatively or additionally, in some examples, the event log API 128 is implemented using simple file transfer protocol commands and/or a proprietary application protocol accessible via a transmission control protocol socket. Thus, event log API 128 as described herein is not limited to a particular implementation.

In some examples, the event log API 128 includes a plurality of endpoints to enable reliable system performance. For instance, in at least one example, the event log API 128 includes a one or more first endpoints to receive and process requests for data previously stored in the event log data store 126 and one or more second endpoints to receive and process requests to store new event log data within the event log data store 126. This segmentation ensures that requests for data already stored in the event log data store 126 can be quickly serviced, and is necessary because requests to upload event logs, parse the event logs, and store the resulting event log data in the event log data store 126 can require more processing time and resources. The types of information parsed from the event logs and stored in the event log data store 126 can include, for example, CPR compression data, CPR ventilation data, patient physiologic parameters, documented events, and the like.

In at least one example, the event log API 128 includes processing components that can be executed periodically or on-demand (e.g., when new event logs are received from the medical device 124 and/or the mobile computing device 102) to calculate metrics and generate reports descriptive of the event logs stored in the event log data store 126. The metrics and reports created by these processing components may include those described further below with reference to FIGS. 32-37. The metrics and reports can further include report rendered in PDF format and/or event log timelines rendered in CSV format. In some examples, the processing components are implemented as a combination of SQL stored procedures and natively executable data objects compiled using a C++ compiler or some other compiler capable of generating natively executable code from a high-level programming language. Examples of the metrics that these processing components can calculate include arrest survival percentages, CPR compression and/or ventilation quality percentages and averages, survival to discharge percentages, and average post-shock pauses for specific periods of time, amongst others. Moreover, in some examples, the processing components can filter the data used to calculate the metrics to include, or omit, data based on dimensions such as patient age group, whether the event treated was witnessed, the discharge status of the patient, and the location of the event.

In certain examples depicted by FIG. 1, the event log data store 126 is configured to store event log entries from various source devices, such as the mobile computing device 102 and the medical device 104. The event log data store 126 may be organized according to a variety of physical and/or logical structures. In at least one example, the event log data store 126 is implemented within a relational database having a highly normalized schema and accessible via a structured query language (SQL) engine, such as ORACLE or SQL-SERVER. In some examples, at least portions of the event log data store 126 are implemented as flat operating system files including serialized, proprietary data structures. Thus, the event log data store 126 as described herein is not limited to a particular implementation.

In at least one example, the event log data store 126 is organized into a set of relational database tables that includes an event log table and a log entries table. In this example, the event log table includes rows of data that are each descriptive of a treatment intervention documented in the event log database. Thus, each row in the event log table includes fields configured to store a unique identifier of the event log and metadata descriptive of the intervention documented by the event log (e.g., patient identification information that uniquely identifies the patient, healthcare providers involved in the intervention, reason(s) the intervention ended and its outcome, unique identifiers of medical devices and supplies used in the intervention, the patient treated during the intervention, and overall issues encountered during execution of the intervention. Continuing with this example, the log entries table includes rows of data that are each descriptive of an entry within an event log. Thus, each row in the log entries table includes fields configured to store a unique identifier of the event log to which the entry belongs, a field that uniquely identifies the entry among the entries belonging to the event log, a date/time stamp of the entry, a unique identifier of the source device (e.g., a particular medical device or a particular mobile computing device) of the entry, a field that identifies (via a type identifier or textual information) an event documented by the log entry, and one or more fields that store values and/or parameters associated with the entry.

In some examples in accord with FIG. 1, the network 110 may include any communication network through which the mobile computing device 102, the medical device 104, the computing device 106, and the server 108 can exchange data. In some examples, the network 110 includes and supports wireless network and/or wired connections. For instance, in these examples, the network 110 can support one or more networking standards such as GSM, CMDA, USB, BLUETOOTH, CAN, ZigBee, Wireless Ethernet, Ethernet, and TCP/IP, among others. In at least one example, the network 110 includes both private networks, such as local area networks, and public networks, such as the Internet. It should be noted that, in some examples, the network 110 include one or more intermediate devices involved in the routing of packets from one endpoint to another. However, in other examples, the network 110 involves only two endpoints that each have a network connection directly with the other. One example of such a network is illustrated below with reference to FIG. 38.

As shown in FIG. 1, the healthcare providers 112, 114, and 116 are distinct individuals, However, the examples disclosed herein are not limited to use by a particular number or configuration of healthcare providers. For instance, in at least one example, a single healthcare provider runs a cardiac resuscitation code for the patient 118 using the medical device 104 and documents the code using the mobile computing device 102. In this example, the same healthcare provider (or a different healthcare provider) accesses the log analysis application 130 to review and evaluate the code and/or other codes stored in the event log data store 126. Thus, the examples disclosed herein are not limited to a particular configuration of healthcare providers and/or patients.

Similarly, although the mobile computing device 102, the medical device 104, the computing device 106, and the server 108 are illustrated as distinct devices in FIG. 1, the examples disclosed herein are not so limited. For instance, in some examples, a single mobile computing device (e.g., a tablet computer) acts as both the mobile computing device 102 and the computing device 106. Additionally or alternatively, in certain examples, a single computing device acts as both the computing device 106 and the server 108. Moreover, in some examples, a single medical device acts, or multiple medical devices collectively act, as both the medical device 104 and the mobile computing device 102. Thus, the examples disclosed herein are not limited to a particular device configuration and are capable of assuming a wide variety of system layouts in accordance with the principles described herein.

Client-Side Log Consolidation

Figure 2:
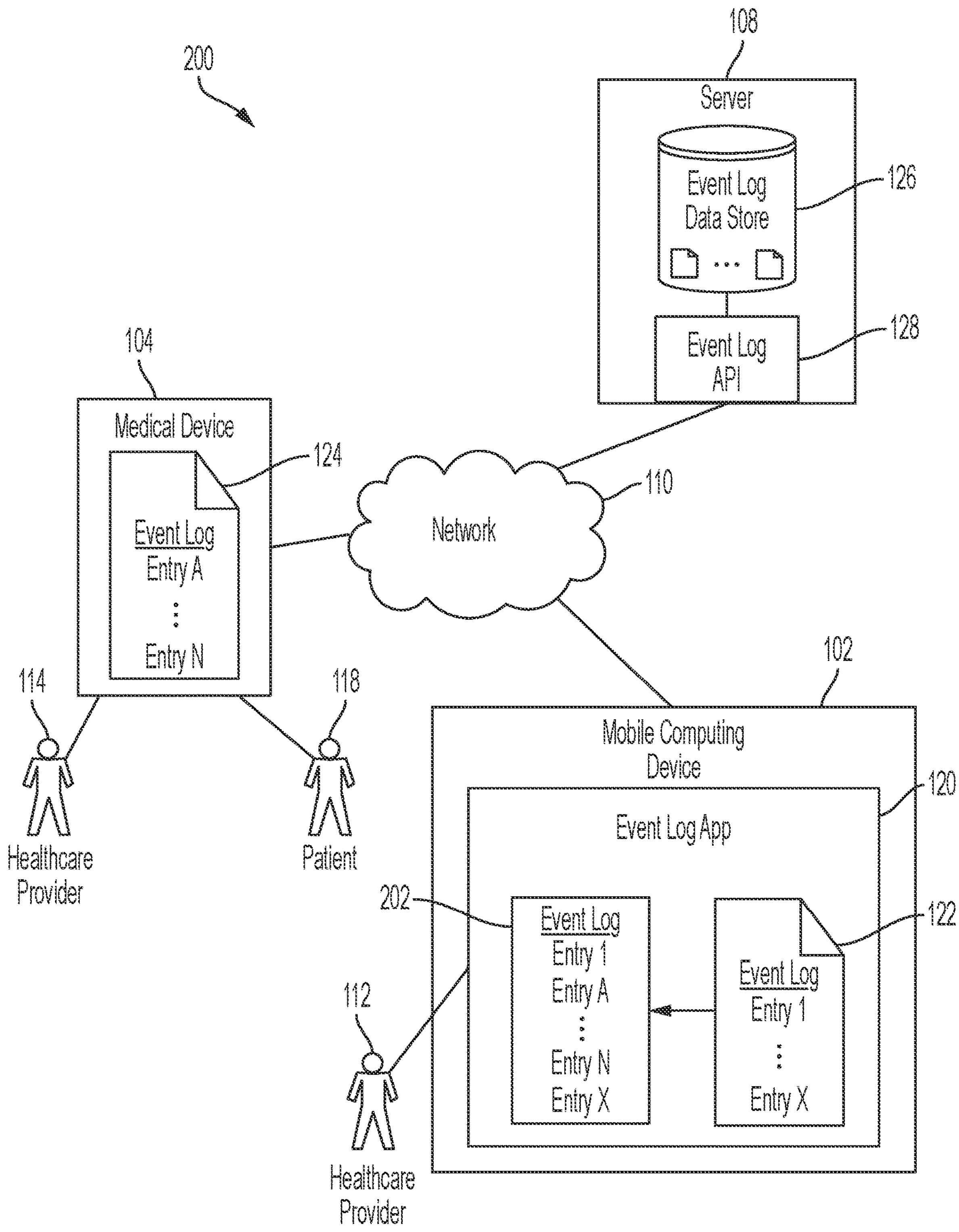
FIG. 2 is a block diagram illustrating a particular configuration of the distributed system of FIG. 1 in accordance with at least one example disclosed herein.

FIG. 2 illustrates a particular configuration 200 of the distributed system 100 in which the event log application 120 is configured to interoperate with the event log API 128 to provide a view 202. In this example, the view 202 displays an event log with entries consolidated from multiple source devices. As shown in FIG. 2, the configuration 200 includes the mobile computing device 102, the medical device 104, the server 108, and the network 110. In operation, the configuration 200 can be used by the healthcare provider 112 to document care provided to the patient 118 by the healthcare provider 114 and/or the medical device 104.

As shown in FIG. 2, the event log application is configured to provide, via the view 202, a consolidated event log that includes entries from the event log 122 and entries from the event log 124. In other words, the view 202 presents a unified perspective of patient treatment that integrates entries from multiple source devices. In this way, the configuration 200 provides a single, holistic view of emergency care that manifests continuity of record. This feature is advantageous vis-a-vis systems that require users to compile documentation of treatment from distinct sources.

In some examples, the event log application 120 is configured to render the view 202 from a consolidated event log that is stored locally on the mobile computing device 102. Alternatively or additionally, in some examples, the event log application 120 is configured to render the view 202 from a consolidated event log that is stored, in part or in whole, locally on the mobile computing device 102 and/or within the event log data store 126. Regardless of the storage location of the consolidated event log, within the configuration 200, both the medical device 104 and the mobile computing device 102 interoperate with the server 108 via the network 110 to enable the event log application 120 to provide the healthcare provider 112 with the view 202. As such, the mobile computing device 102, the medical device 104, and the server 108 each include a network interface that is configured to exchange data with the network 110 via communication standards supported by the network 110. In at least one example, the network interfaces of the mobile computing device 102 and the medical device 104 are configured to exchange data with the network 110 via a WiFi connection, and the network interface of the server 108 is configured to exchange data with the network via a wired ethernet connection. In addition, within the configuration 200, the medical device 104 and the event log application 120 are configured to interoperate with the event log API 128 (via, e.g., requests and responses) to exchange event logs 124 and 122 and metadata regarding the event logs 124 and 122. One example of the processes executed by the configuration 200 to provide the healthcare provider 112 with the view 202 will now be described with reference to FIG. 3.

Figure 3:
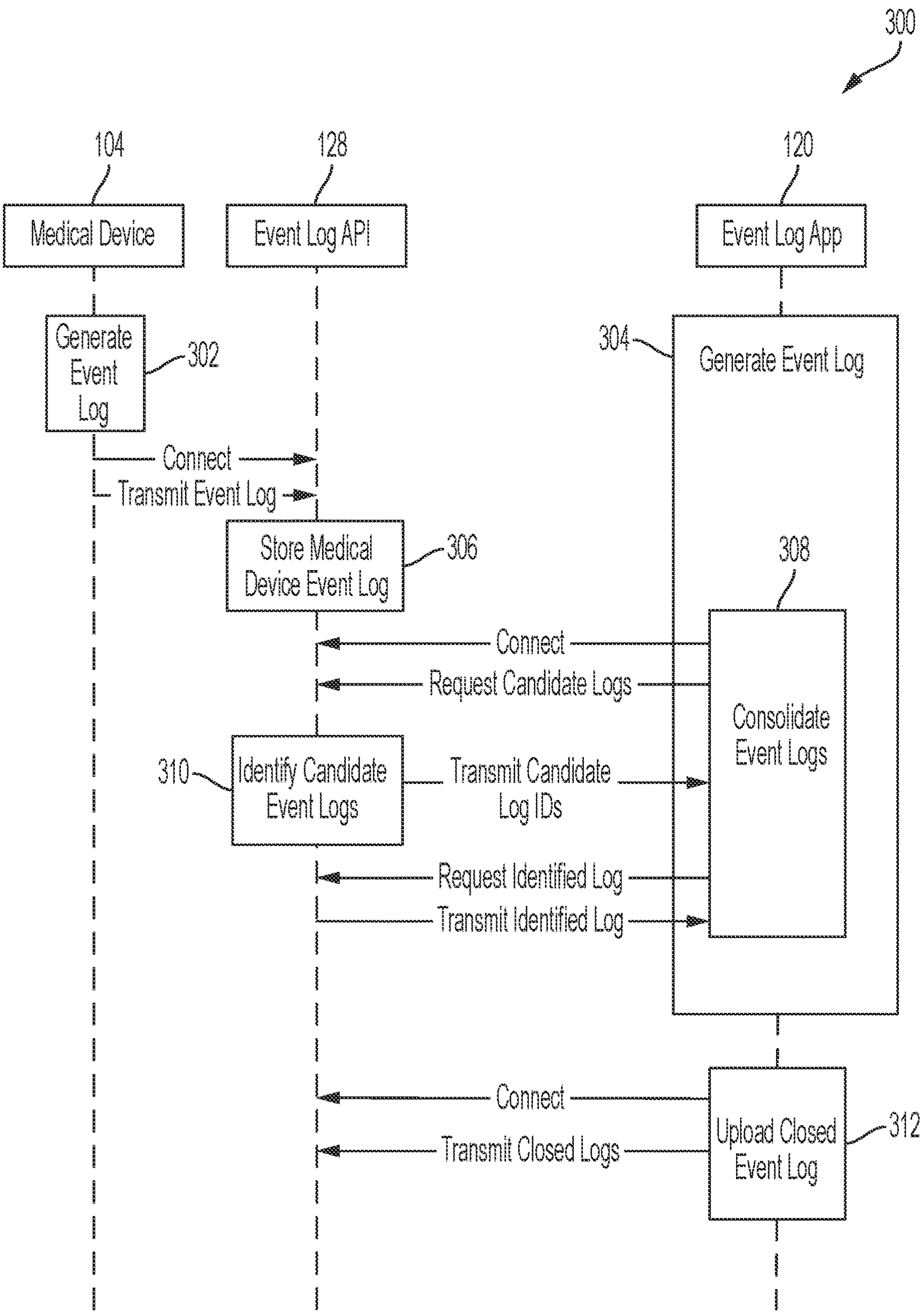
FIG. 3 is a sequence diagram illustrating a process of documenting emergency care in accordance with at least one example disclosed herein.

FIG. 3 illustrates a process for documenting emergency care that is executed by the configuration 200 of the distributed system 100. As shown in FIG. 3, the documentation process 300 includes a sequence of actions that are collectively executed by a medical device (e.g., the medical device 104), an event log API (e.g., the event log API 128), and an event log application (e.g., the event log application 120).

The documentation process 300 starts with the medical device generating 302 an event log (e.g., the event log 124) including one or more entries (e.g., the log entries A through N). Each entry may include a date/time stamp indicating the time at which an event documented by the entry occurred and an indicator of the event, such as a type identifier or a textual description of the event. A wide variety of events can be documented by various examples of medical devices when generating 302 the event log. For instance, in examples where the medical device includes a defibrillator, the medical device can generate log entries, for example, when the defibrillator is powered on, when a healthcare provider (e.g., the healthcare provider 114) enters information identifying a patient (e.g., the patient 118), when the defibrillator prompts the healthcare provider to act, when the defibrillator senses that a particular treatment (e.g., chest compressions sensed via acceleration signals generated from a sensor located on the sternum of the patient, ventilations sensed via flow/pressure signals generated from a sensor located along the patient airway) is being provided to the patient, when the defibrillator senses that the patient has a particular ECG rhythm (e.g., ventricular fibrillation, ventricular tachycardia, asystole, pulseless electrical activity, sinus rhythm, etc.), when the defibrillator delivers a therapeutic electric pulse to the patient, amongst others. In some examples, the generating 302 of the event log ends with the medical device receiving input from the healthcare provider indicating that treatment of the patient is complete (e.g., turning the medical device off, providing an input to close the code event or case) and recording an event indicative of the same in the event log.

As shown in FIG. 3, in response to completing generation of the event log, the medical device connects to the event log API and transmits the event log to the event log API for subsequent processing. Next, the event log API receives, parses, and stores 306 the event log generated by the medical device.

The documentation process 300 continues with the event log application generating 304 log entries (e.g., including the log entries 1 through X of the event log 122 listed in FIG. 2) for an open event log. As with the medical device, each log entry generated by the event log application may include a date/time stamp (e.g., indicating the time at which an event documented by the entry occurred) and an indicator of the event, such as a type identifier or a textual description of the event. A wide variety of events can be documented by the event log application when generating 304 the open event log. Examples of these events include administration of procedures, medications, and other therapies, to name only a few events. Additional examples of events that can be documented are described below with reference to FIGS. 4-28, which illustrate one example of a process and associated screens executed by the event log application to document running a code to treat a patient suffering from cardiac arrest.

As shown in FIG. 3, generating 304 the open event log includes consolidating 308, by the event log application, the open event log with event logs originated from other source devices, such as the medical device. In some examples, as part of consolidating 308 the open event log with other event logs, the event log application connects to the event log API and requests event logs that are candidates for association and consolidation with the open event log. In some examples, the event log application is configured to include, within the request, data indicative of search criteria the event log API can use to search of candidate event logs. Examples of such search criteria include identifiers of medical devices (e.g., serial numbers), patients (e.g., patient IDs), date/time stamps associated with the open event log, and/or an identifier of the particular event log requested.

In response to receiving a request for candidate event logs, the event log API identifies 310 one or more candidate event logs for potential consolidation with the open event log. As part of identifying 310 the one or more candidate event logs, the event log API parses the request for candidate event logs and searches for event logs stored in an event log data store (e.g., the event log data store 126) that can be associated with the open event log. The specific actions executed as part of identifying 310 the one or more candidate event logs vary depending on the information available to the event log API. For instance, in examples in which the request for candidate event logs includes limited or no data indicative of search criteria, the event log API searches for and finds event logs generated within a window of time based on the current time (e.g., event logs with a power on time within the last 2 hours, within the last hour, within the last 30 minutes, etc.). That is, the window of time in which the event logs are generated may be used to identify which event logs are appropriate for consolidation into the same event record. So, for example, if the code event started at 1:00 and a particular medical device (e.g., defibrillator) associated with the code event was powered on at 1:05, then the event log API may identify the particular medical device associated with the code event by the time in which it was powered on falling within the predetermined window of time (e.g., 1:05 falls within a 2 hour window from when the code event started, in fact, is 5 minutes from when the code event started) and, thus, incorporate event logs generated from the particular medical device in the overall consolidated event record associated with the code event. In an example in which the request for candidate event logs includes an identifier of the medical device, the event log API searches for and finds event logs generated by a medical device having the identifier. In another example, where the request for candidate event logs includes a date/time stamp associated with the open event log, the event log API searches for and finds event logs generated within a window of time including the date/time stamp associated with the open event log. In these examples, the duration of the time window may be configurable to, for example, 30 minutes, 1 hour, 2 hours, or another duration. In other examples, the event log API searches for and finds event logs using other information provided in the request for candidate events, such as a unique identifier of an event log requested. Alternatively or additionally, the event log API can search for and find event logs using a combination of the event log identifiers described above. For instance, the event log API can search for event logs generated by a specific medical device within a specific time window. Regardless of the search process that is executed while identifying 310 the one or more candidate event logs, the event log API next transmits identifiers of the candidate event logs (e.g., source device serial numbers, other identification information, power on time, date/time stamps of completion, durations of activity, etc.) resulting from the search process to the event log application. These event log identifiers can include, for example, serial numbers of source devices, identification information (e.g., patient ID information, ID of other items used during the course of the medical event), and/or date/time stamps marking generation of the event log.

Next, as part of consolidating 308 the open event log with other event logs, the event log application requests one or more identified event logs from the event log API. In response, the event log API transmits copies of the one or more identified event logs to the event log application. In some examples, the one or more identified event logs are selected by a user via one or more screen provided by the event log application. Examples of screens that enable selection of particular candidate event logs are described further below with reference to FIG. 23

Next, as part of generating 304 the open event log, the event log application provides a healthcare provider (e.g., the healthcare provider 112) with a view (e.g., the view 202) of the consolidated event log. Generating 304 continues with the interaction between the event log application and the healthcare provider to generate entries for the open event log until the user closes the open event log. In some examples, which are described further below with reference to FIG. 18, the event log application prevents modification, via the view 202, of entries generated by sources other than the event log application.

Next, the event log application uploads 312 closed event logs to the event log data store by connecting to the event log API and transmitting the closed logs to the event log API in conjunction with a command to process and store the closed logs. In some examples, uploading 312 is initiated via screens provided to the user by the event log application as part of an overall interactive process described further below with reference to FIGS. 6 and 7.

The documentation process 300 concludes after uploading 312 is complete. Processes in accordance with the documentation process 300 enable a documenter, such as the healthcare provider 112, to efficiently create a consolidated event log that integrates entries from multiple source devices. Such consolidated event logs provide a single source of documentation that can be used to improve patient treatment protocols and execution of the same by healthcare providers.

In the documentation process 300, the medical device 104 connects to the event log API 128 and uploads closed event logs once treatment of the patient is complete. Similarly, within the documentation process 300, the event log application 120 exchanges closed event logs with the event log API 128 upon completion of patient treatment. However, the examples disclosed herein are limited solely to exchanging closed event logs. For instance, in some examples, a more granular documentation process in accord with FIG. 3 is implemented by the medical device 104, the event log API 128, and the event log application 120. In this more granular documentation process, the medical device 104 and the event log application 120 exchange portions of open event logs (and/or other data, such as CPR compression and/or ventilation quality metrics) with the event log API 128 during patient treatment. The size of these portions can vary between examples and can, in some implementations, be as small as a single event log entry. As such, this more granular documentation process can exchange log entries in real time, thereby enabling the event log application 120 to continuously provide a current consolidated log to healthcare providers. Analogous approaches can be used to increase the granularity of the processes 3000, 3100, 3900, 4100, 4200, 4300, and 4400 as described below with reference to FIGS. 30, 31, 39, 41, 42, 43, and 44. When executing in these more granular processes, the components of the system 100 are referred to herein as executing in real time mode.

Log Generation Screens and Processes

FIGS. 4, 6, 18, 20, and 25 collectively illustrates a process 400 for generating a consolidated event log (e.g., the event log accessible via the view 202) to document a code ran by one or more healthcare providers (e.g., the healthcare provider 114) to treat a patient (e.g., the patient 118) suffering from cardiac arrest. In some examples, the log generation process 400 is executed by an event log application (e.g., the event log application 120) within the context of an overall documentation process, such as the documentation process 300. In these examples, the event log application generates 304 the event log by executing the log generation process 400 and/or portions thereof.

Figure 4:
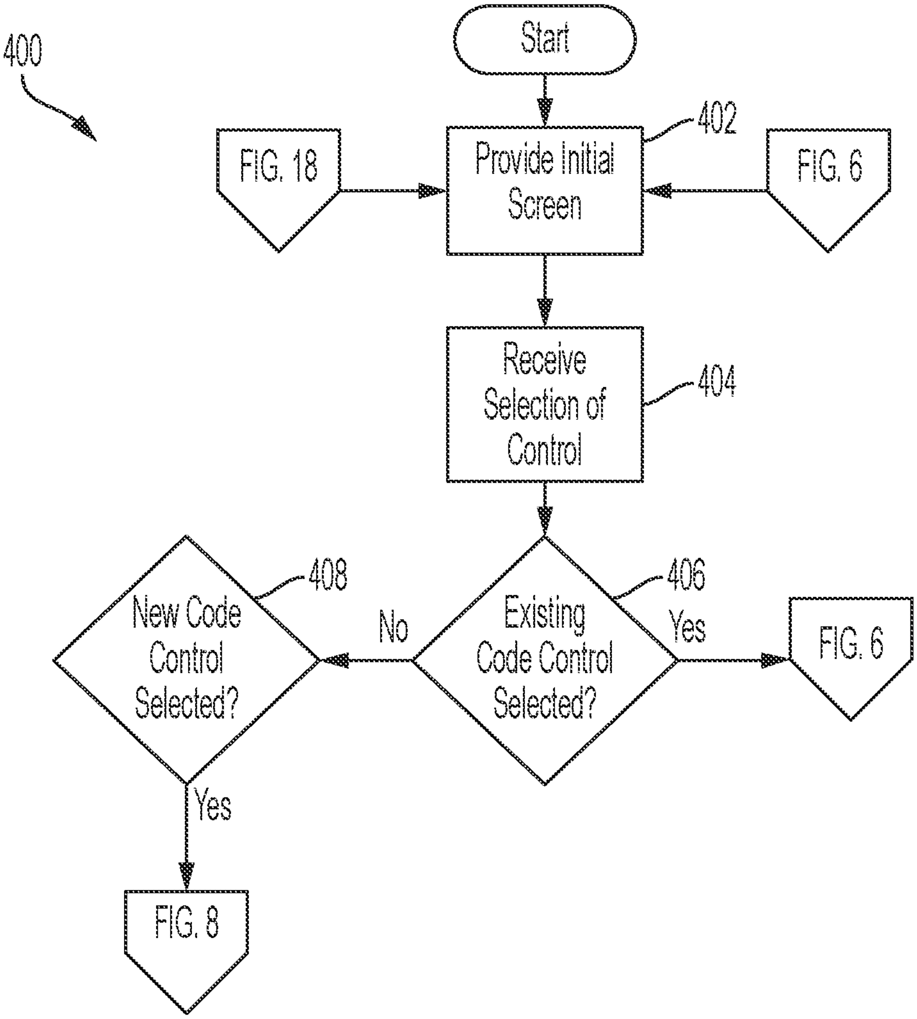
FIG. 4 is a flow diagram illustrating a portion of a process of generating log entries in accordance with at least one example disclosed herein.
Figure 5:
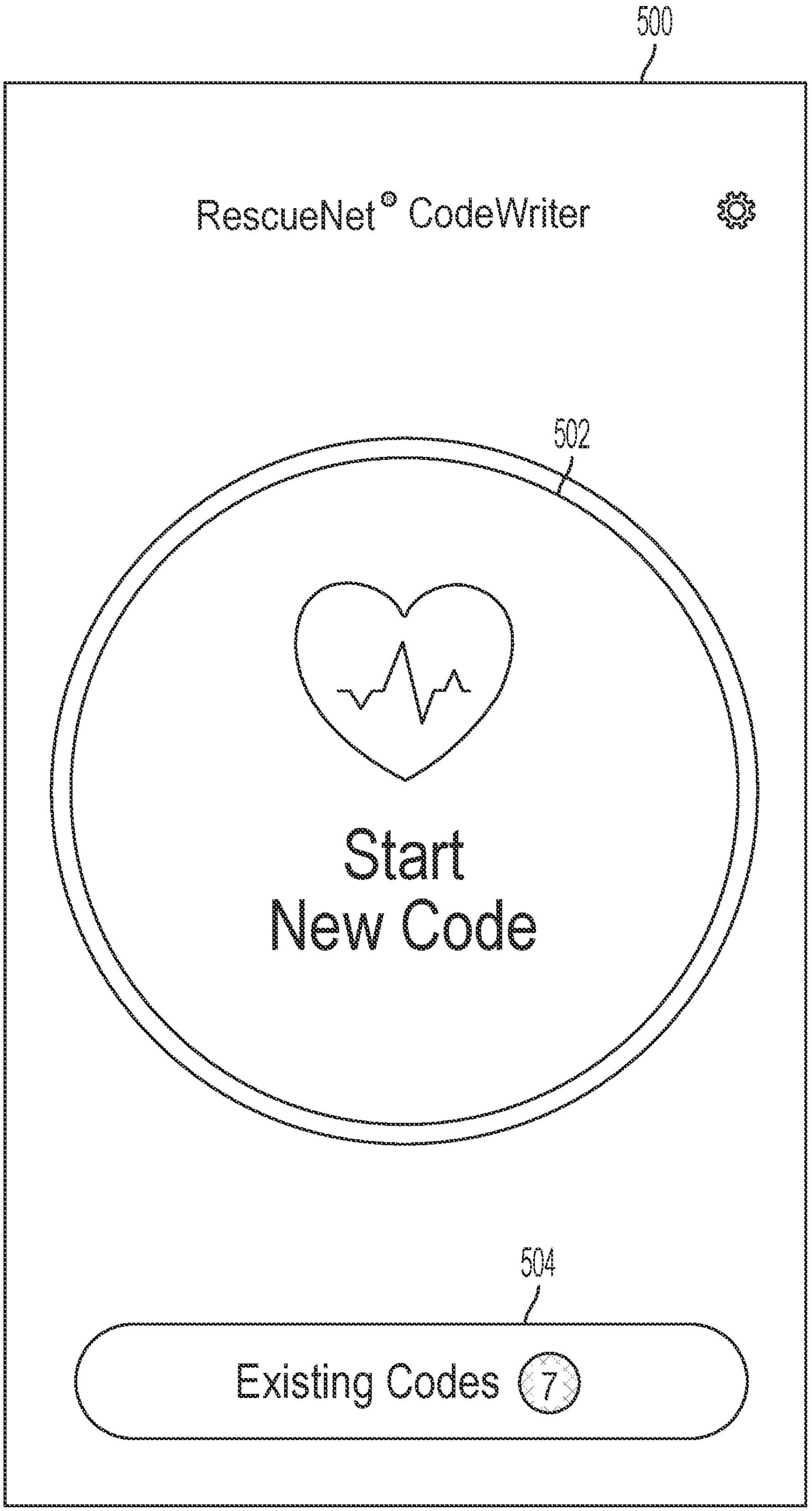
FIG. 5 is a view of an initial screen provided by an event log application in accordance with at least one example disclosed herein.

As shown in FIG. 4, the log generation process 400 starts with the event log application providing 402 an initial screen within a user interface of a mobile computing device (e.g., the mobile computing device 102). FIG. 5 illustrates one example of an initial screen 500 that may be displayed as a result of providing 402 the initial screen. As shown in FIG. 5, the initial screen 500 includes a new code control 502 and an existing codes control 504.

In some examples, the healthcare provider can select the new code control 502 to start a new code for a patient. Alternatively, the healthcare provider can select the existing codes control 504 to perform additional processing of a previously started, but incomplete or open, code. This additional processing can include revision of entries included in an event log associated with the code, adding new entries to the event log, and/or uploading the existing event log to a remote server (e.g., the server 108). Examples of the additional processing available via the existing codes control 504 are described further below with reference to FIG. 7.

As shown in FIG. 5, the new code control 502 is sized and positioned to facilitate ease of selection by a user holding the mobile computing device 102 with one hand, which is a common situation in emergency situations. The new code control 502 is circular and centered, which enables either a left-handed or a right-handed user to easily tap the new code control 502 with her thumb. Moreover, the new code control 502 is sized to enable the distal portion of a user's thumb to flexion toward the user's palm to select the new code control 502 from a variety of angles and holding positions. Thus, the particular design of the initial screen 500 provides advantages over other potential designs.

Figure 6:
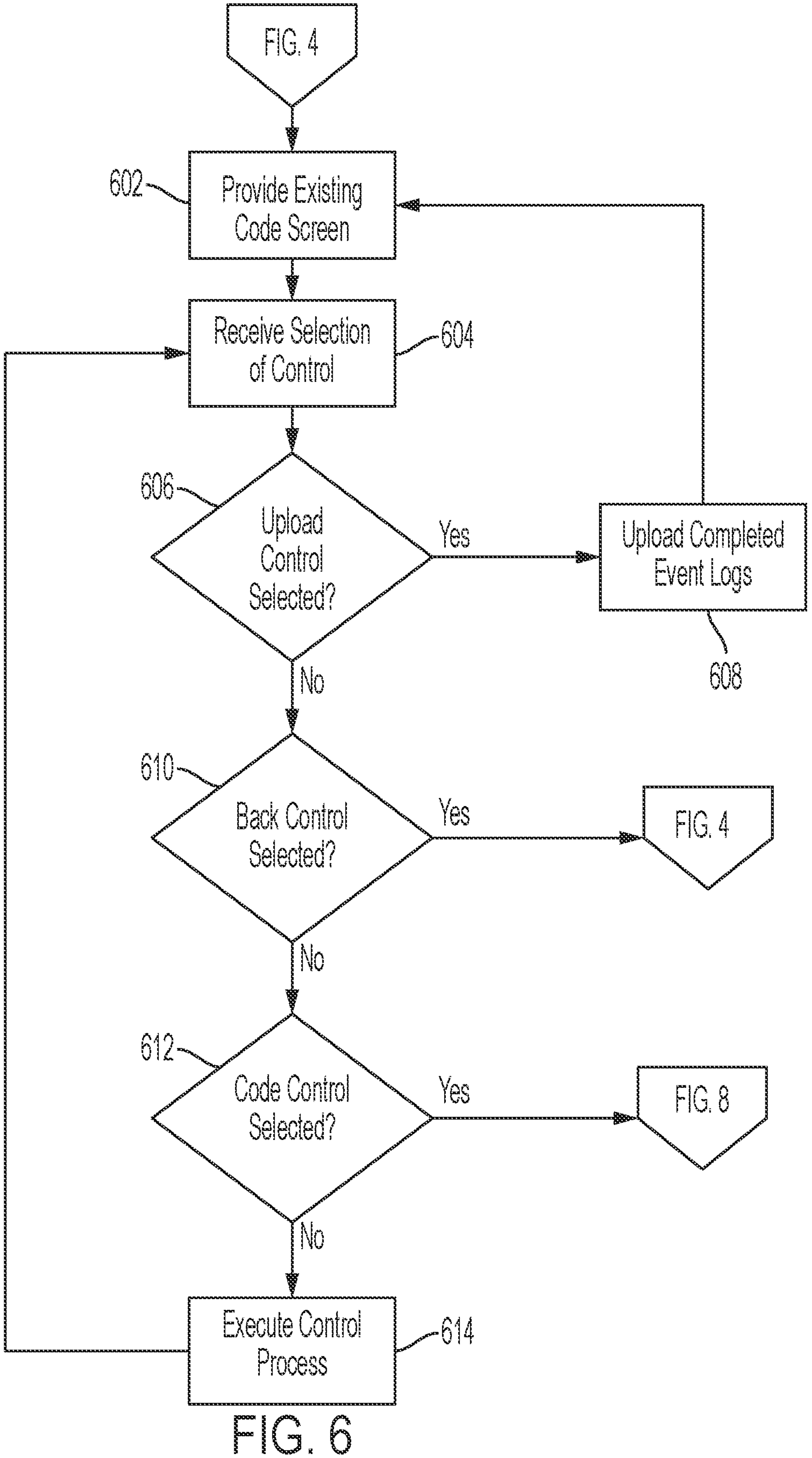
FIG. 6 is a flow diagram illustrating another portion of a process of generating log entries in accordance with at least one example disclosed herein.
Figure 7:
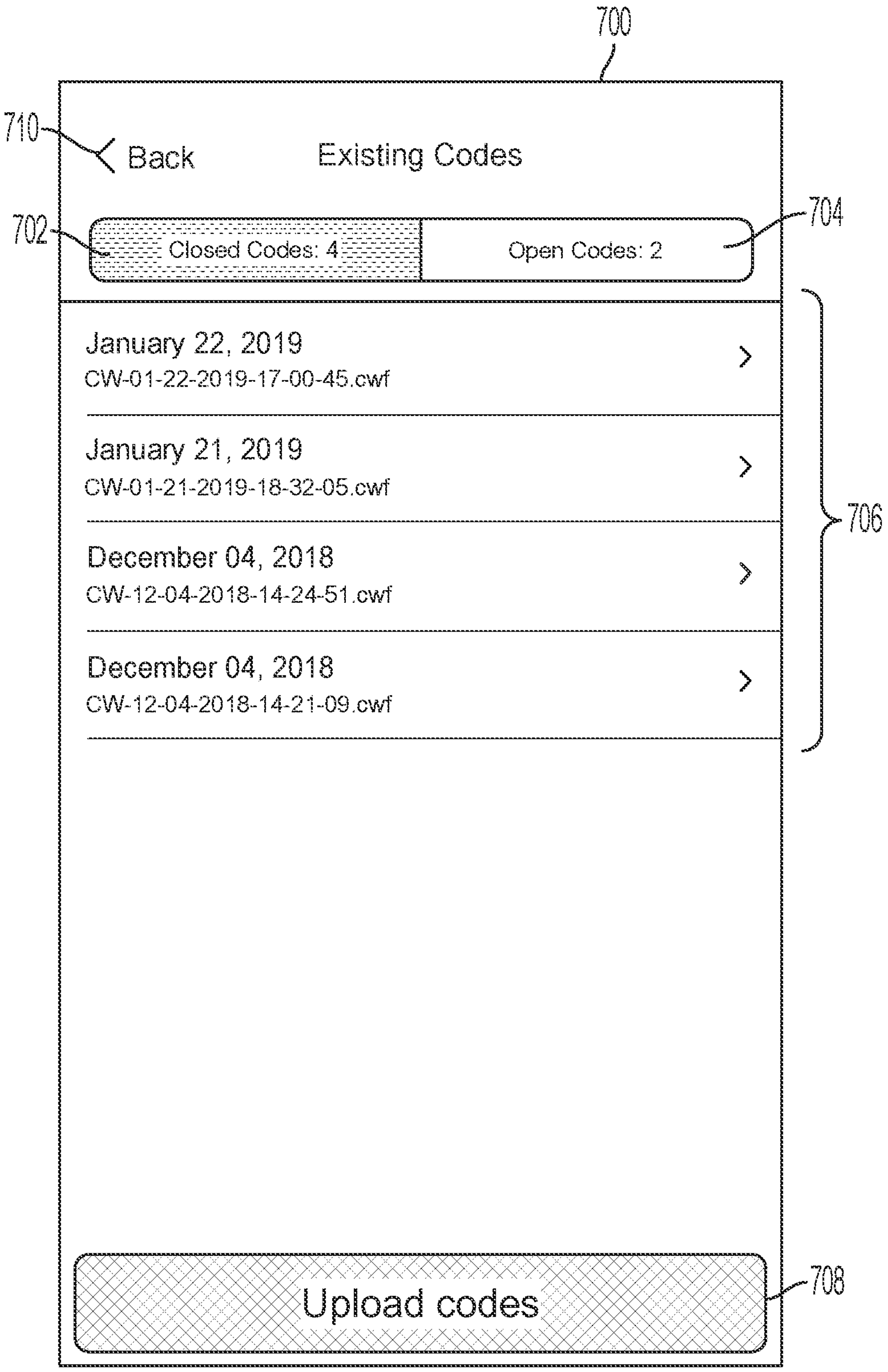
FIG. 7 is a view of an existing codes screen provided by an event log application in accordance with at least one example disclosed herein.

Returning to the log generation process 400 with reference to FIGS. 4 and 6, the event log application receives 404 input selecting a control (e.g., either the new code control 502 or the existing codes control 504). The event log application determines 406 whether the existing codes control 504 was selected. If the existing codes control 504 was selected, the event log application provides 602 an existing codes screen, such as the existing codes screen 700 that is illustrated in FIG. 7. As shown in FIG. 7, the existing codes screen 700 includes a closed codes control 702, an open codes control 704, a set of code controls 706, an upload control 708, and a back control 710. As shown in FIG. 7, each code control of the set of code control 706 is associated and labeled with an identifier of an event log associated with an existing code.

Continuing with the log generation process 400 with reference to FIGS. 6 and 7, the event log application receives 604 input selecting a control included within the existing codes screen 700. The event log application determines 606 whether the upload control 708 was selected. If the upload control 708 was selected, the event log application connects to an event log API (e.g., the event log API 128) and uploads 608 an event log for each closed code stored on the mobile computing device.

If the upload control 708 was not selected, the event log application determines 610 whether the back control 710 was selected. If the back control 710 was selected, the event log application provides 402 the initial screen 500. If the back control 710 was not selected, the event log application determines 612 whether a code control from the set of code controls 706 was selected. If a code control was selected, the event log application provides 802 an event log screen, such as the event log screen 900 illustrated in FIG. 9, for the event log associated with the code control. This action enables the healthcare provider to access and revise the event log as described further below.

If a code control was not selected, the event log application executes 614 a process associated with the selected control. For instance, in response to receiving input selecting the closed codes control 702, the event log application updates the set of code controls 706 to include identifiers of closed codes stored on the mobile computing device. Closed codes are codes that have been previously recorded as complete via interaction between the event log application and the healthcare provider. Similarly, in response to receiving input selecting the open codes control 704, the event log application updates the set of code controls to include identifiers of open codes stored on the mobile computing device. Open codes are codes that have been started, but not completed, via interaction between the event log application and the healthcare provider. After executing 614 the process associated with the selected control, the event log application returns to monitoring for user input.

Figure 8:
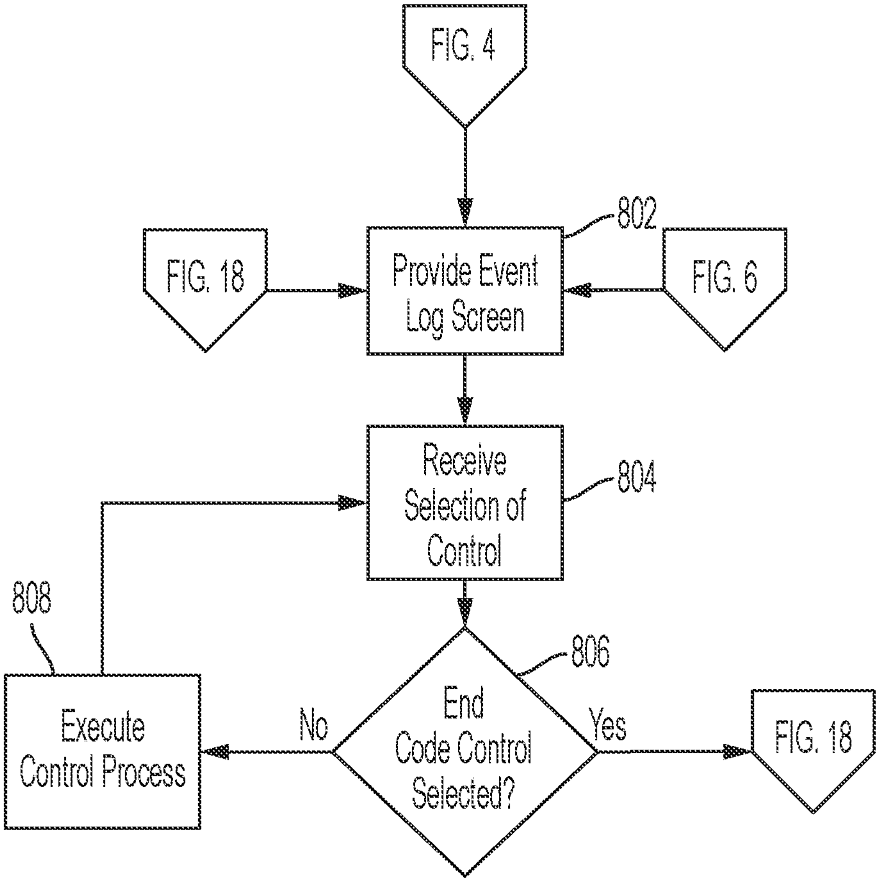
FIG. 8 is a flow diagram illustrating another portion of a process of generating log entries in accordance with at least one example disclosed herein.
Figure 9:
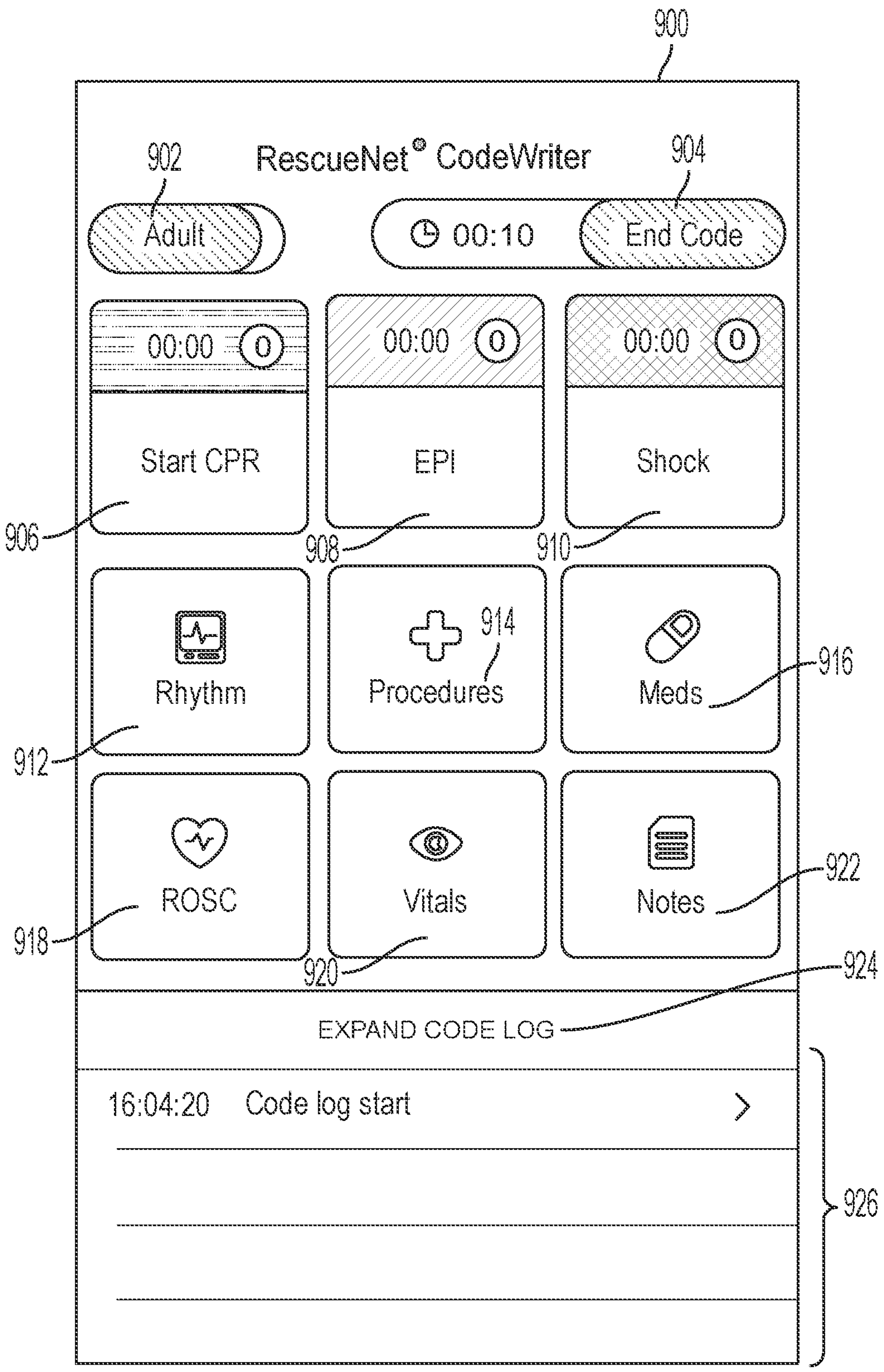
FIG. 9 is a view of a main screen provided by an event log application in accordance with at least one example disclosed herein.

Returning to FIG. 4 with additional reference to FIG. 8, if the event log application determines 406 that the existing codes control 504 was not selected, the event log application determines 408 whether the new code control 502 was selected. If the new control 502 was selected, the event log application provides 802 an event log screen, such as the event log screen 900 that is illustrated in FIG. 9. As shown in FIG. 9, the event log screen 900 includes a variety of controls. These controls include an adult/pediatric control 902, an end code control 904, a CPR control 906, an EPI control 908, a shock control 910, a rhythm control 912, a procedures control 914, a medicines control 916, a return of spontaneous circulation (ROSC) control 918, a vitals control 920, a notes control 922, an expand control 924, and a code log control 926 that includes one or more entry controls.

Each of the controls included in the event log screen 900 enable the healthcare provider to access documentation functionality associated with the name of the control. For example, the adult/pediatric control 902 enables the healthcare provider to specify whether the patient is a child or an adult, while the code log control 926 displays information descriptive of recently added log entries—such as those that may be entered via the controls 906-922. A detailed description of each of the controls included in the event log screen 900 is provided below.

Continuing with the log generation process 400 with reference to FIG. 8, the event log application receives 804 input selecting a control of the event log screen 900. The event log application determines 806 whether the end code control 904 was selected. If the end code control 904 was selected, generation of additional log entries are at least temporarily ended, and the event log application provides an end code screen, such as the end code screen 1900 described further below with reference to FIG. 19

If the end code control 904 was not selected, the event log application executes 808 a process associated with the selected control. For instance, where the selected control is the CPR control 906 and the CPR control 906 has not been previously selected, the event log application creates and stores an entry within the event log to document the start of CPR. However, where the CPR control 906 was previously selected, the event log application responds to its selection by toggling the state of the CPR control from its current state to a new state (e.g., from an active state to a paused state or from a paused state to an active state) and recording an entry with the event log to document the change in state. In some examples, the event log application alters the CPR control 906 to reflect its current state. For instance, in at least one example, the event log application labels the CPR control 906 with "Resume CPR" to reflect a paused state (where actuation of the CPR control 906 will indicate CPR being resumed and an associated log entry being created) and labels the CPR control 906 with "Pause CPR" to reflect an active state (where actuation of the CPR control 906 will indicate CPR being paused and an associated log entry being created).

Further, in certain examples, the event log application provides the healthcare provider with additional useful indications via the CPR control 906. For instance, in at least one example, the event log application causes the CPR control 906 to flash, become highlighted, change color and/or provide another suitable indication to alert the healthcare provider after a period of time has elapsed since the previous time the CPR control 906 was selected. This period of time can be configurable and can be associated with the state of the CPR control 906. For example, the period of time associated with the paused state (e.g., where CPR is idle) can be 5, 10, 15, 20 seconds, or another suitable period of time. The period of time associated with the active state can be 90 seconds, 120 seconds, 180 seconds, or another suitable period of time. Additionally or alternatively, in some examples, the event log application displays a CPR timer within the CPR control 906 that indicates the amount of time that has elapsed since the CPR control 906 was previously selected and/or a counter within the CPR control 906 that indicates the total number of times CPR (chest compressions and/or ventilations) has been restarted/resumed during the code being documented.

Where the selected control is the EPI control 908, the event log application creates and stores an entry within the event log to document the administration of EPI to the patient. As with the CPR control 906, in some examples, the event log application provides the healthcare provider with additional useful indications via the EPI control 908. For instance, in at least one example, the event log application causes the EPI control 908 to flash, become highlighted, change color and/or provide another suitable indication to alert the healthcare provider after a period of time has elapsed since the previous time the EPI control 908 was selected. For example, this period of time can be 2, 3, 4 minutes, or another suitable period of time. Additionally or alternatively, in some examples, the event log application displays a drug timer within the EPI control 908 that indicates the amount of time that has elapsed since the EPI control 908 was previously selected and/or a counter within the EPI control 908 that indicates the total number of times EPI has been administered during the code being documented.

Where the selected control is the shock control 910, the event log application creates and stores an entry within the event log to document the administration of a therapeutic shock to the patient. As with the EPI control 908, in some examples, the event log application provides the healthcare provider with additional useful indications via the shock control 910. For instance, in at least one example, the event log application displays an electrotherapy timer with the shock control 910 that indicates the amount of time that has elapsed since the shock control 910 was previously selected and/or a counter with the shock control 910 that indicates the total number of times a therapeutic shock has been administered during the code being documented.

Where the selected control is the rhythm control 912, the event log application provides a screen that includes a set of rhythm controls. Each rhythm control of the set is associated and labeled with a particular rhythm. In response to receiving input selecting a rhythm control of the set of rhythm controls, the event log application creates and stores an entry within the event log to document identification of the rhythm. Examples of rhythms that may be associated with rhythm controls in the event log application include asystole, pulseless electrical activity, pulseless ventricular tachycardia, ventricular defibrillation, accelerated idioventricular rhythm, atrial fibrillation, atrial flutter, bradycardia, paced, sinus (which may include sinus tachycardia), supraventricular tachycardia, third degree block, ventricular tachycardia, and unknown/other. In some embodiments, the event log application is in communication with a defibrillator/monitor or ECG monitoring device that receives and analyzes ECG so as to classify the cardiac rhythms; and if the analysis is able to classify the particular rhythm, then the particular selection in the event log application may be highlighted for the user to confirm.

In some examples, the event log application responds to selection of certain rhythm controls by providing a follow-up screen that includes controls that allow input of specific parameters associated with the identified rhythm. In these examples, the event log application records these parameters along with the log entry. Examples of the parameters that can be associated with a log entry documenting identification of a rhythm include whether a pulse is absent, present and adequate. Examples of a parameter that can be associated with a log entry documenting an unknown rhythm include a free form text description of the rhythm observed.

Where the selected control is the procedures control 914, the event log application provides a screen that includes a set of procedure controls. Each procedure control of the set is associated and labeled with a particular procedure. In response to receiving input selecting a procedure control of the set of procedure controls, the event log application creates and stores an entry within the event log to document administration of the procedure. Examples of procedures that may be associated with procedure controls by the event log application include placement of a bag-valve-mask, an ET tube, or other airway/breathing procedure; placement of an IV or other vascular access device; placement of a chest tube; determining blood glucose or arterial blood gas (ABG) test results; drawing blood for labs; delivery of pacing or synchronized cardioversion; administering a 12-lead electrocardiogram (ECG) or an echocardiogram; performing a pericardiocentesis, thoracostomy, x-rays, or vagal stimulation; and performing a custom procedure (i.e. one that can be described in freeform text).

In some examples, the event log application responds to selection of certain procedure controls by providing a follow-up screen that includes controls that allow input of specific parameters associated with the selected procedure. In these examples, the event log application records the parameters along with the log entry.

Examples of parameters that can be associated with a log entry documenting placement of an ET tube include the tube size, position, method of confirmation (e.g., auscultation, chest x-ray, end-tidal carbon dioxide, or esophageal detector), and a name of placer.

Examples of parameters that can be associated with a log entry documenting performance of other airway/breathing procedures include a type of device placed (e.g., combitube, king tube, laryngeal mark airway, mouth-to-barrier device, or impedance threshold device), a type of procedure performed (cricothyrotomy, extubation, mouth-to-mouth, suction, tracheostomy), a confirmation of placement of a device or completion of a procedure, and free form text.

Examples of parameters that can be associated with a log entry documenting placement of a vascular device include a site of the device (e.g., venous, arterial, intraosseous), a side of the patient in which the device is placed (e.g., left or right), a type of access (central or peripheral), a location of the device (ante-cubital, hand, jugular, pedal, saphenous vein), and device size.

Examples of parameters that can be associated with a log entry documenting blood glucose level include a blood glucose value (e.g., in mg/dL).

Examples of parameters that can be associated with a log entry documenting blood drawn for labs include indicators of the labs for which the blood was drawn (e.g., ABG, blood urea nitrogen, calcium, cardiac enzymes, complete blood count, creatinine, d-dimer, electrolytes, lactate, glucose, international normalized ratio, magnesium, prothrombin time, and/or partial thromboplastin time).

Examples of parameters that can be associated with a log entry documenting delivery of a pacing procedure include whether the log entry documents the starting or stopping of pacing, whether pacing resulted in capture, and whether the pacemaker used was epicardial, transcutaneous, or transvenous.

Examples of parameters that can be associated with a log entry documenting performance of an x-ray include the portion of the patient's anatomy x-rayed (e.g., the patient's chest or other location).

Examples of parameters that can be associated with a log entry documenting performance of a custom procedure include a free form textual description of the custom procedure.

Where the selected control is the medicines control 916, the event log application provides a screen that includes a set of medicine controls. Each medicine control of the set is associated and labeled with a particular medicine. In response to receiving input selecting a medicine control of the set of medicine controls, the event log application creates and stores an entry within the event log to document administration of the medicine. Examples of medicine that may be associated with medicine controls by the event log application include atropine, amiodarone, lidocaine, magnesium sulfate, naloxone, potassium, sodium bicarb, vasopressin, IV fluids, and a custom med.

In some examples, the set of medicine controls may include multiple controls for a single medicine, each with a different but commonly administered dosage. This layout allows the healthcare provider to accurately select a combination of medicine and dosage with a single, quick selection. Examples of combinations of medicines and dosages that may be associated with a medicine controls by the event log application include amiodarone 300 mg, amiodarone 150 mg, lidocaine: 1.5 mg, and lidocaine 0.75 mg.

In some examples, the event log application responds to selection of certain medicine controls by providing a follow-up screen that includes controls that allow input of specific parameters associated with the selected medicine. In these examples, the event log application records the parameters along with the log entry.

Examples of parameters that can be associated with a log entry documenting administration of a custom medication include a free form textual description of the custom medication.

Examples of parameters that can be associated with a log entry documenting administration of IV fluids include whether the log entry documents the starting or stopping of administration, the type of IV fluids administered (e.g. lactated ringers, normal saline, dextrose in normal saline, or another type), the volume of IV fluids administered (e.g., 250 ml, 500 ml, 1000 ml, or another volume), and whether or not the flow rate was wide open.

Where the selected control is the ROSC control 918, the event log application creates and stores an entry within the event log to document that ROSC for the patient has occurred. In some embodiments, the event log application is in communication with the local defibrillator/monitor, and may receive a signal that ROSC has occurred, effectively providing the input for ROSC. An event log that documents that ROSC for the patient has occurred may be helpful in providing an accurate summary of chest compression and/or ventilation performance. For instance, one of the factors in evaluating whether quality chest compressions and/or ventilation have been provided to the patient is based on whether chest compressions and/or ventilation have been continually provided. Accordingly, CPR performance summaries commonly report the chest compression fraction which refers to the percentage of time in which chest compressions are administered by rescuers during a cardiac arrest. However, during the course of a cardiac resuscitation, it is necessary to check the patient periodically to assess whether ROSC has occurred. If ROSC has occurred, then CPR is no longer necessary, and so chest compressions may be discontinued. Accordingly, the selected ROSC control 918 may provide an indication for the system/processor generating the CPR summary report to calculate the chest compression fraction from the time period up to when ROSC has occurred. Otherwise, inclusion of the time period after ROSC has occurred may result in an inaccurate calculation of chest compression fraction. For example, the reported chest compression fraction may be inaccurately low when the time period after ROSC has occurred is mistakenly included in the overall calculation.

In some examples, where the selected control is the vitals control 920, the event log application provides a screen that includes a set of vital sign controls. Each vital sign control of the set is associated and labeled with a particular vital sign. In response to receiving input selecting a vital sign control of the set of vital sign controls, the event log application enables the vital sign control to receive input specifying a value of the vital sign. Examples of vital signs that may be associated with vital sign controls in the event log application include blood pressure, heart rate, Sp02, EtCO2, temperature, and respiration rate (and whether or not the respiration rate was agonal). In response to receiving input specifying a value of a vital sign, the event log application creates and stores an entry within the event log to document the value of the vital sign.

In some examples, the event log application responds to selection of certain vital sign controls by providing a follow-up screen that includes controls that allow input of specific parameters associated with the selected vital sign. In these examples, the event log application records the parameters along with the log entry. Examples of the parameters that can be associated with a log entry documenting a patient's temperature include the site associated with the temperature measurement (e.g., axillary, bladder, blood, brain, oral, rectal, surface, tympanic, or elsewhere), the units of the measurement, and the value of the measurement.

Figure 10:
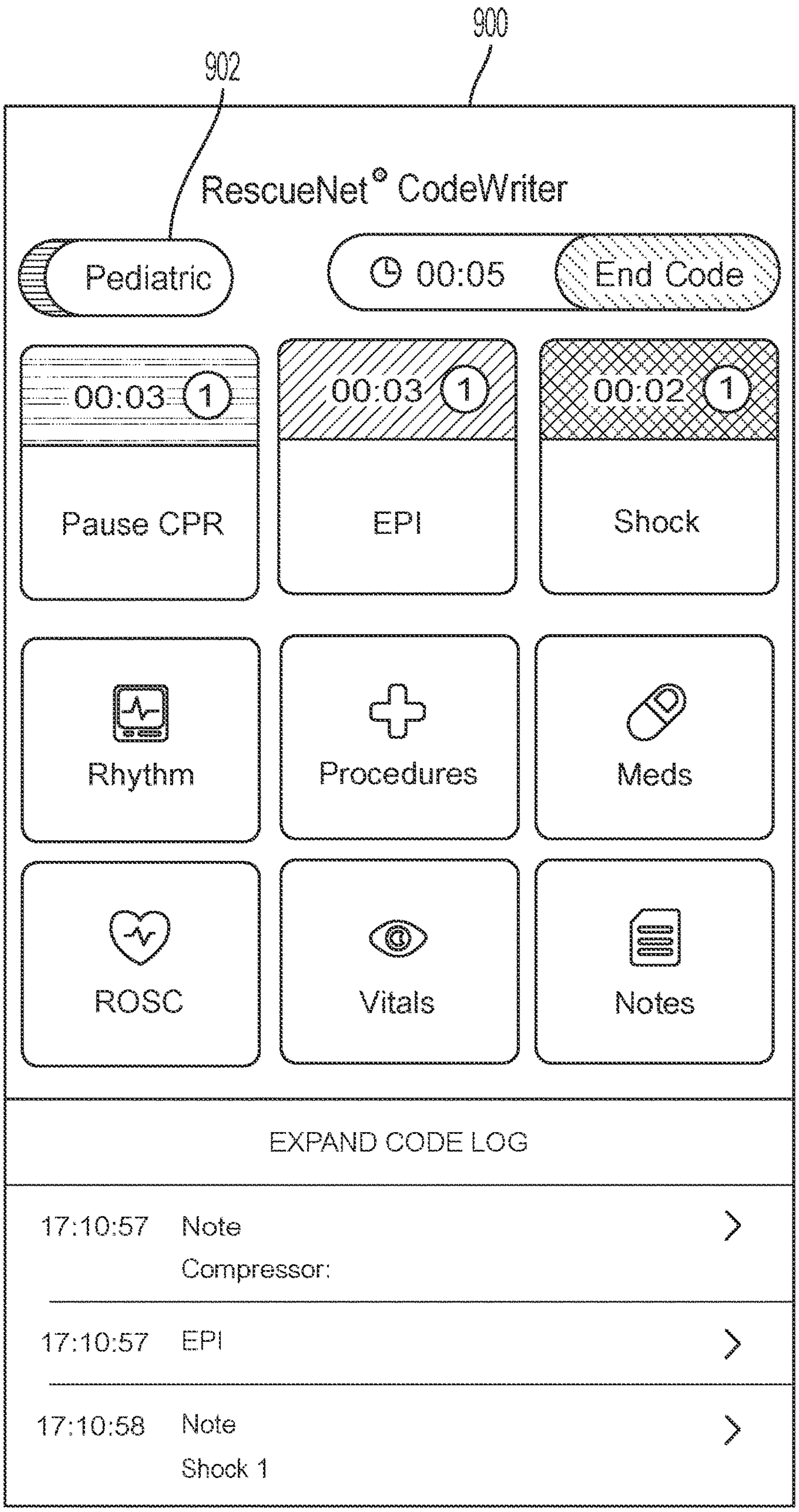
FIG. 10 is a view of the main screen of FIG. 9 in pediatric mode in accordance with at least one example disclosed herein.
Figure 11:
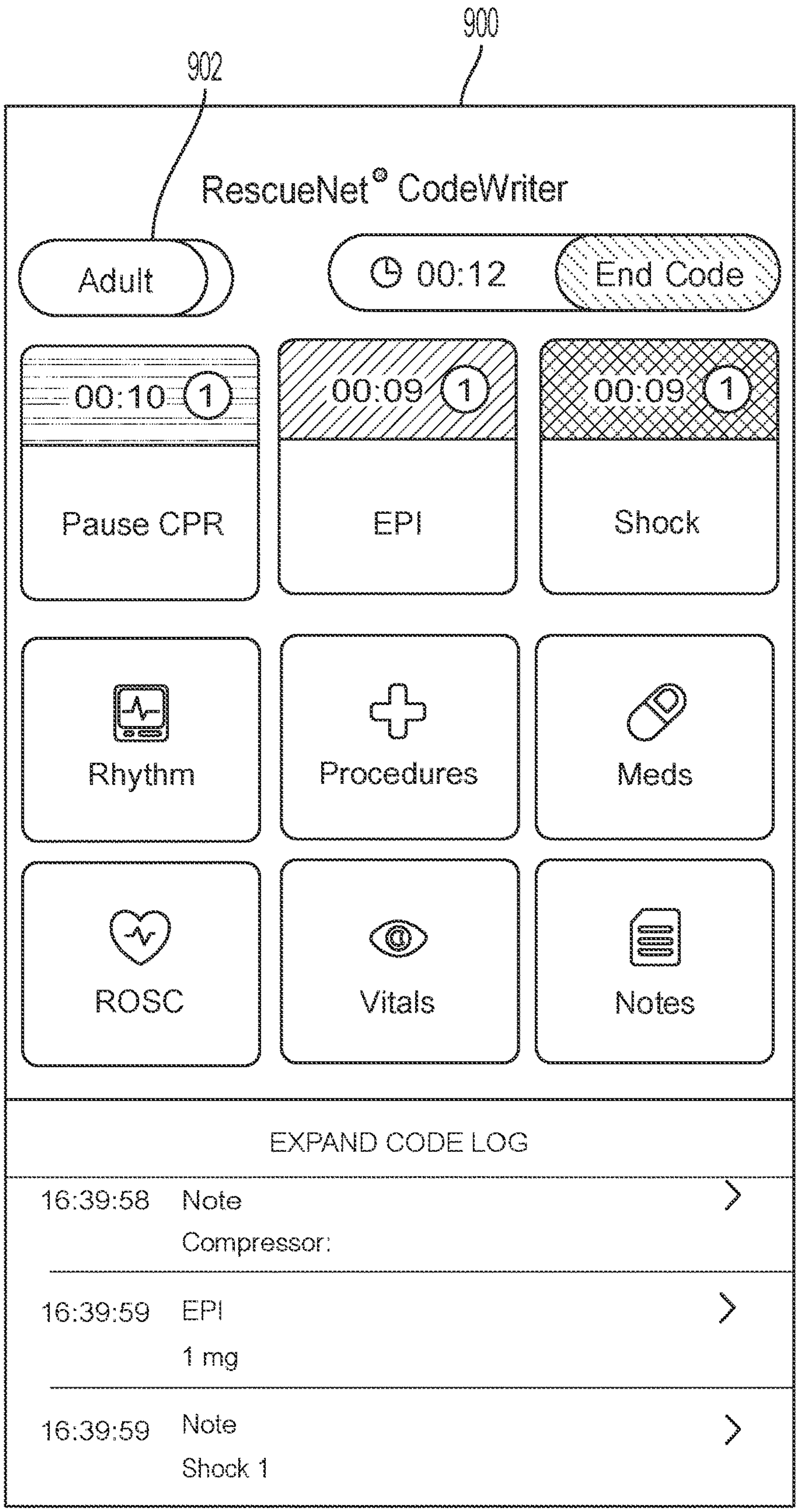
FIG. 11 is a view of the main screen of FIG. 9 in adult mode in accordance with at least one example disclosed herein.

In some examples, where the selected control is the vitals control 920 and the event log application is configured to operate in real time mode, the event log application transmits a request to an event log API (E.G., the event log API 128) or directly to a medical device (e.g., the medical device 104) to request vitals signs for the patient as recorded by the medical device. In these examples, the event log application stores vital signs received from the event log API or directly from the medical device within the corresponding vital sign control and creates log entries to document the patient's vital signs.

Where the selected control is the notes control 922, the event log application provides a screen that configured to receive input specifying a free form text note and/or an indication of whether the note pertains to pre-arrest history. In response to receiving input specifying a text of the note, the event log application creates and stores an entry within the event log to document the note.

Where the selected control is an entry control of the code log control 926, the event log application provides a screen that displays information included in a log entry associated with the selected entry control. This log entry information varies depending on the log entry selected but will include values of the date/time stamp of the entry. In some examples, the screen is configured to receive input that specify values of the log entry information. In response to receiving input specifying a new value of log entry information, the event log application updates the entry within the event log to reflect the new value.

Where the selected control is expands control 924, the event log application expands the code log control 926 to span a greater portion, or all of, the event log screen 900.

Where the selected control is the adult/pediatric control 902, the event log application toggles the mode of the event log application between a first documentation mode and a second documentation mode, such as from its current mode to another mode (e.g., from adult mode to pediatric mode or from pediatric mode to adult mode). When operating in adult mode, the event log application alters certain aspects of screens to enhance their utility in documenting care of adult patients. FIG. 11 depicts the event log screen 900 in adult mode. Conversely, when operating in pediatric mode, the event log application alters certain aspects of screens to enhance their utility in documenting care of pediatric patients. FIG. 10 depicts the event log screen 900 in pediatric mode. Specific examples of these alterations are described further below with reference to FIGS. 12-17.

Figure 12:
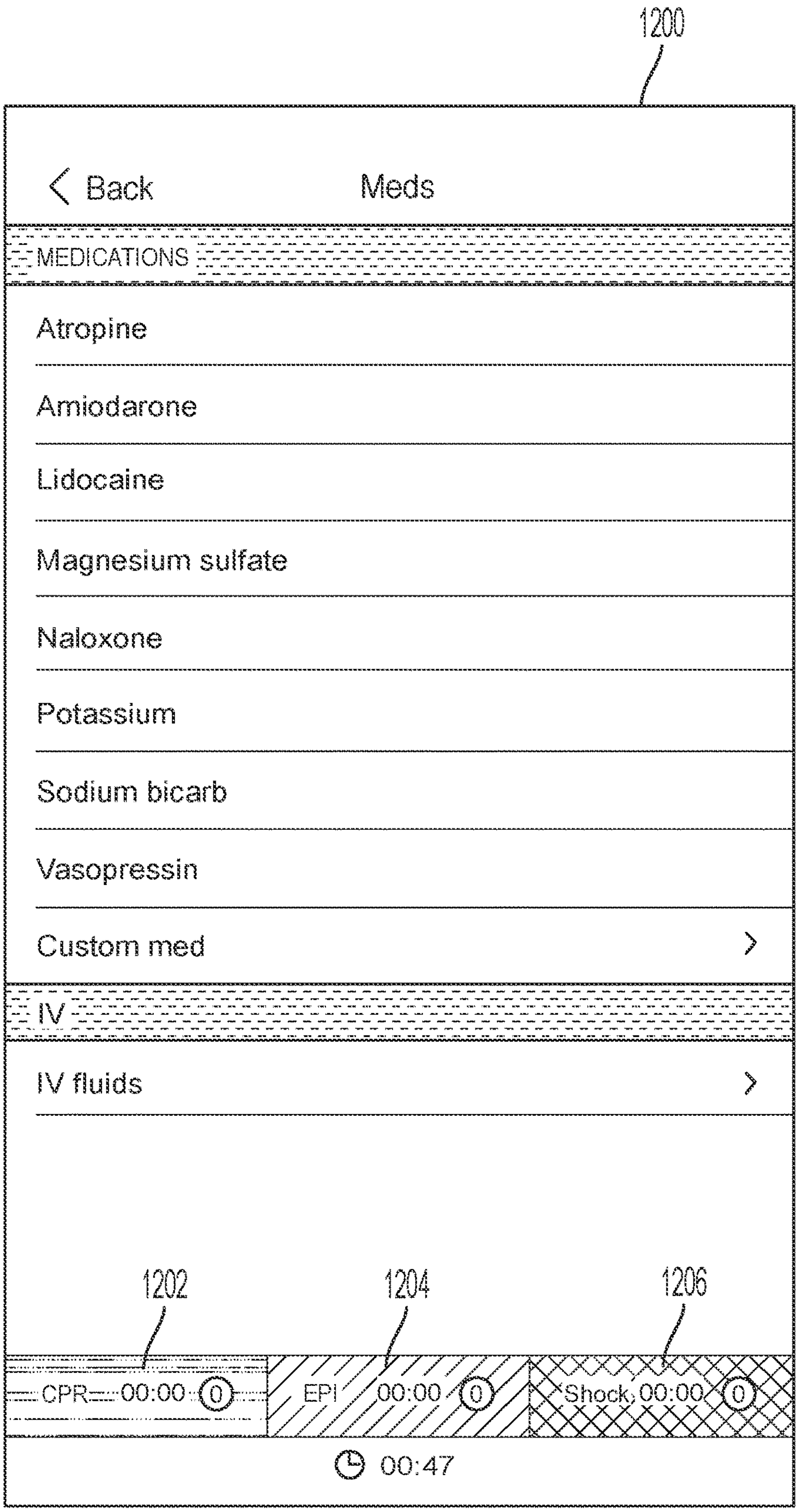
FIG. 12 is a view of a medications screen provided by an event log application in pediatric mode in accordance with at least one example disclosed herein.
Figure 13:
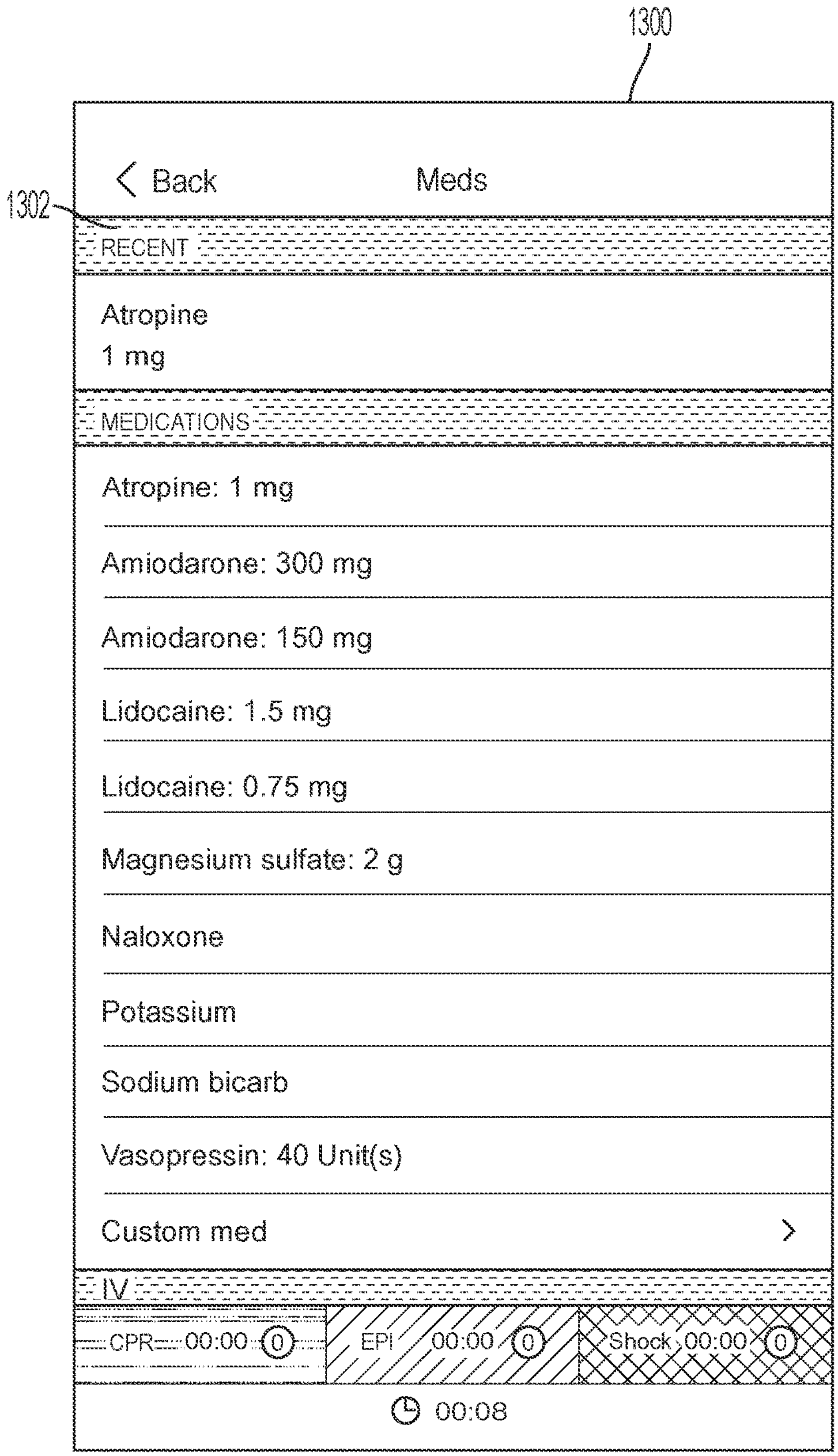
FIG. 13 is a view of the medications screen provided by an event log application in adult mode in accordance with at least one example disclosed herein.

For instance, FIGS. 12 and 13 depict medicines screens 1200 and 1300, either of which may be displayed in response to selection of the medicines control 916 in some examples. More specifically, the medicines screen 1200 is displayed where the event log application is executing in pediatric mode, and the medicines screen 1300 is displayed where the event log application is executing in adult mode. As shown, the medicines screen 1200 includes a set of medicine controls that do not list suggested dosage amounts. Specific dosage amounts may not be listed when in pediatric mode because the range of dosages for pediatric patients may vary widely, for example, for infants, neonates, toddlers, older children, etc. However, the medicines screen 1300 includes medicine controls labeled and associated with combinations of medicines and suggested dosage amounts. In this case, specific dosage amounts may be listed when in adult mode because the appropriate dosage for adults may be more predictable, in contrast with that of pediatric patients. The suggested dosage amount may, for example, comply with the American Heart Association guidelines for treatment of adults. The presence of medicine controls associated with these combinations facilitates quick, easy, and accurate recordation of log entries for adults while a code is being run.

The medicines screens 1200 and 1300 illustrates others feature implemented in some examples by the event log application. For instance, the medicine screen 1200 includes an abbreviated CPR control 1202, an abbreviated EPI control 1204, and an abbreviated shock control 1206. Each of these abbreviated controls can implement one or more of the features of the full-sized controls 906, 908, and 910. The inclusion of the abbreviated controls in the medicine screens (and other screens that may be navigated the event log screen 900) allows the healthcare provider to stay abreast of the status of these important aspects of the code while navigating to other screens available in the event log application.

Another feature common to many screens provided by the event log application is illustrated in FIG. 1300. This feature is the recent section 1302. As shown, the recent section 1302 includes one or more medicine controls that have been previously selected. This feature enables quick and accurate selection of repeated actions, which is common when running a code.

Figure 14:
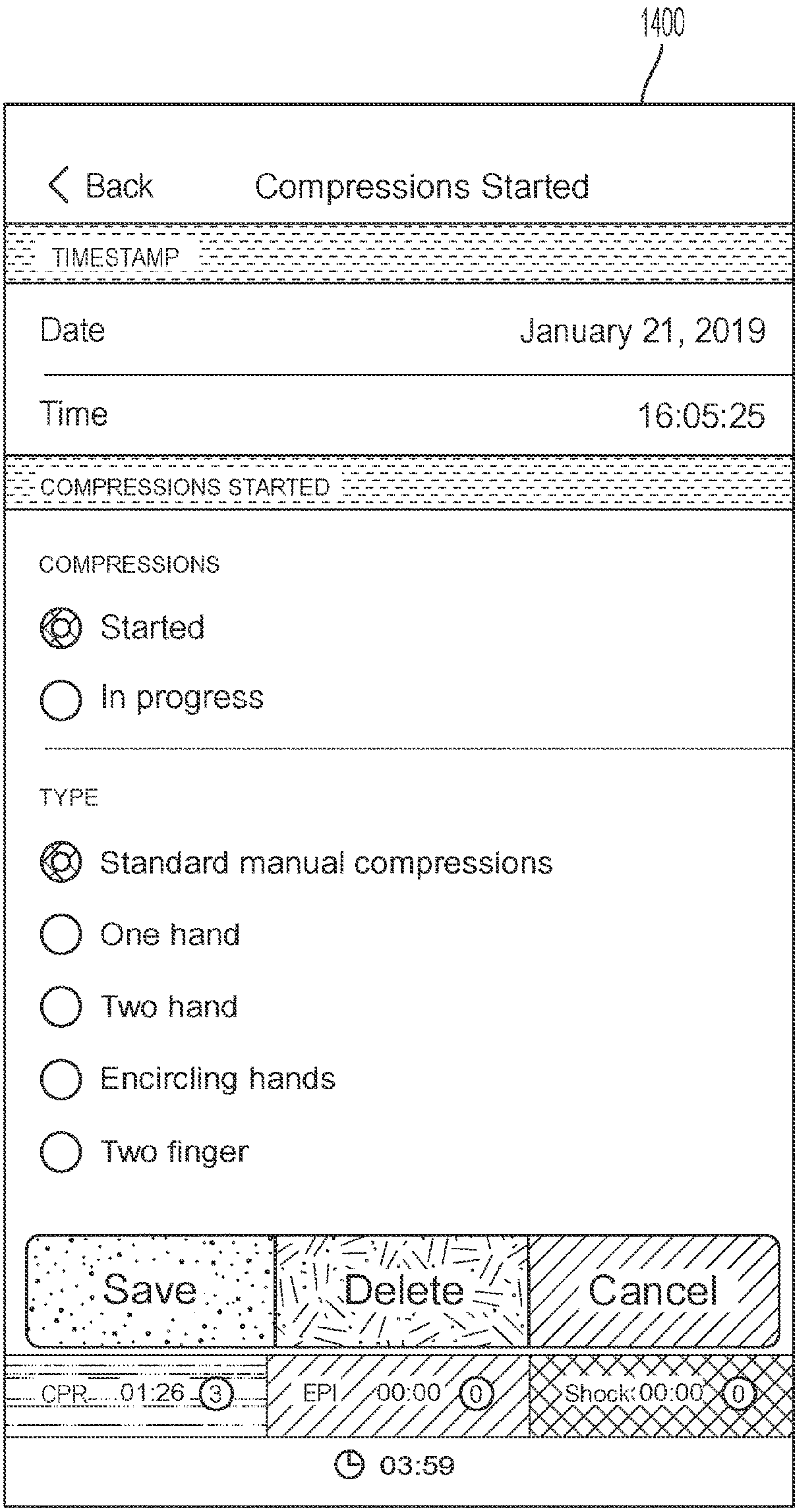
FIG. 14 is a view of a cardiopulmonary resuscitation (CPR) screen provided by an event log application in pediatric mode in accordance with at least one example disclosed herein.
Figure 15:
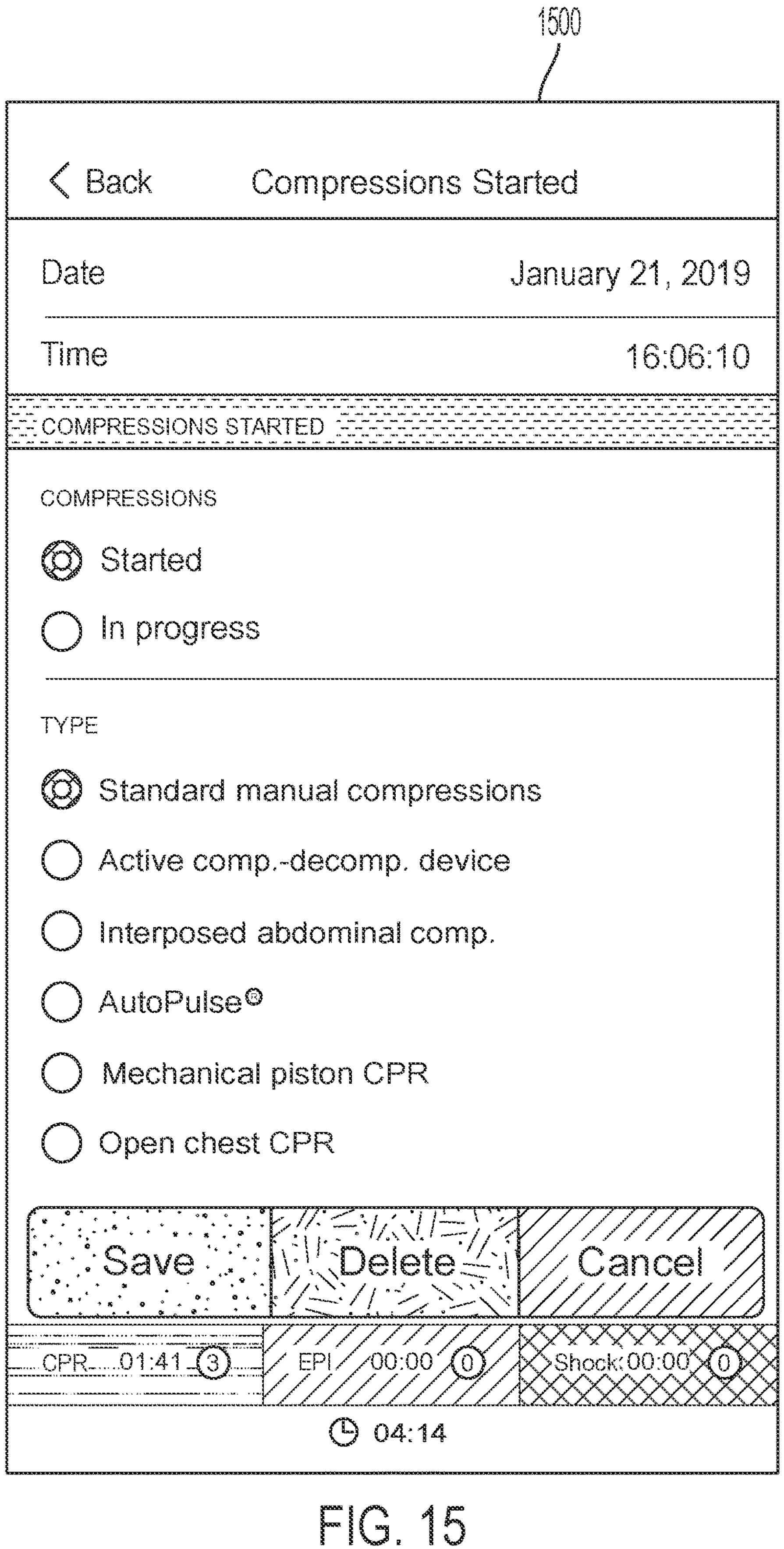
FIG. 15 is a view of the CPR screen provided by an event log application in adult mode in accordance with at least one example disclosed herein.

Returning to the alterations produced by the adult/pediatric mode of the event log application, FIGS. 14 and 15 depict CPR screens 1400 and 1500, either of which may be provided in response to selection of the CPR entry control within a code log, in some examples. More specifically, the CPR screen 1400 is displayed where the event log application is executing in pediatric mode, and the CPR screen 1500 is displayed where the event log application is executing in adult mode. Both of CPR screens 1400 and 1500 include a set of controls that enable the user to select a type parameter for the CPR being documented. However, as shown, the labels and associated values for the type parameters vary. The CPR screen 1400 includes types of CPR that are typically administered to children while the CPR screen 1500 includes types of CPR that are typically administered to adults.

Figure 16:
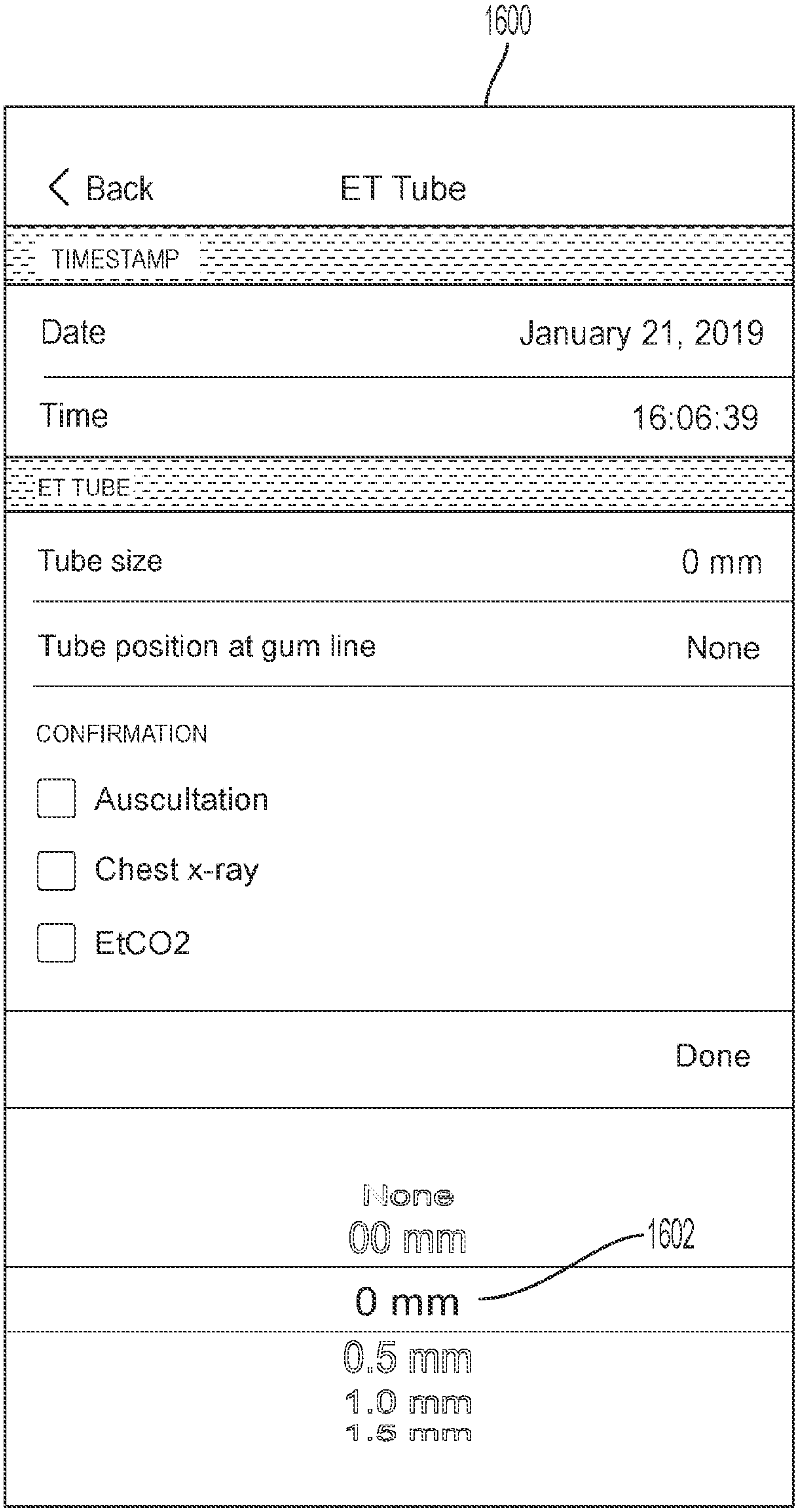
FIG. 16 is a view of an endotracheal (ET) tube screen provided by an event log application in pediatric mode in accordance with at least one example disclosed herein.
Figure 17:
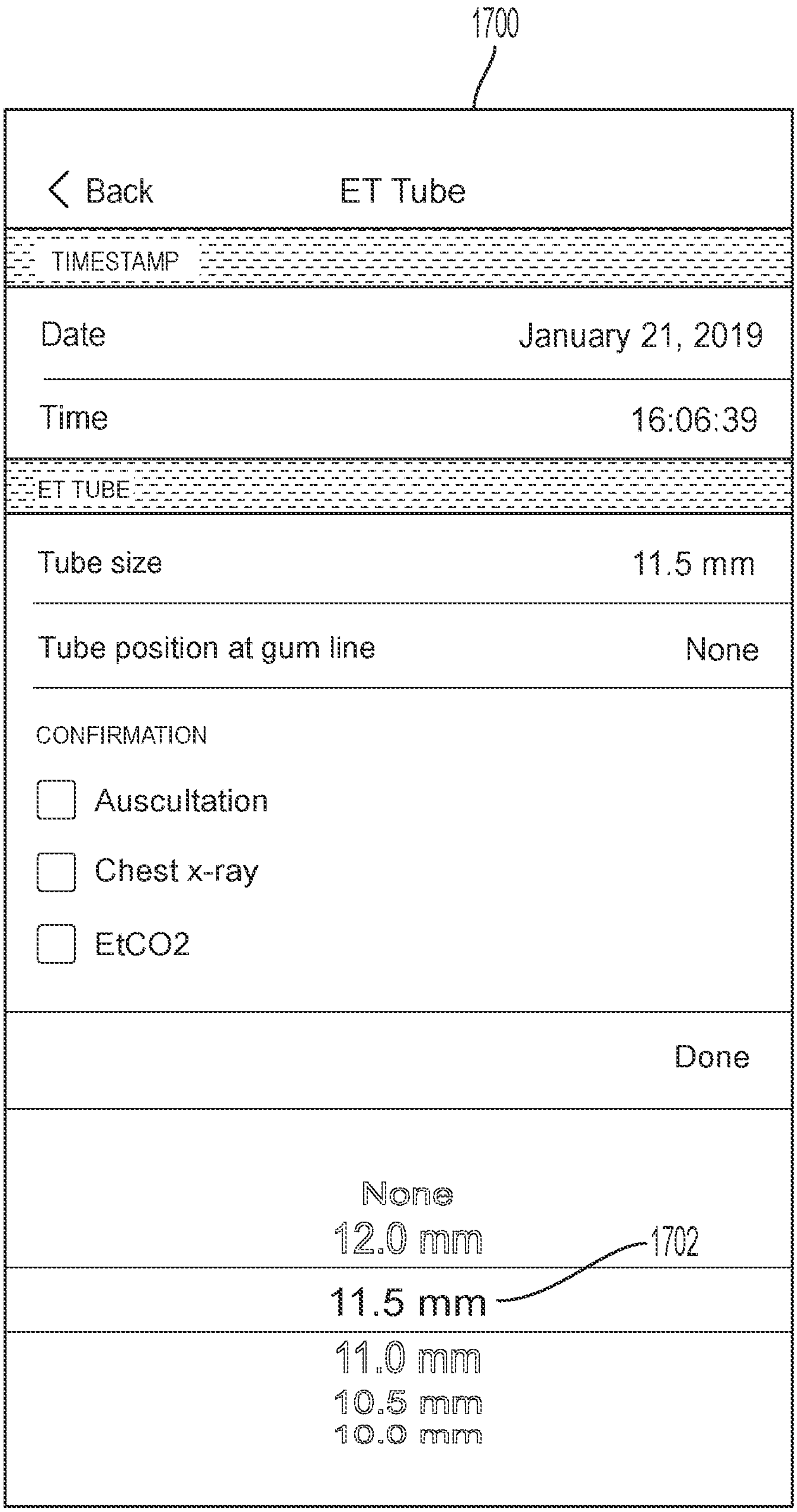
FIG. 17 is a view of the ET tube screen provided by an event log application in adult mode in accordance with at least one example disclosed herein.

Continuing the description of alterations produced by the adult/pediatric mode of the event log application, FIGS. 16 and 17 depict ET tube screens 1600 and 1700, either of which may be provided in response to selection of the ET tube entry control within a code log, in some examples. More specifically, the ET tube screen 1600 is displayed where the event log application is executing in pediatric mode, and the ET tube screen 1700 is displayed where the event log application is executing in adult mode. Both of ET tube screens 1600 and 1700 include respective controls 1602 and 1702 that enable the user to select a size parameter for the ET tube being documented. However, as shown, the labels and associated values for the type parameters are listed in different orders. The ET tubes screen 1600 lists sizes of ET tubes from smallest to largest to facilitate selections for children while the ET tube screen 1700 lists sizes of ET tubes from largest to smallest to facilitate selections for adults.

Figure 18:
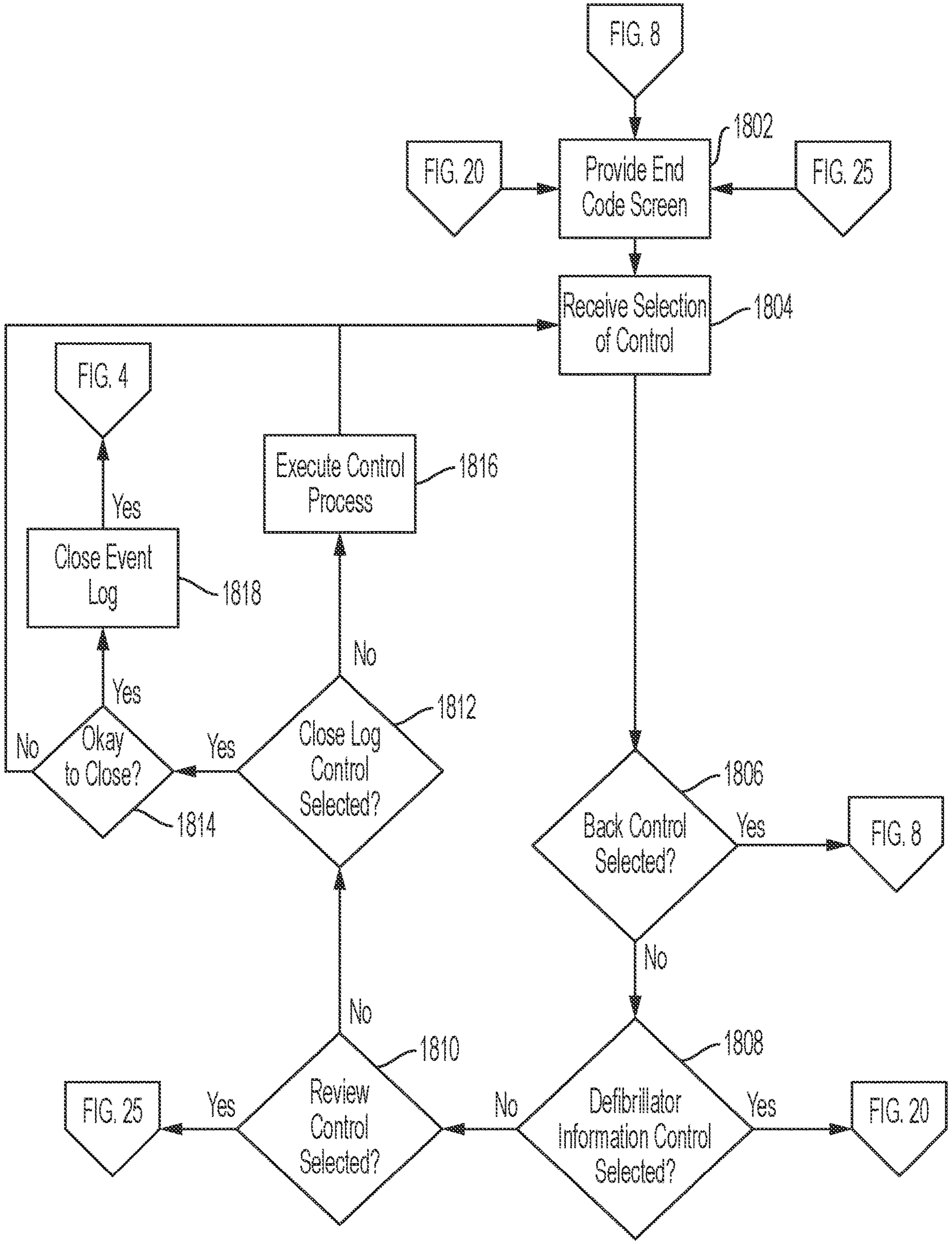
FIG. 18 is a flow diagram illustrating another portion of a process of generating log entries in accordance with at least one example disclosed herein.
Figure 19:
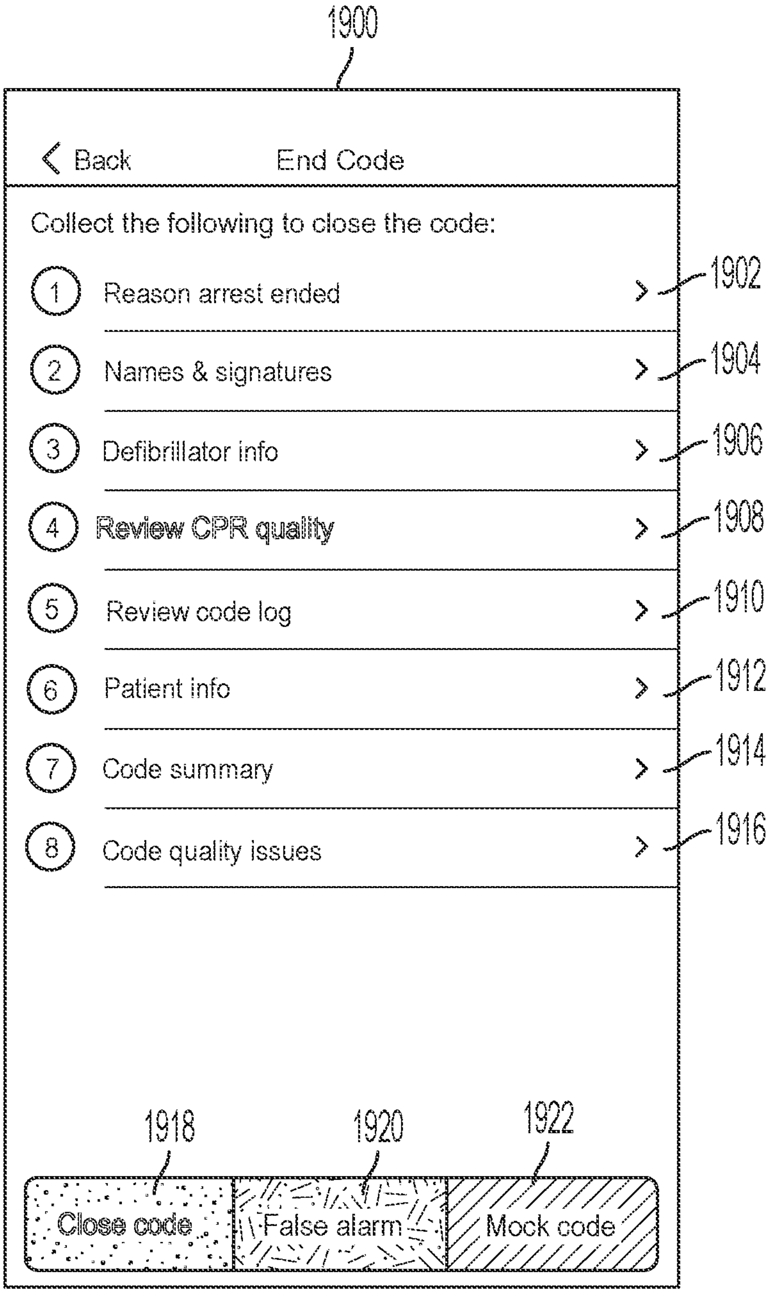
FIG. 19 is a view of an end code screen provided by an event log application in accordance with at least one example disclosed herein.

Returning to the log generation process 400 with reference to FIGS. 8 and 18, if the event log application determines 806 that the end code control 904 was selected, the event log application provides 1802 an end code screen, such as the end code screen 1900 illustrated in FIG. 19. As shown in FIG. 19, the end code screen 1900 includes a reason control 1902, a signatures control 1904, a defibrillator information control 1906, a CPR quality control 1908, a review control 1910, a patient information control 1912, a code summary control 1914, a quality issues control 1916, and a set of three close code controls (i.e., close code control 1918, false alarm control 1920, and mock code control 1922).

Next, the event log application receives 1804 input selecting a control from the end code screen 1900. Using this input, the event log application determines 1806 whether the back control was selected. If the back control was selected, the event log application provides 802 the event log screen. If the back control was not selected, the event log application determines 1808 whether the defibrillator information control 1906 was selected.

Figure 20:
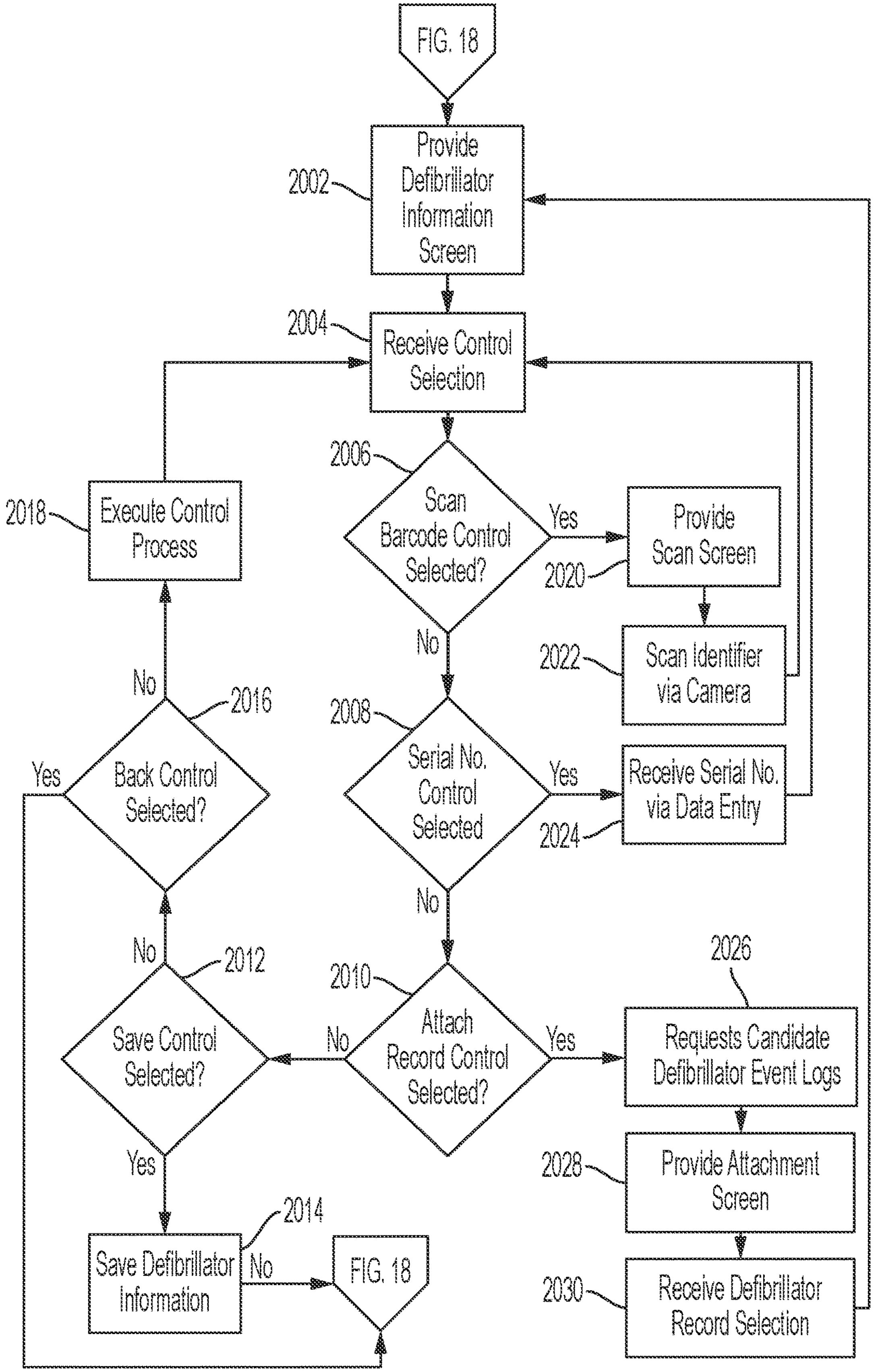
FIG. 20 is a flow diagram illustrating another portion of a process of generating log entries in accordance with at least one example disclosed herein.
Figure 21:
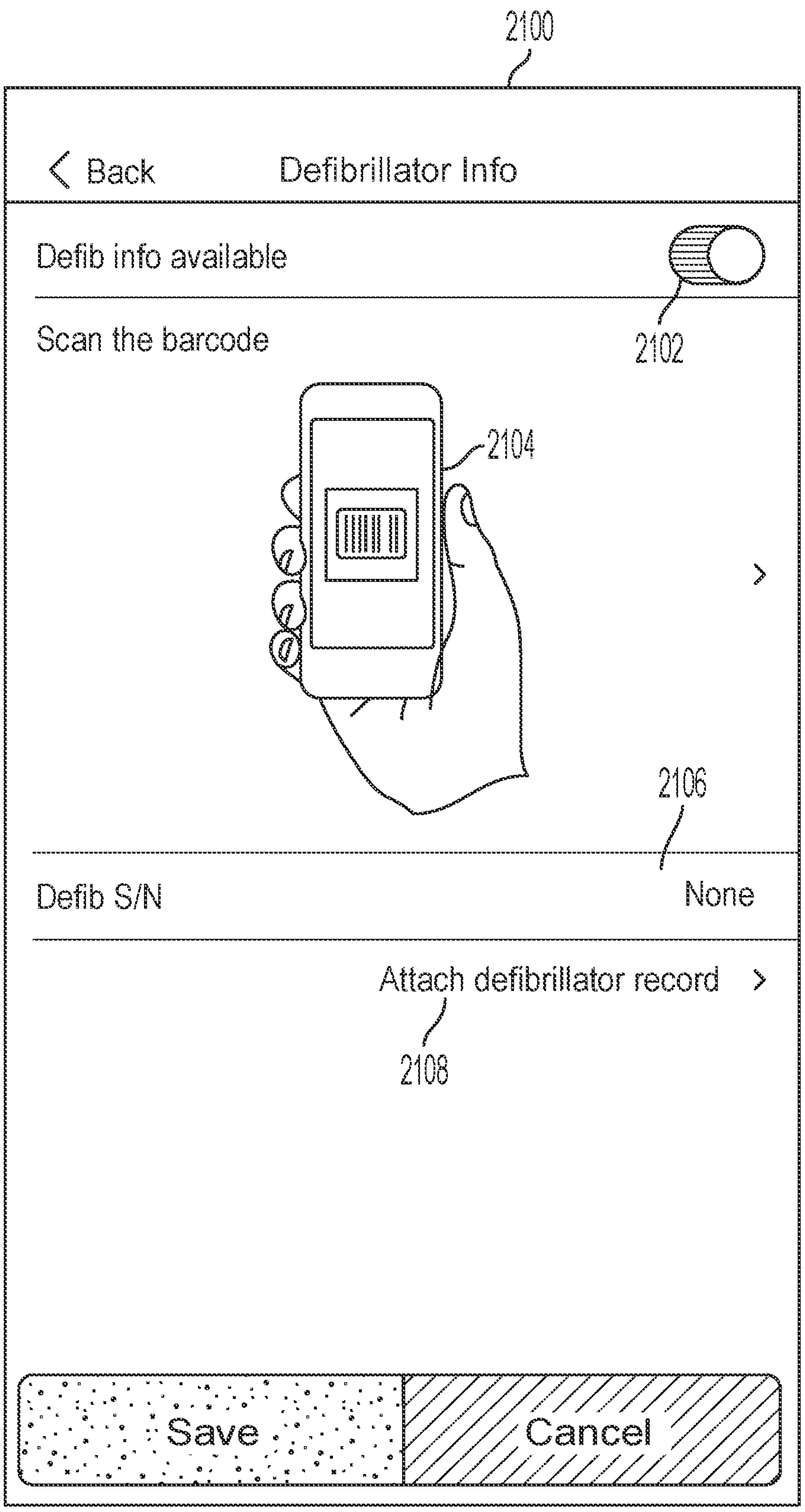
FIG. 21 is a view of a defibrillator information screen provided by an event log application in accordance with at least one example disclosed herein.

With combined reference to FIGS. 18 and 20, if the defibrillator information control 1906 was selected, the event log application provides 2002 a defibrillator information screen, such as the defibrillator information screen 2100 illustrated in FIG. 21. As shown in FIG. 21, the defibrillator information screen 2100 includes an availability control 2102, a scan control 2104, a serial number control 2106, and an attach defibrillator record control 2108.

Figure 22:
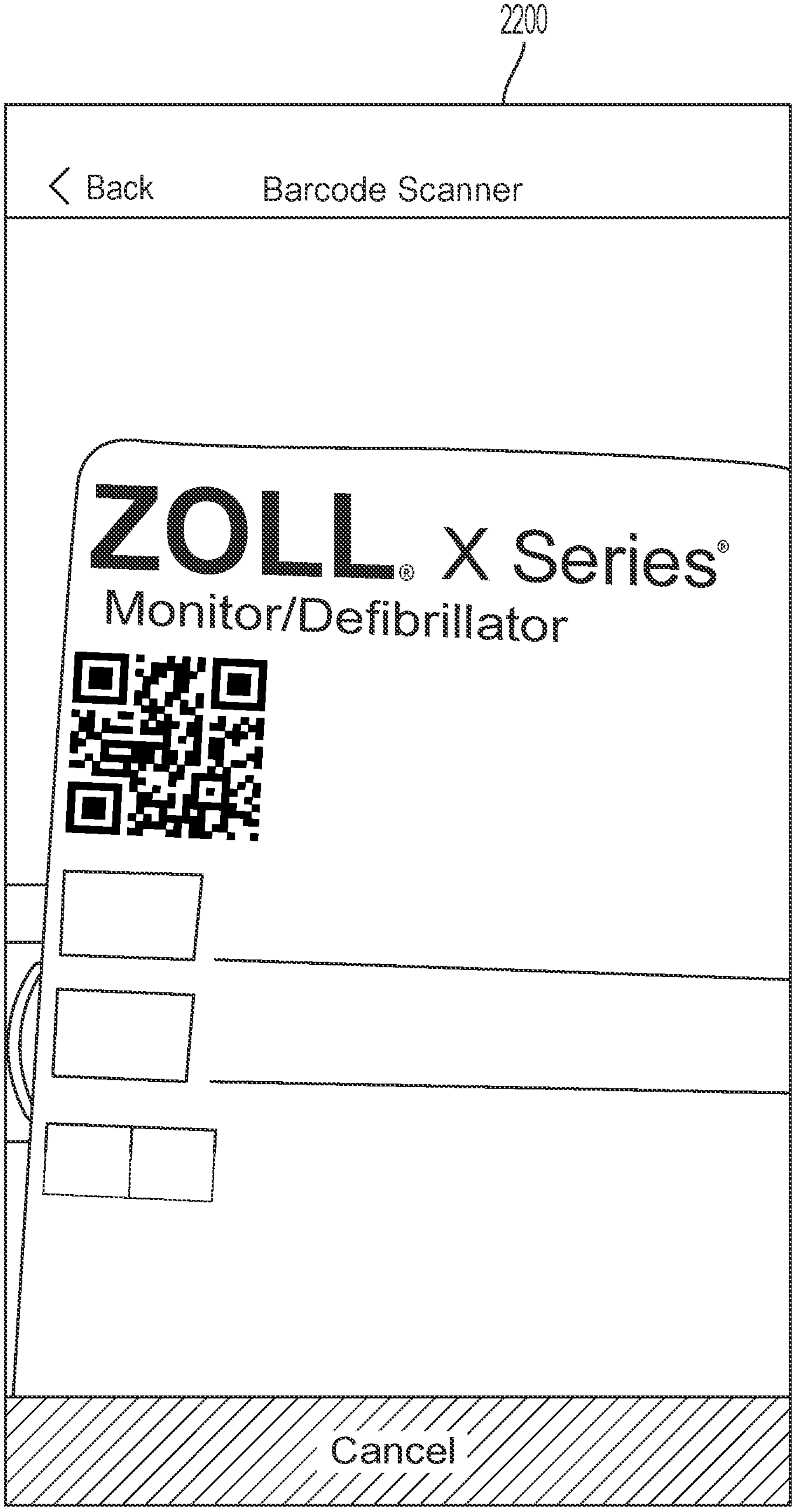
FIG. 22 is a view of a barcode scanning screen provided by an event log application in accordance with at least one example disclosed herein.

Next, the event log application receives 2004 input selecting a control from the defibrillator information screen 2100. The event log application determines 2006 whether the scan control 2104 was selected. If the scan control 2104 was selected, the event log application provides 2020 a scan screen, such as the scan screen 2200 illustrated in FIG. 22. As shown in FIG. 22 the scan screen 2200 includes an image control, a back control, and a cancel control. In response to receiving input selecting the back control or cancel control, the event log application returns to the defibrillator screen. The event log application accesses a camera included in the mobile computing devices and displays images acquire via the camera in the image control. The event log application attempts to identify and decode a barcode or some other fiducial (e.g. a QR code) depicted in an acquired image. If the event log application is successful in scanning 2022 an identifier (e.g., a serial number) of the defibrillator via the camera, the event log application returns to the defibrillator information screen 2100 and monitors for receipt 2004 of input selecting a control.

In some examples, the event log application is configured to acquire the identifier of the defibrillator via other signals, such as audio or radio frequency signals. In these and other examples, the defibrillator may include one or more of an NFC tag, an RFID tag, a barcode, and a QR code.

If the scan control 2104 was not selected, the event log application determines 2008 whether the serial number control 2106 was selected. If the serial number control 2106 was selected, the event log application displays a data entry control to receive 2024 alphanumeric input specifying the serial number of the defibrillator and returns to monitoring for receipt 2004 of input selecting a control.

Figure 23:
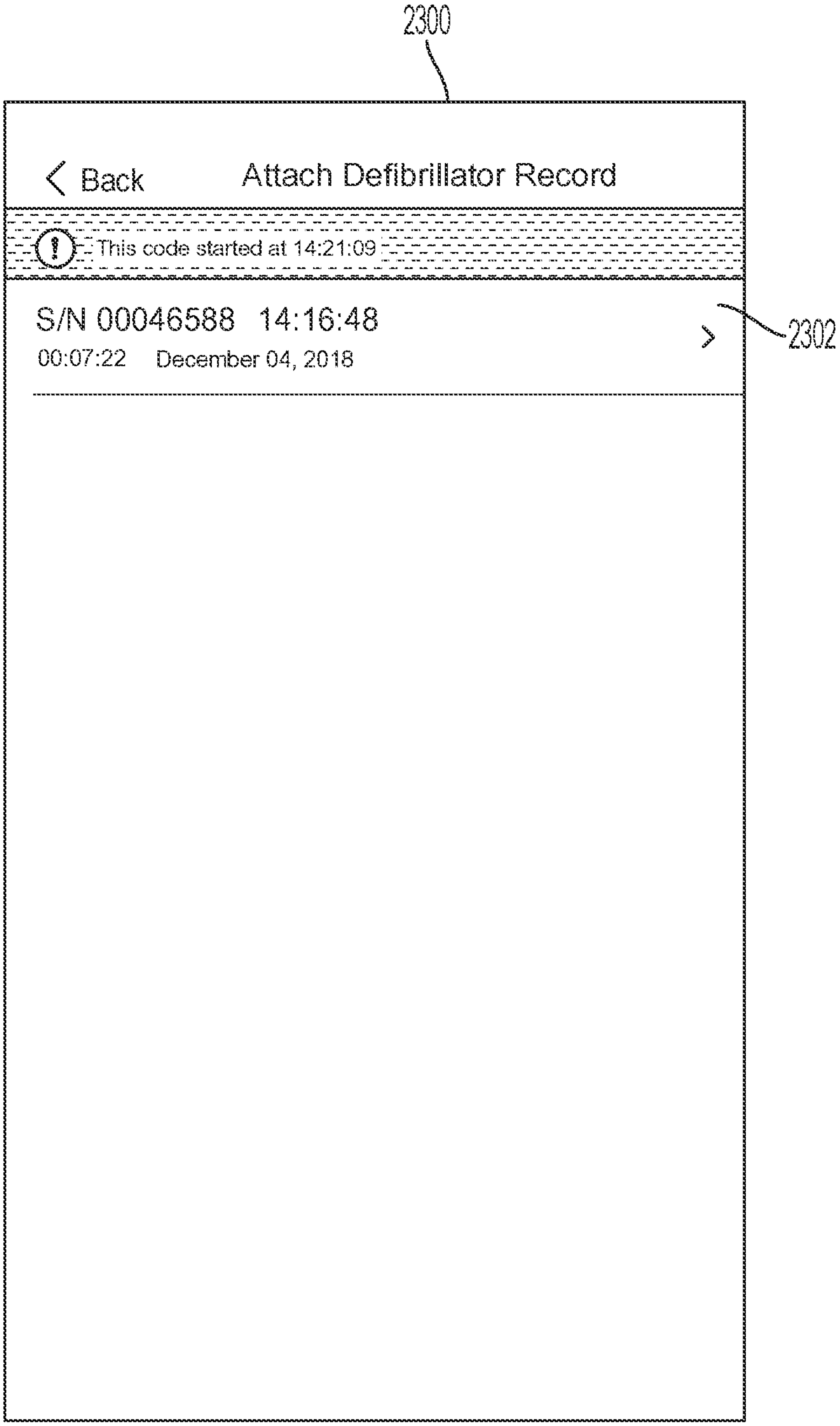
FIG. 23 is a view of an attach defibrillator record screen provided by an event log application in accordance with at least one example disclosed herein.
Figure 24:
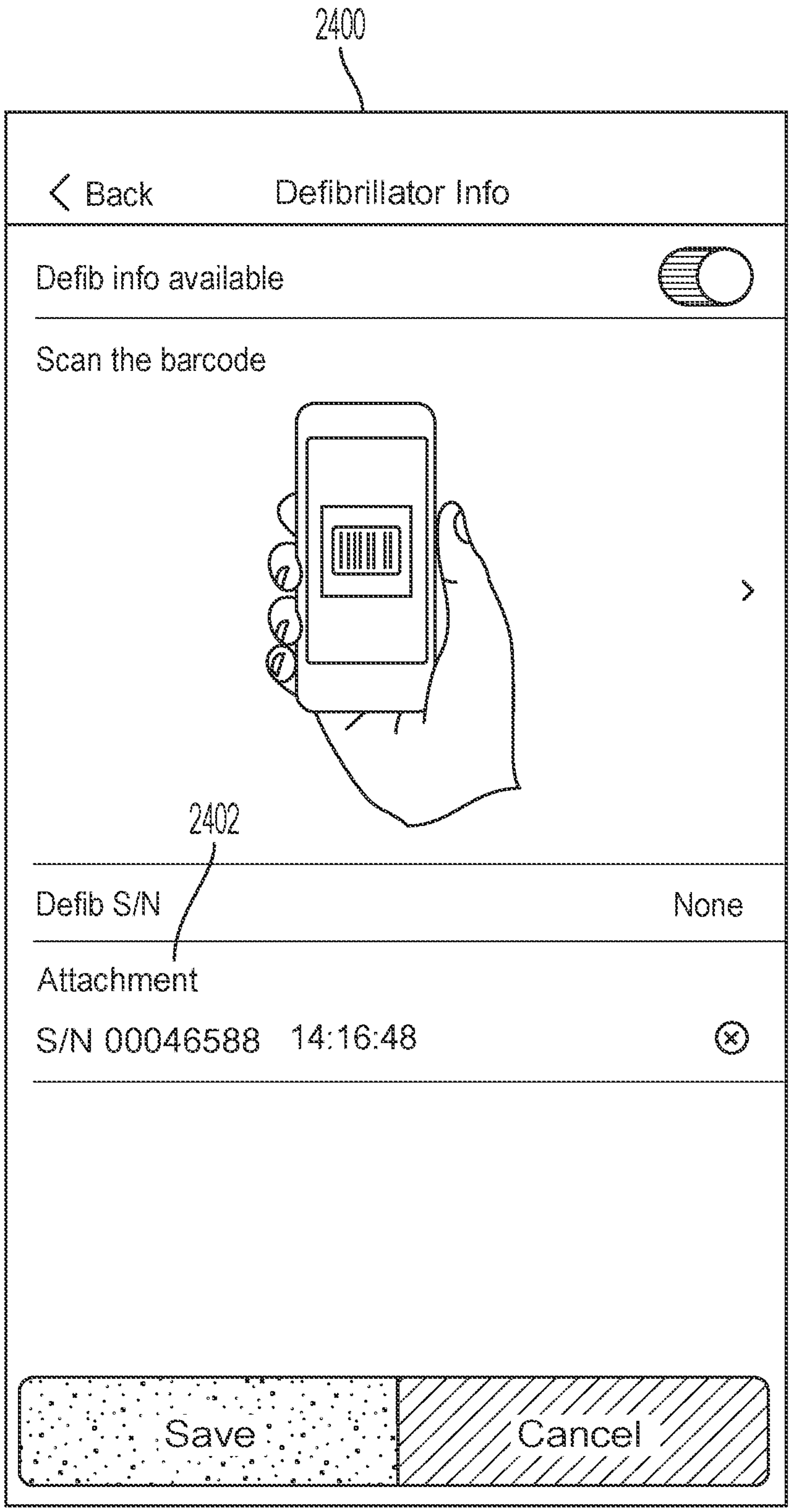
FIG. 24 is a view of another defibrillator information screen provided by an event log application in accordance with at least one example disclosed herein.

If the serial number control 2106 was not selected, the event log application determines 2010 whether the attach defibrillator record control 2108 was selected. If the attach defibrillator record control 2108 was selected, the event log application requests 2026 candidate defibrillator event logs via the event log API. This request for candidate defibrillator event logs can include a date/time stamp associated with the code and/or any identifier of the defibrillator previously collected via the scan control 2104 and/or the serial number control 2106. In response to receiving one or more candidate defibrillator event logs from the event log API, the event log application provides 2028 an attachment screen, such as the attach defibrillator record screen 2300. The attach defibrillator record screen 2300 includes a set of record controls. Each record control of the set is associated and labeled with an identifier of a candidate defibrillator event log. As illustrated in FIG. 23, the record control 2302 is associated with a candidate defibrillator event log from defibrillator serial number 00046588, which has a recorded a start time of 14:16:48. In response to receiving 2030 input selecting the record control 2302, the event log application returns to the defibrillator information screen 2100 and replaces the attach defibrillator record control 2108 with the attachment control 2402 as illustrated in defibrillator information screen 2400 of FIG. 24. In response to receiving input selecting the save control, the event log application stores the attached defibrillator event log, and associated metadata, in local storage. In certain embodiments, the metadata associated with the defibrillator event log can include metrics descriptive of the quality of the CPR monitored by the defibrillator. These metrics can include, for example, average compression depth, average compression rate, a compression quality percentage, average ventilation tidal volume, average ventilation rate, and a ventilation quality percentage. Where the metadata associated with the defibrillator event log is available, the event log application enables the CPR quality control 1908 for selection and review by the healthcare provider, as described further below.

If the attach defibrillator record control 2108 was not selected, the event log application determines 2012 whether the save control was selected. If the save control was selected, the event log application saves 2014 the defibrillator information currently reflected in the defibrillator information screen and provides 1802 the end code screen 1900.

If the save control was not selected, the event log application determines 2016 whether the back control was selected. If the back control was selected, the event log application provides 1802 the end code screen 1900.

If the back control was not selected, the event log application executes 2018 a process associated with the selected control. For instance, if the cancel control was selected, the event log application provides 1802 the end code screen 1900. However, if the availability control 2102 was selected, the event log application deactivates the controls included in the defibrillator information screen 2100 other than the availability control 2102 and records the defibrillator information control 1906 as having been addressed by the healthcare provider.

Figure 25:
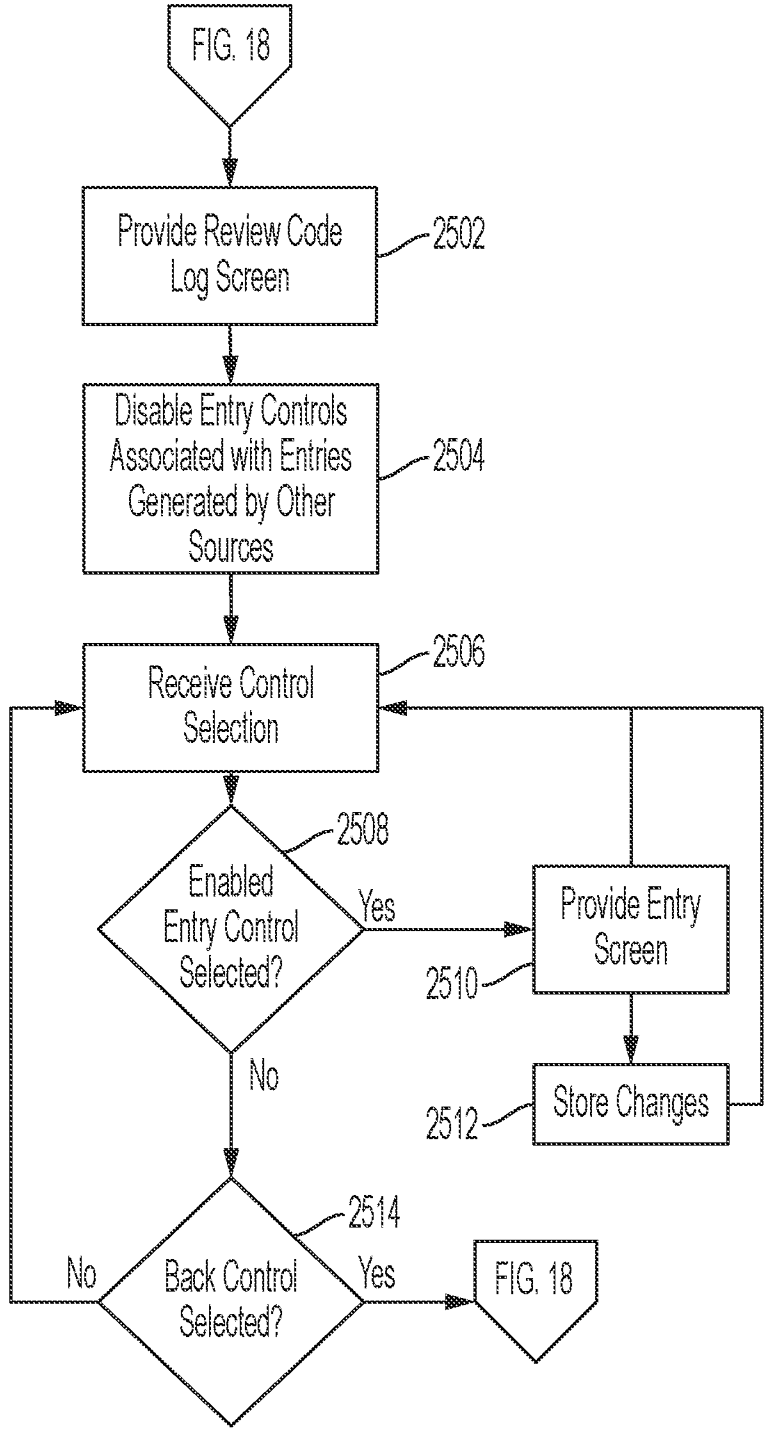
FIG. 25 is a flow diagram illustrating another portion of a process of generating log entries in accordance with at least one example disclosed herein.
Figure 26:
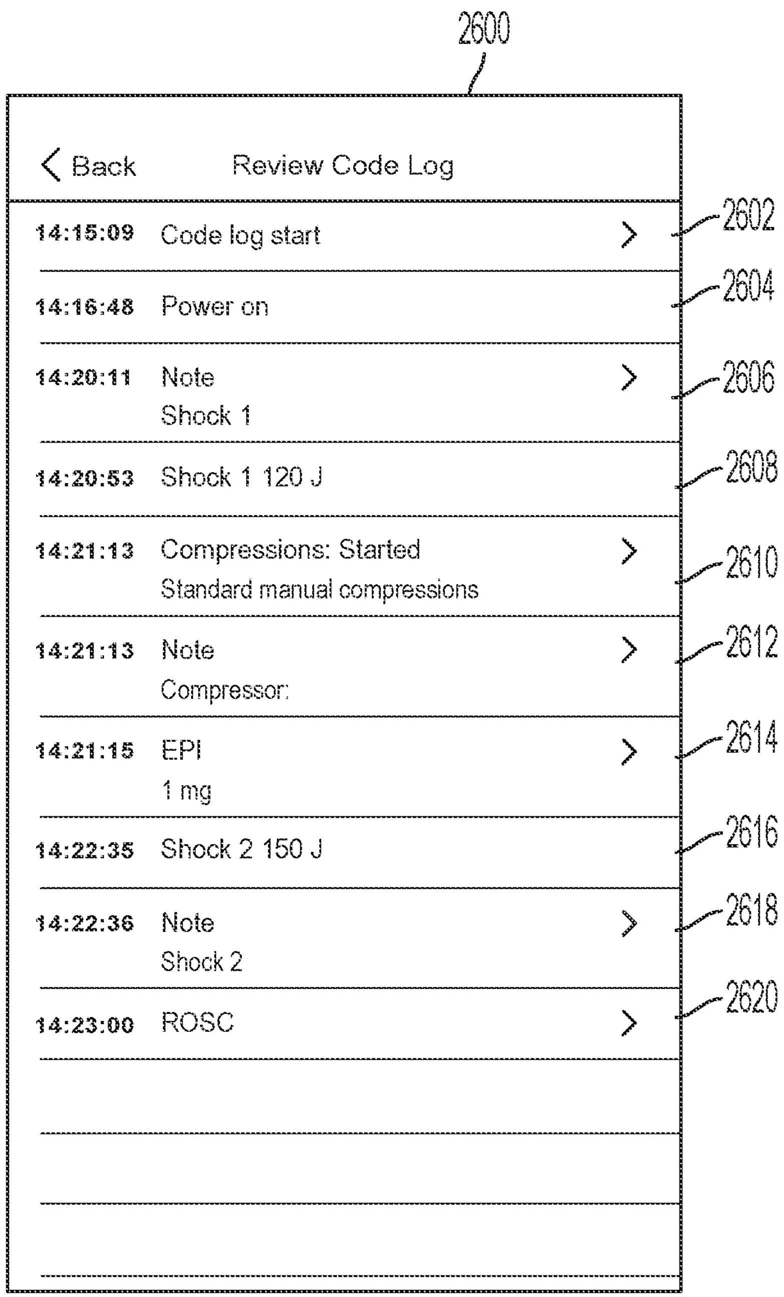
FIG. 26 is a view of a review code log screen provided by an event log application in accordance with at least one example disclosed herein.

Returning to the log generation process 400 with reference to FIGS. 18 and 25, if the defibrillator information control 1906 was not selected, the event log application determines 1810 whether the review control 1910 was selected. If the review control 1910 was selected, the event log application provides 2502 a review code log screen, such as the review code log screen 2600. The review code log screen 2600 can be used to review event logs from a single source and/or consolidated event logs from multiple sources. As shown in FIG. 26, the review code log screen 2600 includes a set of entry controls 2602-2620 that each are associated with an entry in the event log for the code. More specifically, entry controls 2602, 2606, 2610-2614, 2618, and 2620 are associated with entries that generated by the event log application. Each of these entries is identified within a consolidated event log as being input by a user, and thus each entry is editable and/or able to be deleted via its associated entry control. Entry controls 2604, 2608, and 2616 are associated with entries generated by a medical device (e.g., the medical device 104), such as a defibrillator. Each of these entries is identified within a consolidated event log as being generated by a device, and thus each entry is not editable and/or not able to be deleted via its associated entry control. It should be noted that as part of providing 2502 the review code log screen, the event log application can enable all entry controls associated with entries generated by the event log application to receive input and store modifications to the entries. Alternatively or additionally, as part of providing 2502 the review code log screen, the event log application can enable all entry controls associated with entries generated by sources other than the event log application to receive input, but not to store modifications to the entries. This semi-enabled state allows the review code log screen 2600 to at least partially respond to the user, thereby avoiding the appearance of being completely non-functional and in need of a restart.

Next, the event log application disables 2504 all entry controls on the review code log screen 2600 associated with entries generated by sources other than the event log application. The event log application receives 2506 input selecting a control from the review code log screen 2600. The event log application determines 2508 if the selected control is an enabled entry control, such as one of entry controls 2602, 2606, 2610-2614, 2618, and 2620. If the selected control is an enabled entry control, the event log application provides 2510 an edit entry screen that includes edit controls to receive changes to the entry displayed in the edit entry screen. This edit entry screen may be a version of the review code log screen 2600 that allows for in place editing of the entry. Alternatively or additionally, the edit entry screen may be a newly presented screen distinct from the review code long screen 2600. FIGS. 14-17 illustrate examples of edit entry screens. Next, in response to receiving input indicating that the healthcare provider wishes to save changes made to the entry via the edit controls, the event log application stores 2512 the changes and monitors for receipt 2506 of input selecting a control. It should be noted that disabling 2504 all of the entry controls on associated with entries generate by other sources is optional. As such, in some examples, the event log application maintains these controls in a semi-enable state or enables these controls to receive input and store modifications. Additionally or alternatively, in some examples, the event log application prompts for confirmation before storing modifications to these controls.

If an enabled entry control is not selected, the event log application determines 2514 whether the back control was selected. If the back control was selected, the event log application provides 1802, the end code screen 1900. If the back control was not selected, the event log application monitors for receipt 2506 of input selected a control of the review code log screen.

In some examples, the event log application provides no indication in response to selection of a disabled entry control. However, in other examples, the event log application provides an indication (flash, highlight, color change, series of color and/or shading changes) to indicate that the disabled entry control was selected.

Returning to the log generation process 400 with reference to FIG. 18, the event log application determines 1812 whether any of the set of three close code controls (i.e., close code control 1918, false alarm control 1920, and mock code control 1922) was selected. If a close control was not selected, the event log application executes 1816 a process associated with the selected control.

For instance, where the selected control is the reason control 1902, the event log application provides a screen that includes a set of reason controls. Each reason control of the set is associated and labeled with a particular reason the cardiac arrest ended. In response to receiving input selecting a reason control of the set of reason controls, the event log application displays additional date and time controls to receive input indicating the date and time that the cardiac arrest ended. In response to receiving input indicating the healthcare provider wishes to save this reason information, the event log application creates and stores metadata associated with the event log that specifies the reason, date, and time that the cardiac arrest ended. Examples of reasons that may be associated with reason controls by the event log application include that the patient died and had an advance directive, that the patient died and efforts were terminated due to no sustained ROSC, that the patient died and it was medically futile to continue, that the patient died and there were restrictions placed on CPR by the family, that the patient survived and had a ROSC, and that the reason the arrest ended is unknown.

Where the selected control is the signatures control 1904, the event log application provides a signatures screen that includes a set of signature controls. Each signature control of the set is associated and labeled with a particular role assumed by a healthcare provider during the code. In response to receiving input selecting a signature control of the set of signature controls, the event log application provides a follow-up screen with controls to receive text names and touch drawn signatures of the healthcare provider who acted in the associated role. In response to receiving input specifying the text name and/or signature of the person who acted in the role associated with the signature control and input confirming the healthcare provider wishes to save the signature information, the event log application creates and stores metadata associated with the event log that specifies the role, person, and name/signature. Examples of roles that may be associated with signature controls by the event log application include physician leader, recorder, anesthesiologist/certified registered nurse anesthetist, pharmacist, physician attending, respiratory care practitioner, resident, registered nurse, and other.

In some examples, the signatures screen includes a control that indicates whether signature information is available. In response to receiving input indicating that signature information is not available via this control, the event log application deactivates the set of signature controls and records the signature control as having been addressed by the healthcare provider. Additionally or alternatively, in some examples, the signatures screen includes a scan control (similar to the scan control 2104) that enables the event log application to identify individuals who assumed particular roles via RFID or Bluetooth LE devices identifying the individuals or biomarkers (e.g., via recognition of a healthcare providers face, identification of fingerprints, etc.).

Where the selected control is the code summary control 1914, the event log application provides a screen that includes a set of summary controls. Each summary control of the set is associated and labeled with a particular element of summary information regarding the code. In response to receiving input selecting a summary control of the set of summary controls, any parameters associated with the summary control, and confirmation that the healthcare provider wishes to save the entered summary information, the event log application creates and stores metadata associated with the event log that specifies the element of summary information associated with the summary control. Examples of elements of summary information that may be associated with summary controls by the event log application include the date/time that the rapid response team and/or code team was paged, the location to which the rapid response team and/or code team was paged, whether the cardiac arrest was witnessed, the type of first pulseless rhythm observed, whether family was present, the location to which the patient was transferred after the cardiac arrest ended, whether the attending physician was notified, and whether communications was notified.

In some examples, the event log application responds to selection of certain summary controls by providing a follow-up screen that includes controls that allow input of specific parameters associated with the selected element of summary information. In these examples, the event log application records the parameters along with the log entry.

Examples of parameters that can be associated with a log entry documenting the location to which the rapid response team and/or code team was paged include the emergency room, the intensive care unit, the pediatric intensive care unit, radiology, and a custom location specified by free form text.

Examples of parameters that can be associated with a log entry documenting the location to which the patient was transferred after the cardiac arrest ended include the morgue, the intensive care unit, the pediatric intensive care unit, and a custom location specified by free form text.

Where the selected control is the quality issues control 1916, the event log application provides a quality screen that includes a set of quality controls. Each quality control of the set is associated and labeled with a category of potential issues encountered that affect the quality of the code. In response to receiving input selecting a quality control of the set of quality controls, any parameters associated with the quality control, and confirmation that the healthcare provider wishes to save the entered quality information, the event log application creates and stores metadata associated with the event log that specifies the element of quality information associated with the quality control. Examples of elements of quality information that may be associated with quality controls by the event log application include the date/time that the rapid response team and/or code team was paged, the location to which the rapid response team and/or code team was paged, whether the cardiac arrest was witnessed, the type of first pulseless rhythm observed, whether family was present, the location to which the patient was transferred after the cardiac arrest ended, whether the attending physician was notified, and whether communications was notified.

In some examples, the event log application responds to selection of certain quality controls by providing a follow-up screen that includes controls that allow input of specific parameters associated with the selected element of quality information. In these examples, the event log application records the parameters along with the log entry.

Examples of parameters that can be associated with a log entry documenting the location to which the rapid response team and/or code team was paged include the emergency room, the intensive care unit, the pediatric intensive care unit, radiology, and a custom location specified by free form text.

Examples of parameters that can be associated with a log entry documenting the location to which the patient was transferred after the cardiac arrest ended include the morgue, the intensive care unit, the pediatric intensive care unit, and a custom location specified by free form text.

Figure 27:
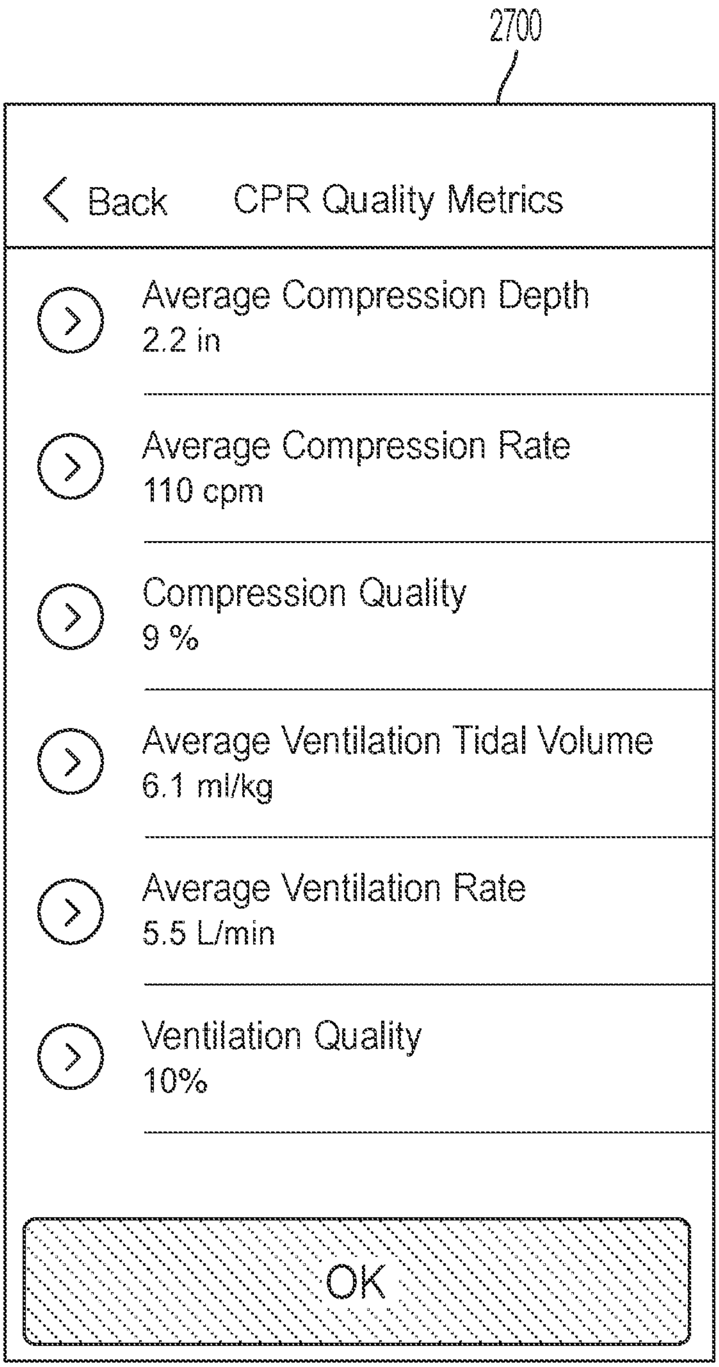
FIG. 27 is a view of a CPR quality metrics screen provided by an event log application in accordance with at least one example disclosed herein.

In some examples, the quality screen includes a control that indicates whether quality information is available. In response to receiving input indicating that quality information is not available via this control, the event log application deactivates the set of quality controls and records the code quality control as having been addressed by the healthcare provider.

Where the selected control is the CPR quality control 1908, the event log application provides a screen that includes a set of CPR metric controls, such as the CPR Quality Metrics screen 2700 illustrated in FIG. 27. Each metric control of the set is associated and labeled with a metric descriptive of CPR quality. As shown in CPR Quality Metrics screen 2700, examples of the metrics associated with the metric controls include average compression depth, average compression rate, compression quality percentage, average ventilation tidal volume, average ventilation rate, and ventilation quality percentage. The CPR quality metrics 2700 provided in FIG. 27 include information concerning the quality of performance of a rescuer in the administration of chest compressions, where the average compression depth and average compression rate are provided over the course of a resuscitation effort as measured from a motion sensor (e.g., accelerometer) placed on the sternum of the chest and connected to a monitor/defibrillator. The CPR quality metrics may also include information concerning the quality of performance of a rescuer in the administration of ventilations, where the average ventilation tidal volume and average ventilation rate are provided over the course of a resuscitation effort as measured from a flow sensor placed in the patient airway and connected to a monitor/defibrillator. The compression quality is provided as a percentage of compressions (e.g., depth and/or rate) that were performed within the specified target range(s), and the ventilation quality may be provided as a percentage of ventilations (e.g., tidal volume) that were performed within the specified target range. In some examples, such information is generated from the monitor/defibrillator, uploaded to a server (e.g., running an event log API), and downloaded into the consolidated event log record of the event log application running on the mobile computing device used for documentation.

In some examples, such information is provided directly from the monitor/defibrillator to the consolidated event log record of the event log application running on the mobile computing device used for documentation. In some examples, the information may be provided from the monitor/defibrillator after the caregivers have finished treating the patient as one of more datafiles that contain information such as physiologic, rescuer performance data, monitor/defibrillator machine state data (e.g. time of defibrillation shock and energy, pacing amplitude rate and time of start/stop), and code markers that are transmitted from the monitor/defibrillator directly to the mobile computing device running the event log application or alternatively communicated to the device running the event log application via the server.

Figure 28:
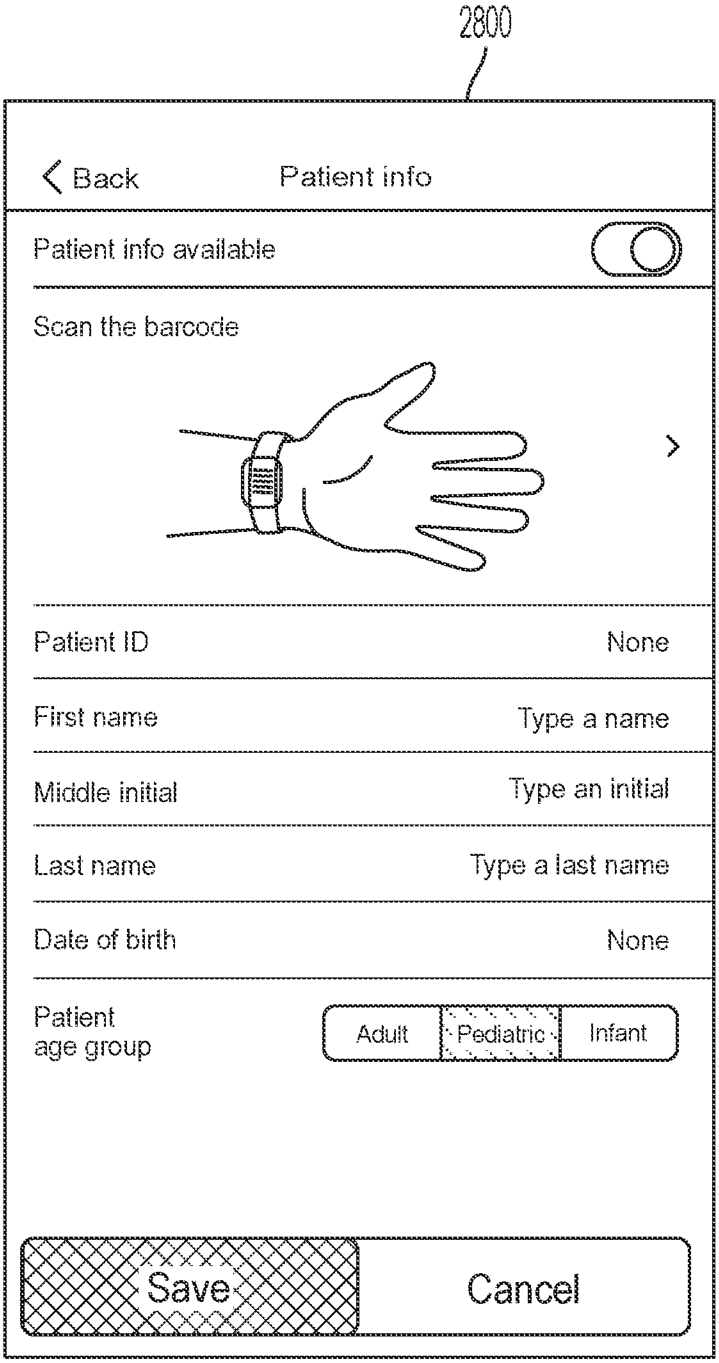
FIG. 28 is a view of a patient information screen provided by an event log application in accordance with at least one example disclosed herein.

In other examples, the information may be provided from the monitor/defibrillator to the consolidated event log record of the event log application running on the mobile computing device in real time while the patient is still being treated by the caregiver. As the data is generated by the defibrillator/monitor, it can be communicated to the mobile computing device, typically via wireless communication such as 802.11, Bluetooth, a cellular data stream, etc. Alternatively or additionally, the data can be routed, in real time, from the monitor/defibrillator to the mobile computing device via a server.

Where the selected control is the patient information control 1912, the event log application provides a screen that includes controls that enable collection of patient information, as the patient information screen 2800 illustrated in FIG. 28. As shown in FIG. 28, the controls in the patient information screen 2800 are configured to receive a unique patient identifier, a first, middle, and last name of the patient, the patient's date of birth, and the patient's age group. Similar to the defibrillator information screen 2100, the patient information screen 2800 includes a scan control to scan a patient identifier and an availability control to indicate whether patient information is available. In some examples, selection of the patient's age group sets the mode of the event log application to adult or pediatric as does the adult/pediatric control 902 described above. In response to receiving input indicating that the healthcare provider wishes to save the patient information entered via the patient information screen 2800, the event application stores the patient information with local storage in association with the event log for the code.

As with the scan control 2104 described above, in some examples the scan control used to capture a patient identifier may receive signals other than visual signals (e.g., audio signals and/or radio frequency signals). In these and other examples, the patient may wear a patient identification component (e.g., a wearable item, such as a wrist band, label, article of clothing or the like) that includes or displays one or more of an NFC tag, an RFID tag, a barcode and a QR code. Additionally or alternatively, in certain examples, the scan control of the patient information screen 2800 can be used to capture biomarkers of the patient to identify the patient. These biomarkers can include, for example, the patient's face and fingerprints to name a few.

In some examples, the event log application is configured to provide other screens similar to the patient information screen 2800 that are configured to receive information regarding materials used to treat the patient, such as medication, IV bags, intubation tubes and the like. In these examples, the medication containers, IV bags, intubation tubes, or other such items include a fiducial (e.g., a QR code or a barcode) that identifies its type and that can be scanned to acquire information regarding the medication, IV bag, intubation tube, etc. Examples of the types of information that can be acquired using a fiducial, RFID, or other proximity-based detection process include medication type and dosage, IV bag size and contents, and intubation tube size.

Returning to the log generation process 400 with reference to FIG. 18, the event log application determines 1812 whether a close log control was selected. If a close log control was selected, the event log application executes a confirmation process to determine 1814 whether the code may be closed. The particular confirmation process executed by the event log application varies depending on the particular close log control selected.

For instance, if the mock code control 1922 is selected, the event log application executes a confirmation process that requests confirmation that the healthcare provider wishes to close the code as a mock code. If the confirmation process receives confirmation, the event log application records the code as a mock code, closes 1818 the code by storing data indicative of the same in association with the event log, and provides 402 the initial screen. Similarly, if the false alarm control 1920 is selected, the event log application executes a confirmation process that requests confirmation that the healthcare provider wishes to close the code as a false alarm. If the confirmation process receives confirmation, the event log application records the code as a false alarm, closes 1818 the code, and provides 402 the initial screen. If the close code control 1918 is selected, the event log application executes a confirmation process that records the code as complete, closes 1818 the code, and provides 402 the initial screen. However, the event log application disables the close code control 1918 during provision of the end code screen 1900 and enables the close code control 1918 only if all of the controls 1902 through 1916 that are enabled have been are reviewed and addressed by the healthcare provider. If the event log application determines 1808 that the executed confirmation process did not receive confirmation, the event log application monitors for receipt 1804 of input selecting a control.

The log generation process 400 concludes after the code is closed 1818. Processes in accordance with the log generation process 400 enable a documenter, such as the healthcare provider, to efficiently create a consolidated event log that integrates entries from multiple source devices. Such consolidated event logs provide a single source of documentation that can be used to improve patient treatment protocols and execution of the same by healthcare providers.

Server-Side Log Consolidation and Analytics

Figure 29:
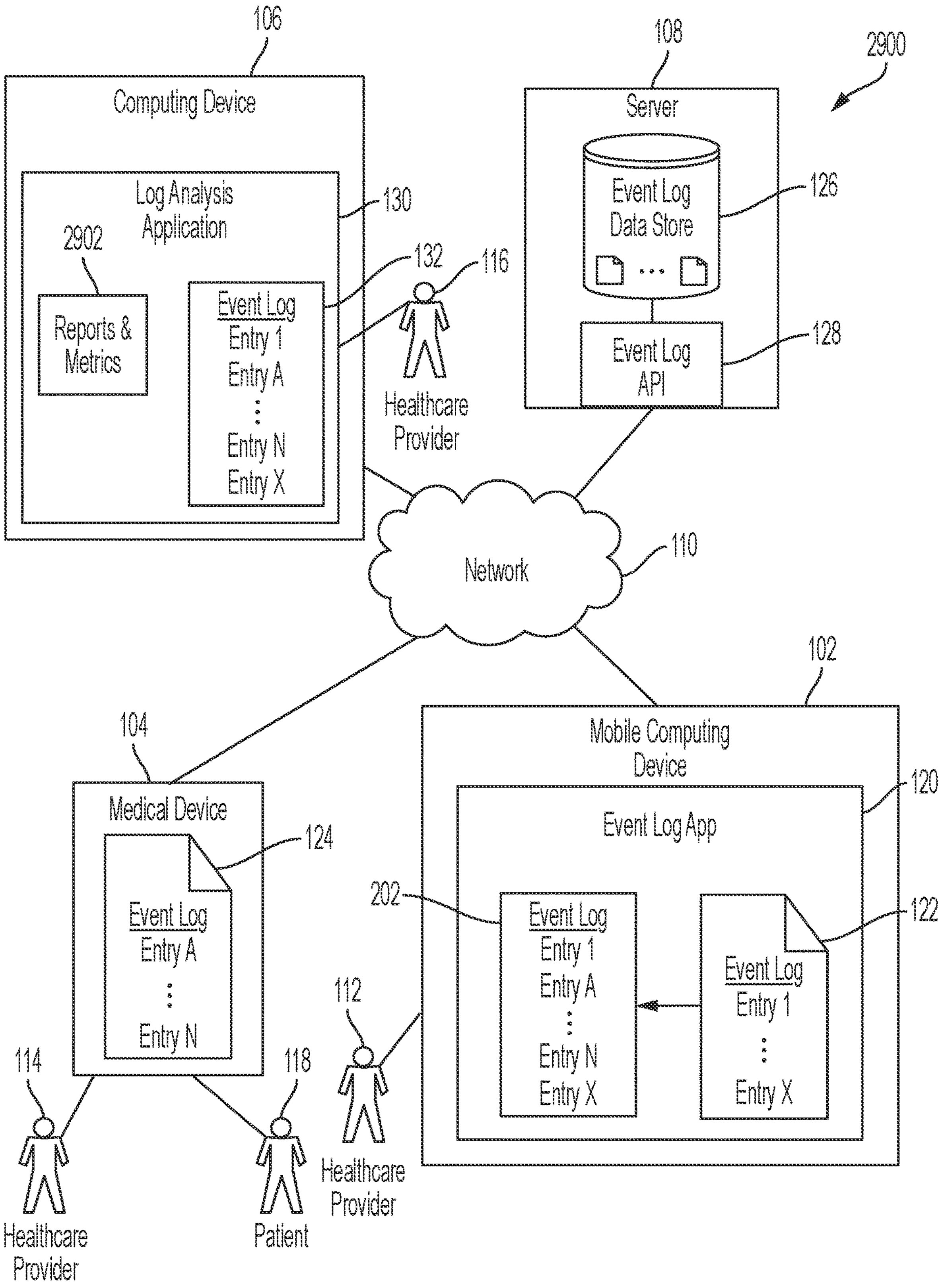
FIG. 29 is a block diagram illustrating another configuration of the distributed system of FIG. 1 in accordance with at least one example disclosed herein.

FIG. 29 illustrates a particular configuration 2900 of the distributed system 100 in which the log analysis application 130 is configured to interoperate with the event log API 128 to provide a view 132 to the healthcare provider 116. In this example, the view 132 displays an event log with entries consolidated from multiple source devices. Additionally, in this example, the log analysis application 130 implements a variety of reports 2902 that include metrics calculated from consolidated event logs stored in the event log data store 126. As shown in FIG. 29, the configuration 2900 includes the mobile computing device 102, the medical device 104, the computing device 106, the server 108, and the network 110. In operation, the configuration 2900 can be used by the healthcare provider 116 analyze consolidated event logs and metrics that summarize the same via the log analysis application 130.

As shown in FIG. 29, the view 132 is configured to provide a consolidated event log that includes entries from the event log 122 and entries from the event log 124. The view 132 provides many of the advantages of the view 202 described above with reference to FIG. 2. In certain examples, the view 132 enables modification of some entries and prevent modification of other entries, as does the view 202. Additionally or alternatively, in some examples, the view 132 enables the healthcare provider 116 to review an event log generate by the event log application and to link event logs generated by a medical device with the event log under review. In these examples, the view 132 includes one or more record controls (like the record control 2302 described above with reference to FIG. 23) that display identifiers of candidate event logs generated by the medical devices. In response to receiving input selecting a record control, the log analysis application 130 merges the candidate event log associated with the record control with the event log under review, thereby generating a consolidated event log.

In addition, as shown in FIG. 29, the reports 2902 are configured to provide insight regarding the outcomes and quality of treatment documented by the event log application 120. In some examples, the log analysis application 130 is configured to generate the reports 2902 by interoperating the server 108 via the event log API 128. In these examples, the log analysis application 130 transmits requests for reports to the event log API 128. These requests can include report criteria specifying particular filters requested for a report. In response to receiving the requests, the event log API 128 transmits a report generated with the criteria specified in the request. In some examples, to generate reports the event log API 128 executes the processing components described above with reference to FIG. 1 on-demand and in response to receiving a report request from the log analysis application 130. In some examples, the event log API 128 periodically generates and stores commonly requested reports to enable faster response times to requests. In either case, the log analysis application 130 is configured to, upon receipt of a requested report, render the report 2902 for display to the healthcare provider 116. Some examples of the reports 2902 rendered by the log analysis application 130 are described further below with reference to FIGS. 33-37.

In certain examples, the log analysis application 130 is configured to render the view 132 by interoperating the server 108 via the event log API 128. In these examples, the log analysis application 130 transmits requests for consolidated event logs to the event log API 128. These requests can include search criteria specifying particular devices, time, and/or event log identifiers associated with one or more consolidated event logs. In response to receiving the requests, the event log API 128 transmits one or more consolidated event logs that meet the search criteria. The log analysis application 130 is configured to, upon receipt of a requested consolidated event log, render the view 132 for display to the healthcare provider 116.

Figure 30:
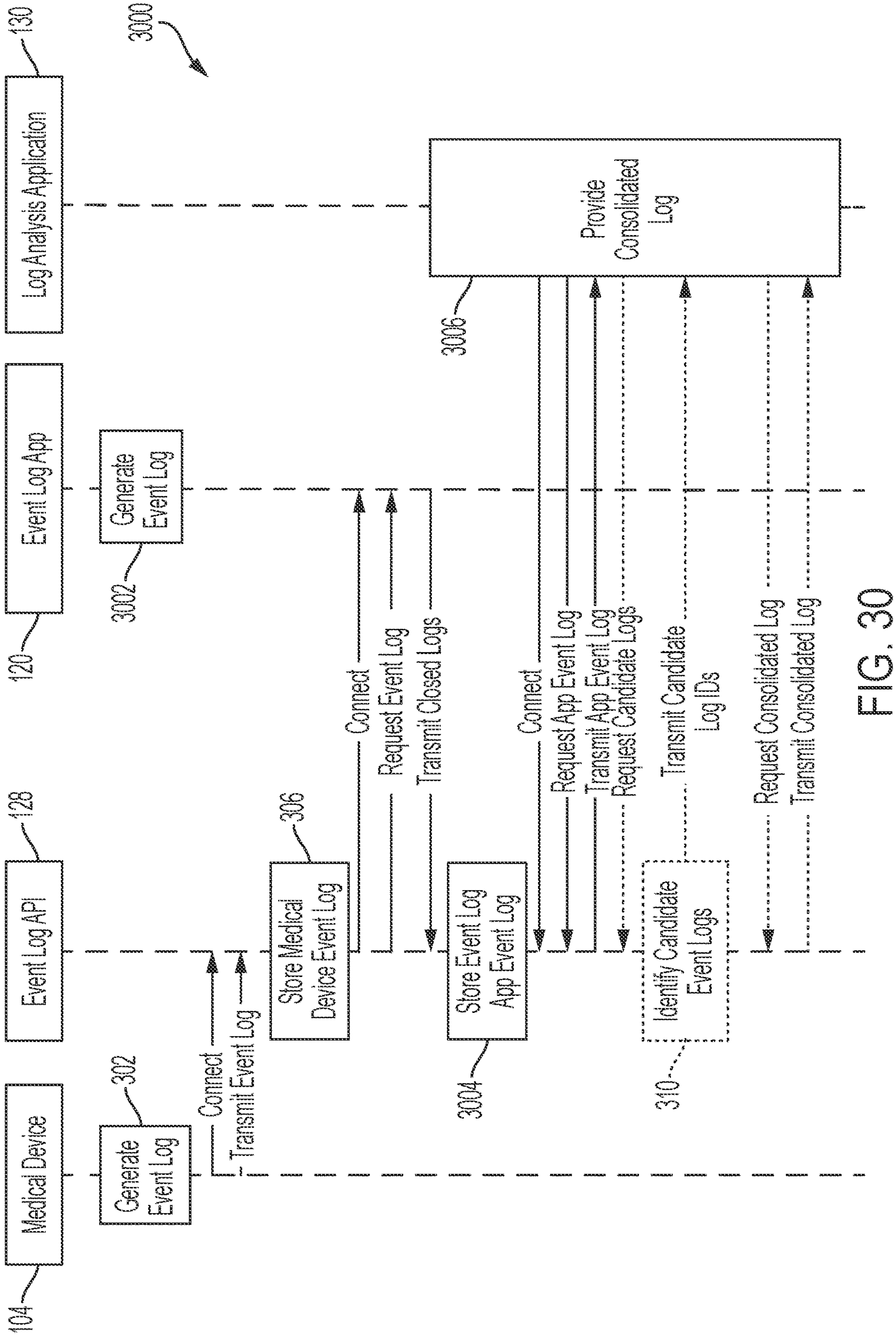
FIG. 30 is a sequence diagram illustrating another process of documenting emergency care in accordance with at least one example disclosed herein.

FIG. 30 illustrates a process 3000 for documenting emergency care that is executed by the configuration 2900 of the distributed system 100 in some examples. As shown in FIG. 30, the documentation process 3000 includes a sequence of actions that are collectively executed by a medical device (e.g., the medical device 104), an event log API (e.g., the event log API 128), an event log application (e.g., the event log application 120), and a log analysis application (e.g., the log analysis application 130).

The documentation process 3000 starts with the medical device generating 302 an event log (e.g., the event log 124) including one or more entries (e.g., the log entries A through N) as described above with reference to FIG. 3. Next, the event log application generates 3002 an associated event log (e.g., the event log 122) including one or more entries (e.g., the log entries 1 through X of the event log 122 listed in FIG. 2). Each entry generated 3002 can include a date/time stamp indicating the time at which an event documented by the entry occurred and an indicator of the event, such as a type identifier or a textual description of the event. In some examples, generation 3002 of the event log ends with the medical device receiving input from the healthcare provider indicating that treatment of the patient is complete and recording an event indicative of the same in the event log (e.g., closing the event log). These closed event logs may be isolated event logs that include entries generated solely by the event log application or by be consolidated event logs that include entries generated by the event log application and medical devices.

As shown in FIG. 3000, in response to completing generation of the event log, the medical device connects to the event log API and transmits the event log to the event log API for subsequent processing. Next, the event log API receives, parses, and stores 306 the event log generated by the medical device. In this example, the event log API further responds to the receipt of the medical device event log by connecting to the event log application and transmitting a request for one or more closed event logs. In response to receiving this request, the event log application transmits the one or more requested, closed event logs to the event log API. In this example, the event log API receives, parses, and stores 3004 the event log generated by the event log application.

Next, the log analysis application, in response to receiving input from a healthcare provider (e.g., the healthcare provider 116) requesting provision of the view 132 for a particular code, provides 3006 a consolidated event log of the code via the view 132. As part of providing 3006, the log analysis application connects to the event log API and transmits a request for an event log generated by the event log application that is associated with the code. In response, the event log API identifies this application event log and transmits the same to the log analysis application. In some examples where the log entries are stored in a relational database table, the event log API generates the application event log by executing one or more SQL queries and embedding the results of the queries within HTML formatted for the view 132. In response to receiving the requested application event log, the log analysis application renders it for presentation to the healthcare provider within the view 132. If the application event log is a consolidated event log, the documentation process 3000 concludes.

If, however, the application event log is not consolidated, the log analysis application enables an optional consolidation process to be executed as part of providing 3006 the consolidated event log. Within the consolidation process, the log analysis application, in response to receive input from the healthcare provider requesting a list of event logs that are candidates for consolidation with the application event log, transmits a request for candidate event logs. In response to receiving a request for candidate event logs, the event log API identifies 310 one or more candidate event logs for potential consolidation and transmits identifiers of the one or more candidate event logs to the log analysis application. Next, as part of the consolidation process, the log analysis application requests a consolidated event log that is associated with the code from the event log API. In some examples where the log entries are stored in a relational database table, the event log API generates the consolidated event log by executing one or more SQL queries and embedding the results of the queries within HTML formatted for the view 132. Next, the event log API transmits a copy of the request consolidated code to the log analysis application. In response to receiving the requested consolidated event log, the log analysis application renders it for presentation to the healthcare provider within the view 132, and the documentation process 3000 concludes.

Processes in accordance with the documentation process 3000 enable a documenter, such as the healthcare provider 112, to efficiently create a consolidated event log that integrates entries from multiple source devices. Such consolidated event logs provide a single source of documentation that can be used to improve patient treatment protocols and execution of the same by healthcare providers.

Figure 31:
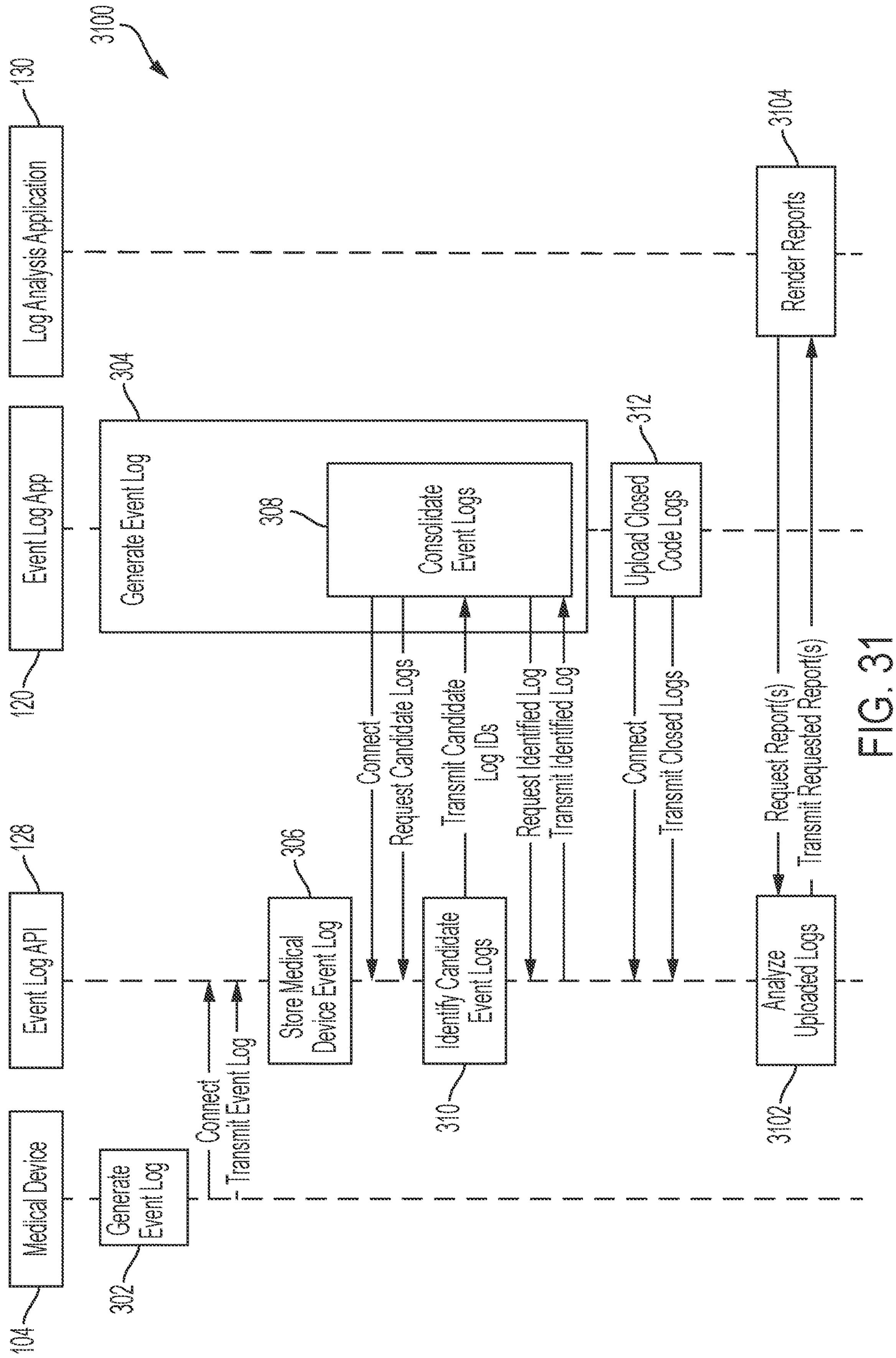
FIG. 31 is a sequence diagram illustrating another process of documenting emergency care in accordance with at least one example disclosed herein.

FIG. 31 illustrates a process 3100 for analyzing emergency care that is executed by the configuration 2900 of the distributed system 100 in some examples. As shown in FIG. 31, the analysis process 3100 includes a sequence of actions that are collectively executed by a medical device (e.g., the medical device 104), an event log API (e.g., the event log API 128), an event log application (e.g., the event log application 120), and a log analysis application (e.g., the log analysis application 130).

The analysis process 3100 starts execution if the documentation process 300 described above with reference to FIG. 3. Next, the log analysis application, in response to receiving input from a healthcare provider (e.g., the healthcare provider 116) requesting a rendering of one or more of the reports 2902, connects to the event log API, and transmits a request for the one or more reports 2902. In response, the event log API analyzes 3102 previously uploaded logs, generates, and/or transmits the requested reports to the log analysis application. In some examples, the event log API generates the reports on-demand or periodically generates commonly requested reports as described above. In response to receiving the requested reports 2902, the log analysis application renders 3104 them for presentation to the healthcare provider within, and the analysis process 3100 concludes.

Processes in accordance with the documentation process 300 enable an analyst, such as the healthcare provider 116, to efficiently review multiple patient interventions in search of trends that can be addressed to improve emergency care.

Figure 32:
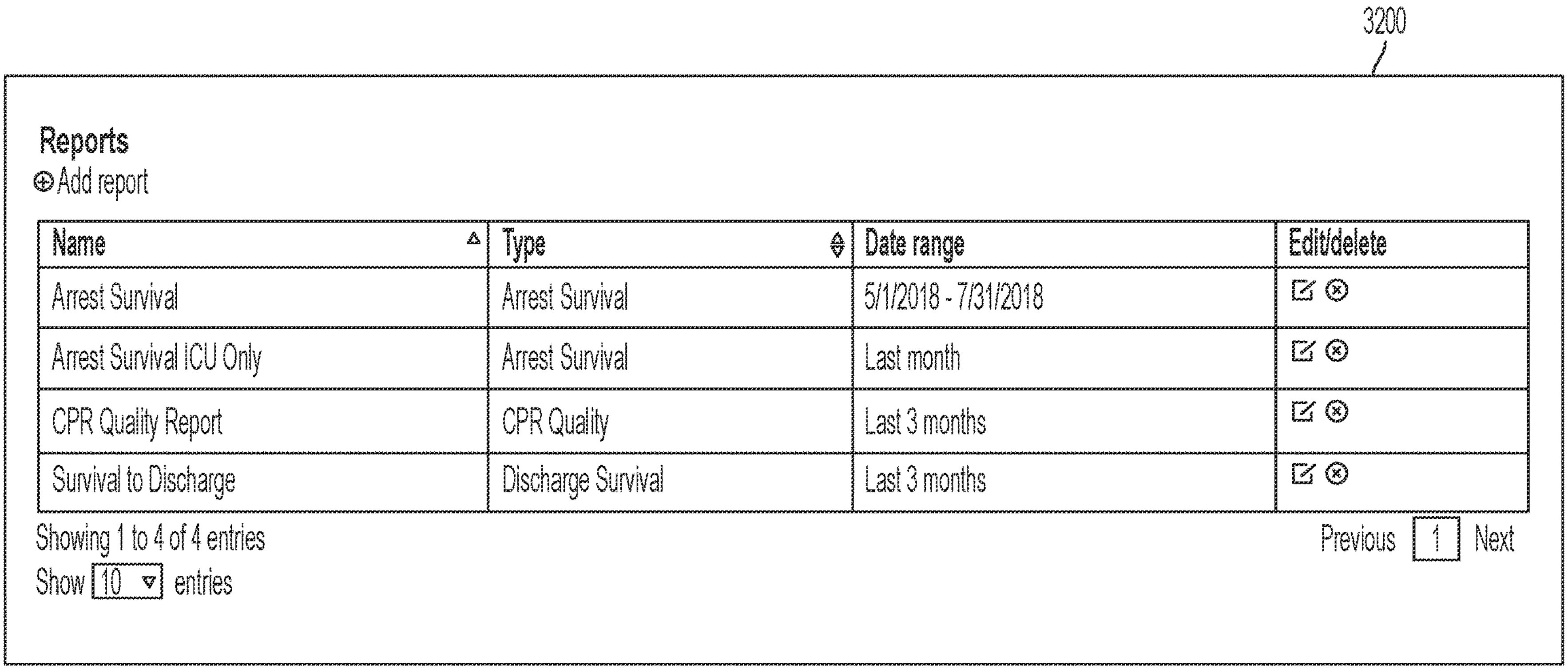
FIG. 32 is a view of a report selection screen provided by a log analysis application in accordance with at least one example disclosed herein.

FIGS. 32-37 illustrate examples of several reports 2902 and associated screens that may be rendered 3104 by the log analysis application. For instance, FIG. 32 illustrates a report selection screen 3200. As shown in FIG. 32, the report selection screen 3200 includes a set of report controls for commonly requested reports. Each report control of the set is associated and labeled with a particular report. In response to receiving input selecting a report control of the set of reason controls, the log analysis application transmits a request to the event log API identifying the report associated with the control and its preset filters. As depicted in FIG. 32, the report selection screen includes report controls associated with an arrest survival report, an arrest survival ICU only report, a CPR quality report, and a survival to discharge report. The report control associated with the arrest survival report further includes a date range filter specifying a date range between May 1, 2018 and Jul. 31, 2018. The report control associated with the arrest survival ICU only report further includes a date range filter specifying a date range that is relative to the current date/time—last month. The report control associated with the CPR quality report further includes a date range filter restricting the data analyzed for the report to the last 3 months. The report control associated with the survival to discharge report also includes a date range filter restricting the data analyzed for the report to the last 3 months.

Figure 33:
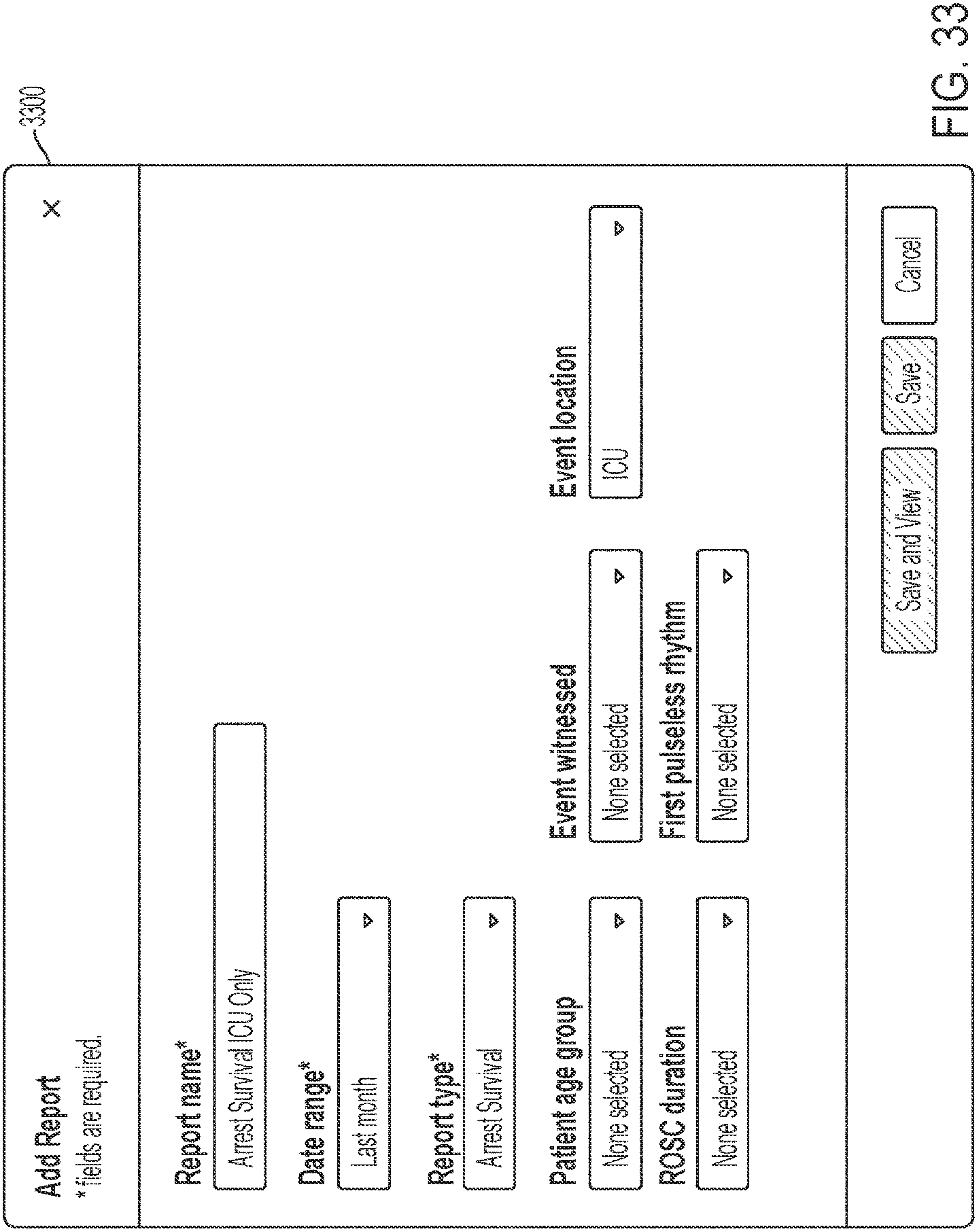
FIG. 33 is a view of an add report screen provided by a log analysis application in accordance with at least one example disclosed herein.

As shown in FIG. 32, the example of the report selection screen 3200 includes controls to edit and/or delete existing report controls. Additionally, as shown, the report selection screen 3200 includes an add report control that is configured to add additional report controls to the list of commonly requested reports. The log analysis application is configured to respond to selection of the add report control by providing an add report screen, such as the add report screen 3300 illustrated in FIG. 33. As shown in FIG. 33, the add report screen 3300 may include controls to specify a new report name, date range filter, report type, patient age group filter, ROSC duration filter, event witnessed filter, first pulseless rhythm filter, and event location filter. Additionally, the report selection screen 3200 includes controls to save, view, and cancel a new report.

FIG. 34 illustrates an example of an arrest survival report. As shown in FIG. 34, the illustrated arrest survival report 3400 includes metrics and bar graphs that indicate, by month, a number of arrests that were survived, a total number of arrests, a percentage of the total number that were survived, and a total number of arrests with incomplete data (e.g., with no survival data entered). The arrest survival report 3400 shown also lists an average survival rate for the entire span of time depicted. The arrest survival report 3400 further displays the date range and other filters applied to the data used to generate the report and includes a link to export the report in PDF format.

Figure 35:
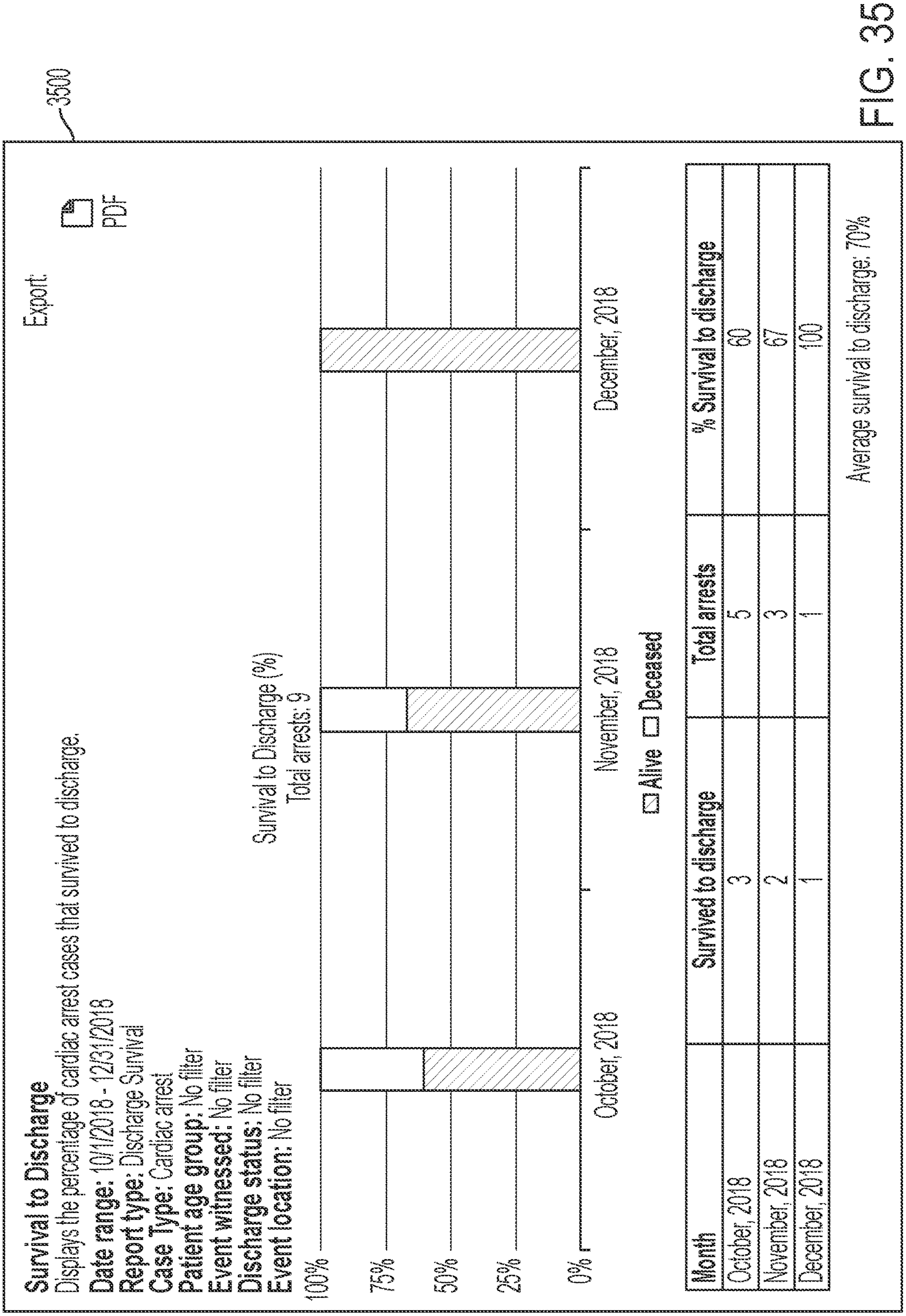
FIG. 35 is a view of a survival to discharge report screen provided by a log analysis application in accordance with at least one example disclosed herein.

FIG. 35 illustrates an example of a survival to discharge report. As shown in FIG. 35, the survival to discharge report 3500 includes metrics and bar graphs that indicate, by month, a number of arrests that were survived until discharge, a total number of arrests, and a percentage of the total number that were survived until discharge. The survival to discharge report 3500 also lists an average survival rate until discharge for the entire span of time depicted. The survival to discharge report 3500 further displays the date range and other filters applied to the data used to generate the report and includes a link to export the report in PDF format.

Figure 36A:
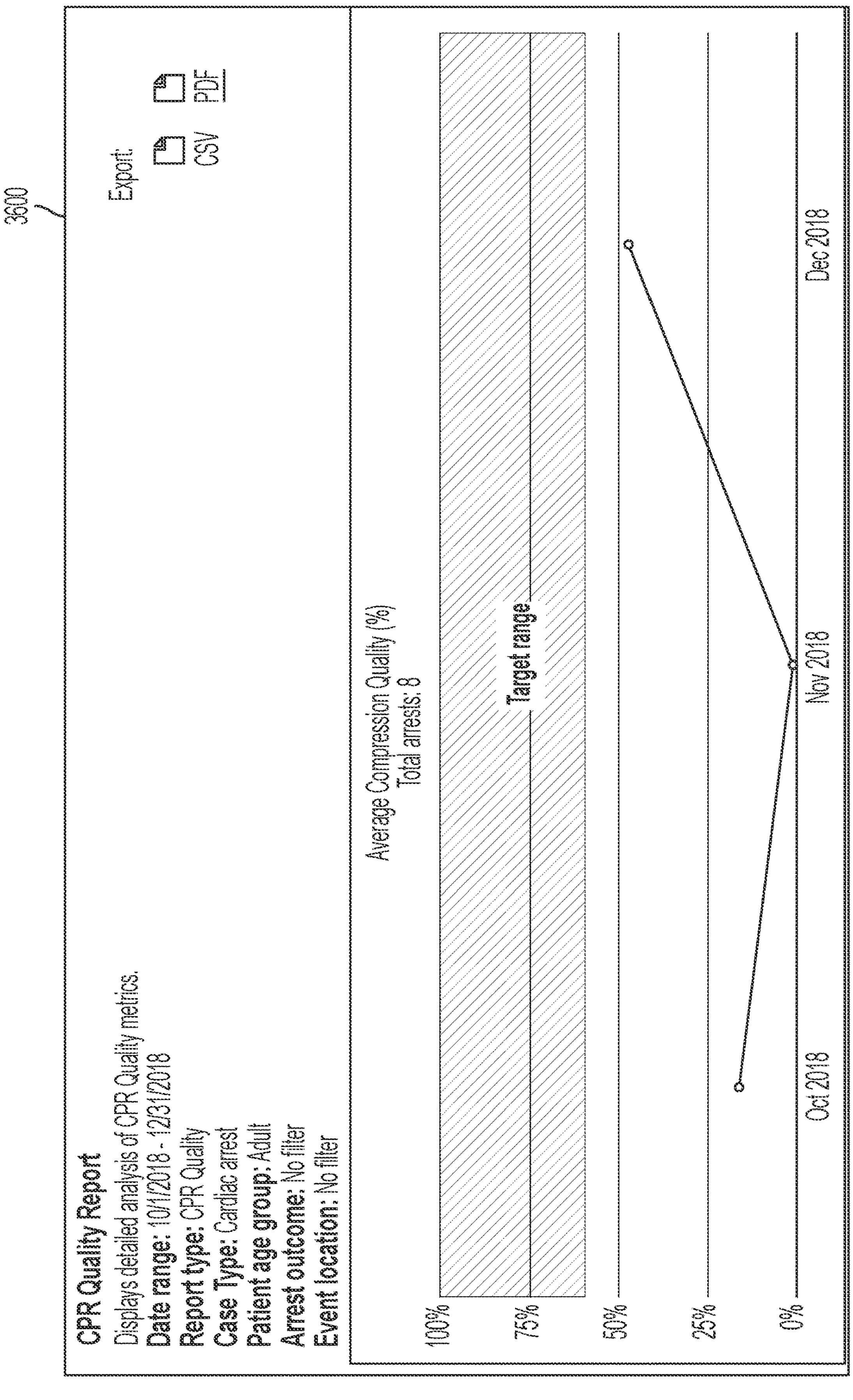
FIG. 36A is a view of a CPR quality report screen showing average compression quality provided by a log analysis application in accordance with at least one example disclosed herein.
Figure 36B:
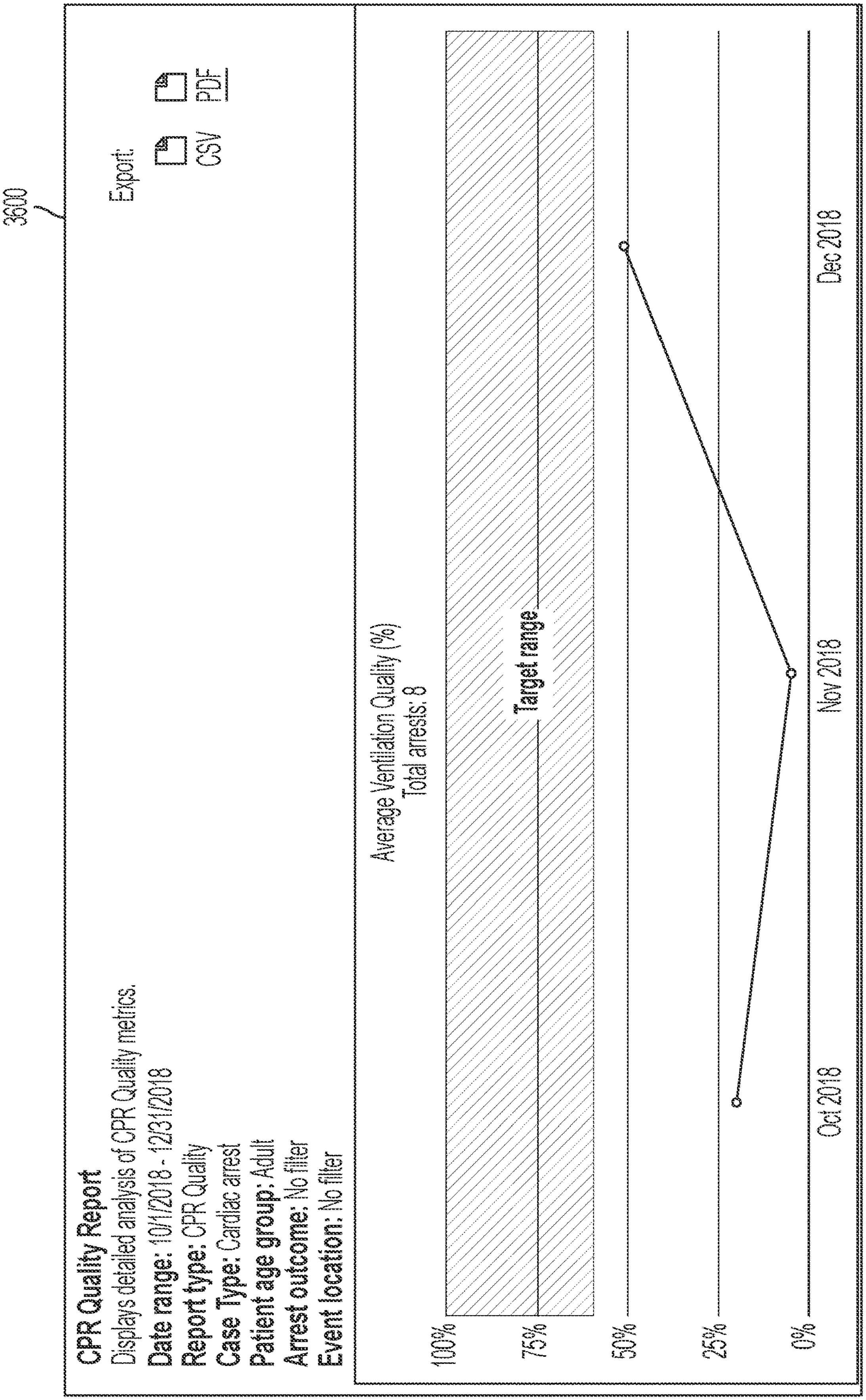
FIG. 36B is a view of a CPR quality report screen showing average ventilation quality provided by a log analysis application in accordance with at least one example disclosed herein.

FIGS. 36A and 36B illustrate examples of a first portion of a CPR quality report 3600. As shown in FIG. 36A, the first portion of the CPR quality report 3600 includes metrics and line graphs that indicate, by month, an average compression quality percentage. As shown in FIG. 36B, the first portion of the CPR quality report 3600 includes metrics and line graphs that indicate, by month, an average ventilation quality percentage. The first portion of the CPR quality report 3600 also lists target ranges for these averages. The first portion of the CPR quality report 3600 further displays the date range and other filters applied to the data used to generate the report and includes links to export the report in CSV or PDF format. In some embodiments, there may be an option to include cases in the overall summary report that have been reviewed. For instance, there may be inaccurate information in some of the cases, such as an inaccurate chest compression fraction or other data. Accordingly, it may be undesirable to include faulty information in overall summary reports.

Figure 37:
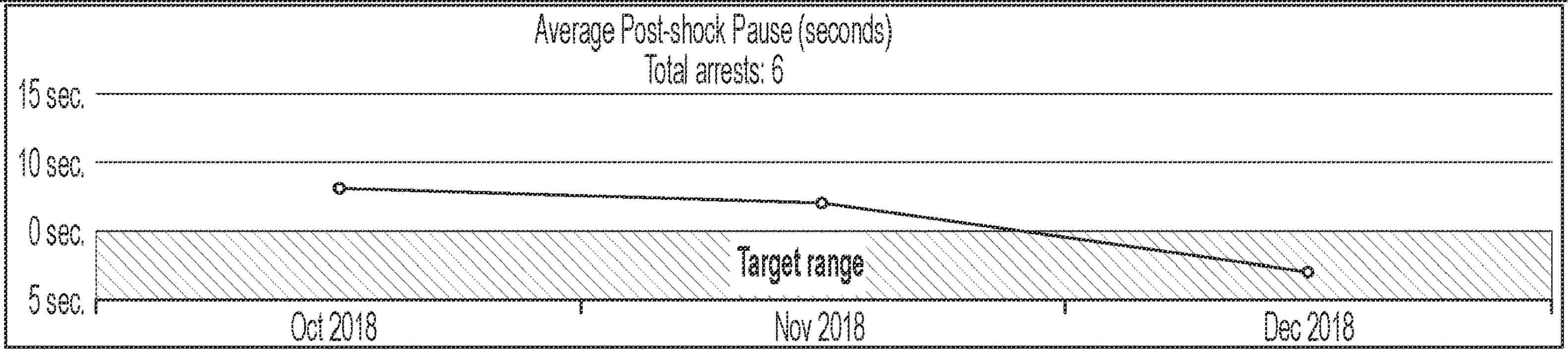
FIG. 37 is a front view of an average post-shock pause report screen provided by a log analysis application in accordance with at least one example disclosed herein.

FIG. 37 illustrates an example of a second portion of the CPR quality report 3700. As shown in FIG. 37, the second portion of the CPR quality report 3700 includes metrics and line graphs that indicate, by month, an average post-shock pause (i.e., time elapsed between administration of a defibrillation shock and the recommencement of chest compressions). The reason for this report is so that medical organizations are able to better evaluate and train their personnel to minimize the post-shock pause period (e.g., keep the post-shock pause to less than 5 seconds). Similar, it is desirable for medical organizations to evaluate and train their personnel to minimize the pre-shock pause period (e.g., keep the pre-shock pause to less than 5 seconds). The second portion of the CPR quality report 3700 also lists a target range for this average. The second portion of the CPR quality report 3700 further displays additional monthly CPR metrics controls that, when selected, cause the log analysis application to display a line graph depicting the monthly CPR metric and a target range for the same, analogously to the average compression quality metric and the average post-shock pause metric described above. These metrics include total arrests (number with shocks), average compression depth, average compression rate, average chest compression release velocity, average percentage of compression with depths in target, average percentage of compression rates in target, average chest compression faction, average pre-shock pause (i.e., time elapsed between the pausing of chest compressions and the administration of a defibrillation shock), average ventilation tidal volume, average ventilation rate, average percentage of ventilations with tidal volume in target, average percentage of ventilation rates in target.

Serverless Client Log Consolidation

Figure 38:
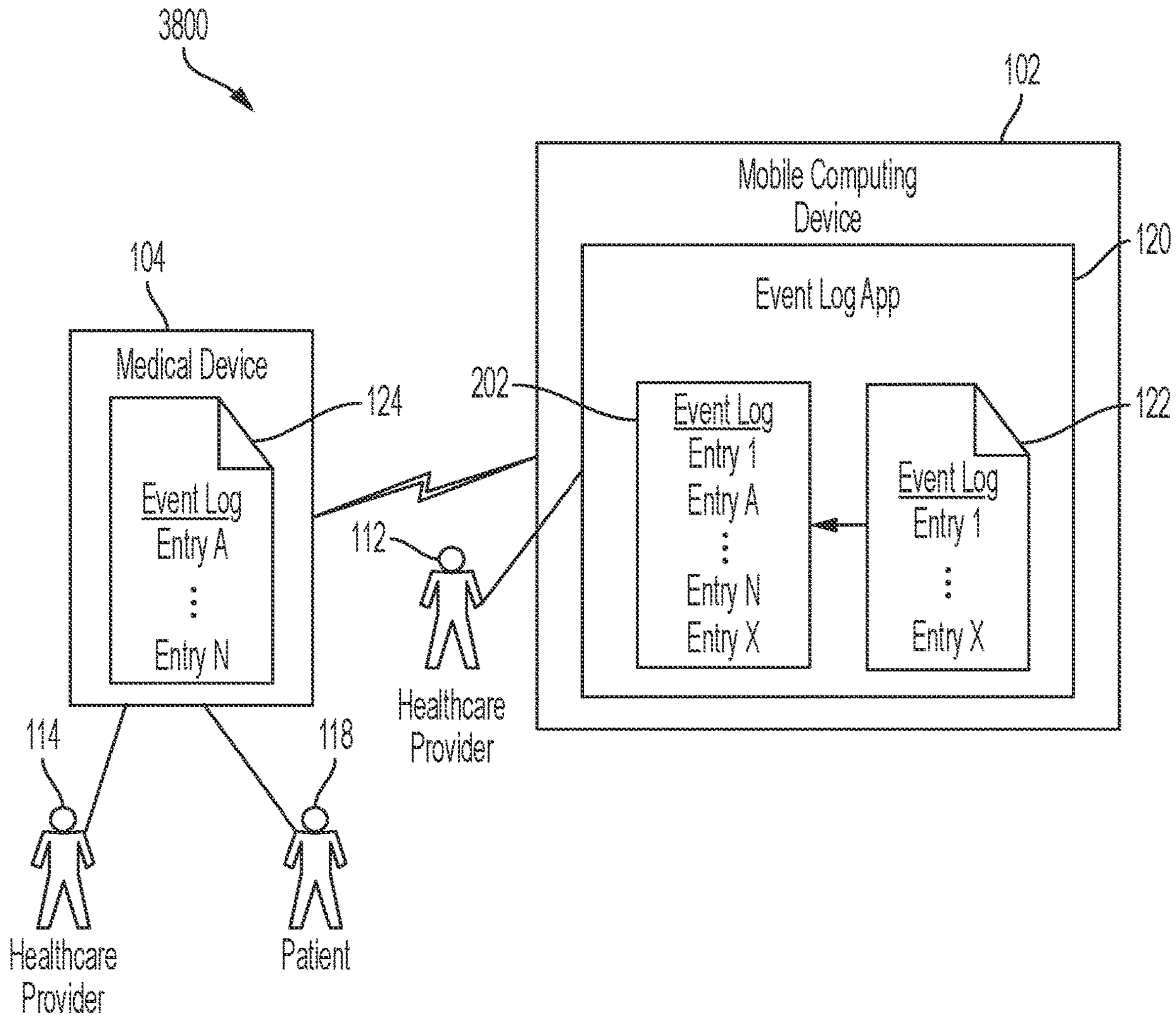
FIG. 38 is a block diagram illustrating another configuration of the distributed system of FIG. 1 in accordance with at least one example disclosed herein.

FIG. 38 illustrates a particular configuration 3800 of the distributed system 100 in which the event log application 120 is configured to interoperate with the medical device 104 directly via a proximal connection to provide the healthcare provider 112 with the view 202. As shown in FIG. 38, the configuration 3800 includes the mobile computing device 102 and the medical device 104. In operation, the configuration 3800 can be used by the healthcare provider 112 to document care provided to the patient 118 by the healthcare provider 114 and/or the medical device 104 without needing additional technological infrastructure, such as a separate computing device and/or server as that illustrated in FIGS. 1, 2, 29, for instance.

Figure 39:
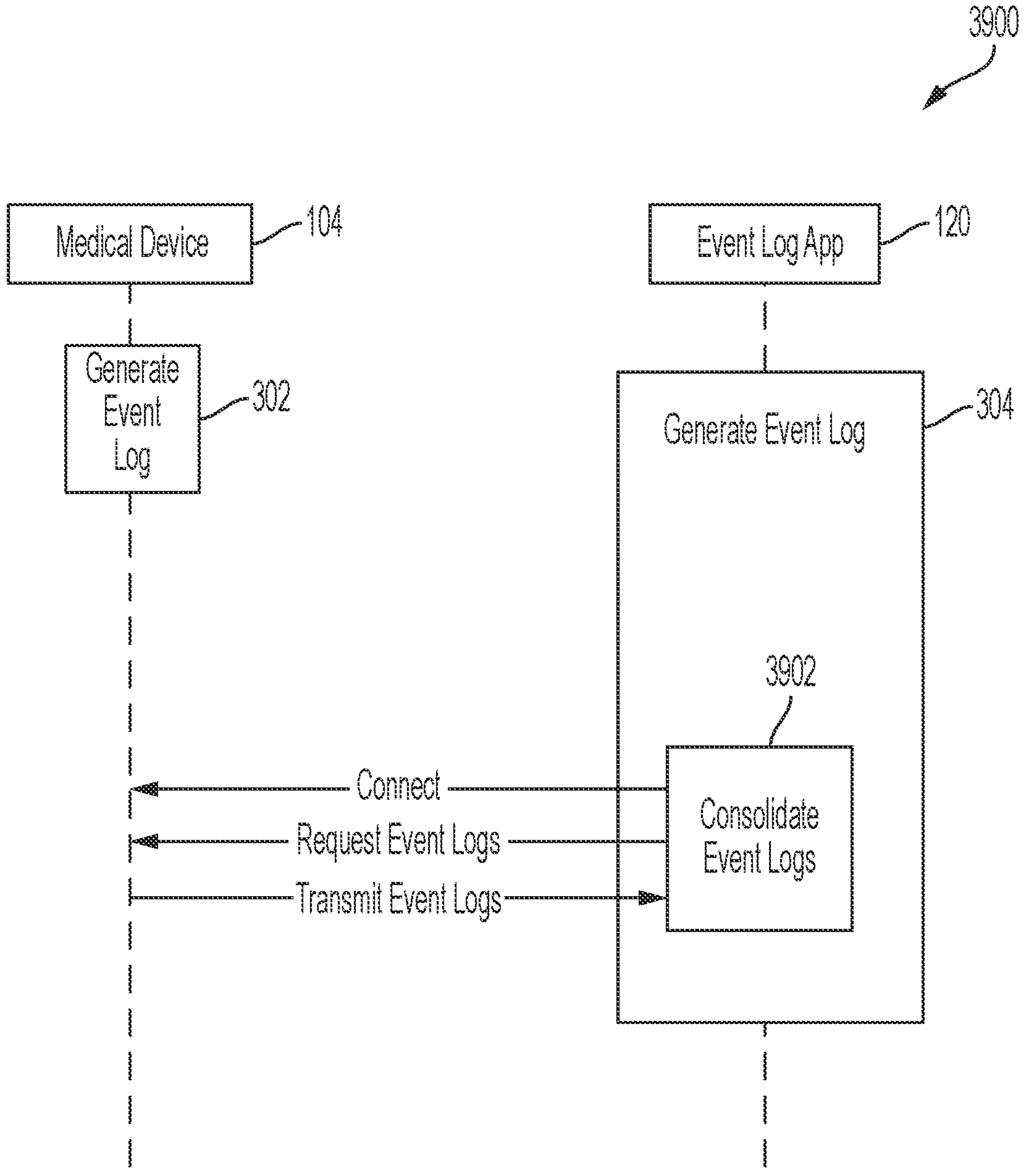
FIG. 39 is a sequence diagram illustrating another process of documenting emergency care in accordance with at least one example disclosed herein.

FIG. 39 illustrates a process 3900 for documenting emergency care that is executed by the configuration 3800 of the distributed system 100 in some examples. As shown in FIG. 39, the documentation process 3900 includes a sequence of actions that are collectively executed by a medical device (e.g., the medical device 104) and an event log application (e.g., the event log application 120).

The documentation process 3900 starts with the medical device generating 302, as described above with reference to FIG. 3, an event log (e.g., the event log 124). This event log includes one or more entries (e.g., the log entries A through N). The documentation process 3900 continues with the event log application generating 304, as described above with reference to FIG. 3, log entries (e.g., the log entries 1 through X of the event log 122) for an open event log. As with the medical device, each log entry generated by the event log application may include a date/time stamp indicating the time at which an event documented by the entry occurred and an indicator of the event, such as a type identifier or a textual description of the event.

As shown in FIG. 39, generating 304 the open event log includes consolidating 3902, by the event log application, the open event log with event logs originated from other source devices, such as the medical device. In some examples, as part of consolidating 3902 the open event log with other event logs, the event log application connects to the medical device and requests one or more event logs stored on the medical device. In response to receiving a request for event logs, the medical device transmits copies of the one or more identified event logs to the event log application.

Next, as part of generating 304 the open event log, the event log application provides a healthcare provider (e.g., the healthcare provider 112) with a view (e.g., the view 202) of the consolidated event log. Generating 304 continues with the event log application interacting with the healthcare provider to generate entries for the open event log until the user closes the open event log. In some examples, which are described above with reference to FIG. 25, the event log application prevents modification, via the view, of entries generated by sources other than the event log application.

In some examples, the mobile computing device establishes the connection to the medical device described above using an ad-hoc, proximal network connection. In these examples, a first device (e.g., the mobile computing device) can request to establish or join a wireless communication channel with a second device (e.g., the medical device) via a proximity-based interaction, which may involve sensing of one or more features of the immediate environment, resulting in the determination of an appropriate spatial localization between devices. The request for connection may include or may be based on an identifier of the second device. The identifier may include a predetermined key or code that indicates to the first device the origin of the second device. Or, the identifier may include data related to the sensed feature(s) that are used for mutual or one-way authentication and/or establishing the secure channel. A proximity-based interaction may include close proximity wireless communication interaction between two closely positioned devices, such as two devices in contact with each other or positioned within a threshold distance (e.g., less than 100 cm, less than 50 cm, less than 20 cm, less than 15 cm, less than 10 cm, less than 5 cm, less than 2 cm, less than 3 cm, less than 4 cm) of each other. Examples of proximity-based interactions, which may result from sensing certain features of the immediate environment (discussed in more detail below), can include, e.g., tapping of the first device against a tap zone on the second device, an acoustic interaction between the first device and the second device, image recognition of the first device or a portion of the first device by the second device, recognition by the second device of a gesture made by the first device, transmission of an electromagnetic (e.g., electronic, radio frequency, etc.) signal from the first device to the second device via a short-range communication protocol (e.g., NFC, RFID, Bluetooth Low Energy, ZigBee, or another short-range communication protocol), or another type of proximity-based interaction. As will be appreciated, other similar examples of proximity-based interactions and approaches to spatial localization are possible.

The proximity-based interaction is a simple, efficient interaction that does not take significant time or attention on the part of a healthcare provider, thus enabling the healthcare provider to maintain focus on treating the patient. As an example, a healthcare provider may establish a secure connection via an accepted spatial localization between the mobile computing device and the medical device where the medical device is already in use on the patient and obtain a download of log entries relevant to treatment of the patient (e.g., ECG history, shock history, chest compression history, ventilation history, etc.). The healthcare provider may then establish a secure connection via an accepted spatial localization between the mobile computing device and a subsequent medical device (e.g., an advanced life support defibrillator, such as an X Series® defibrillator/monitor available from ZOLL® Medical Corporation) that arrives on the scene at a later time, allowing the event log application to document care provided by both the medical device and the subsequent medical device. If the patient is transported to another location, the healthcare provider may further establish yet another secure connection via an accepted spatial localization between the mobile computing device and another medical device (e.g., an advanced life support hospital defibrillator, such as an R Series defibrillator/monitor available from ZOLL® Medical Corporation), collecting additional log entries from the other medical device and further documenting the care provided to the patient. As a result, all relevant treatment information is securely transferred to and logged by the event log application for monitoring and treating the patient in an efficient and convenient manner.

In some examples, a wireless communication channel can be established between the first device and the second device, or the first device can be enabled to join an existing wireless communication channel to which the second device already belongs.

In some examples, the first device can be authenticated by the second device. Authentication can be performed via a proximity-based interaction, according to one or more sensed features. Authentication of the first device helps to ensure that the device that made the request is the device that is enabled to join the wireless communication channel. Authentication can thus help to prevent unauthorized or unintentional access to a wireless communication channel for a particular patient by other devices not involved in the treatment of that patient. In some examples, prior to authentication, device addresses, associated user codes, and passwords are pre-configured into memory and/or storage of each device so that upon initiation of the proximity-based interaction between pre-configured devices, the authentication protocol for initiating and establishing the secure connection is triggered.

In some examples, after execution of the authentication protocol, either of the devices can use the information described above to establish a secure communicative connection with the other via another private or public network. In these and other examples, the communicative connection between the devices can be made and/or maintained via an addition computing device distinct from the devices. Alternatively or additionally, in some examples, after execution of the authentication protocol, either of the devices can establish a direct communicative connection with the other in which no intermediate devices participate.

In some examples, both the request by the first device and the authentication of the first device can be performed through a single proximity-based interaction, or by simply bringing the devices within a suitable distance relative to one another. In some examples, the request by the first device and the authentication of the first device are performed by separate proximity-based interactions.

Once the wireless communication channel has been established, log entries can be exchanged between the first and second devices. These log entries can document treatment provided to the patient and can, for example, include data indicative of a shock delivered to the patient by the first medical device, a rate of compressions delivered to the patient, a depth of compressions delivered to the patient, rate of ventilations delivered to the patient, tidal volume of ventilations delivered to the patient, medication administered to the patient, and a duration of compressions delivered to the patient. The log entries and further document health data/parameter(s) indicative of a health status of the patient, such as data indicative of an electrocardiogram (ECG) signal of the patient, a blood pressure of the patient, a temperature of the patient, a respiration rate of the patient, a blood oxygen level of the patient, a pulmonary function of the patient, a blood glucose level of the patient, and/or other appropriate patient-related information.

Figure 40:
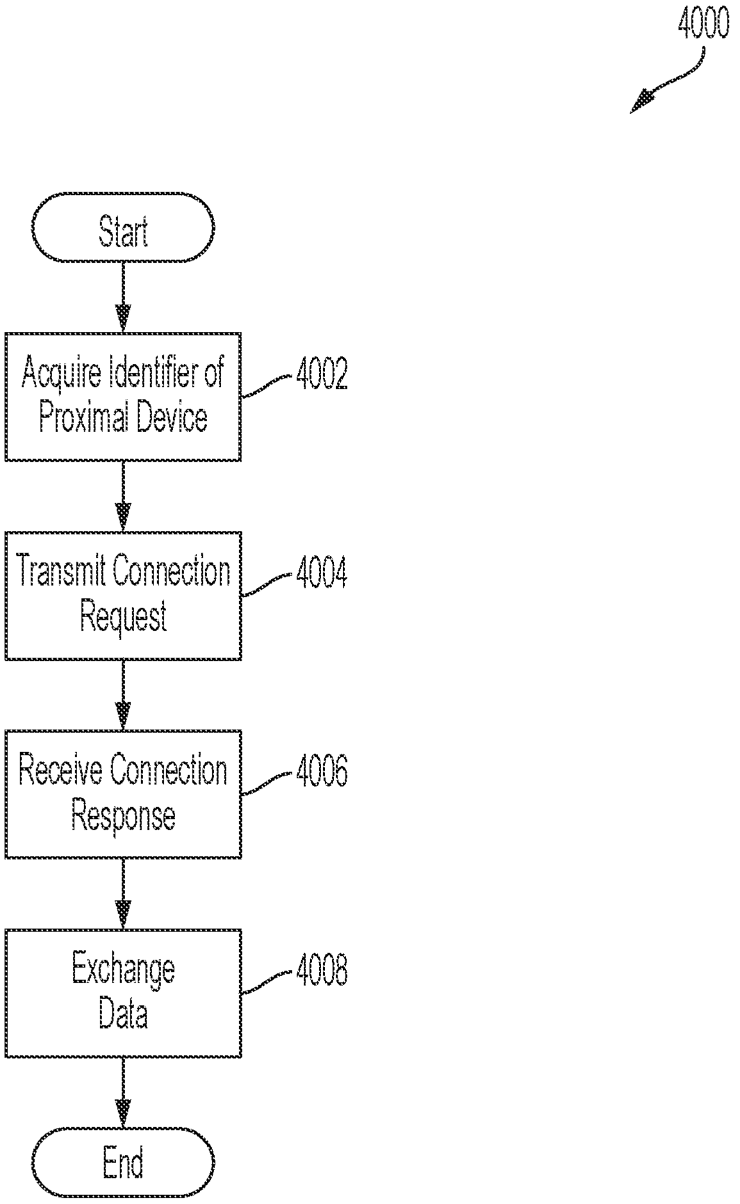
FIG. 40 is a flow diagram illustrating a process of establishing an ad-hoc network in accordance with at least one example disclosed herein.

FIG. 40 illustrates a communication process 4000 for establishing an ad-hoc network that is executed by the mobile computing device in some examples. As shown in FIG. 40, the communication process 4000 starts with the mobile computing device acquiring 4002 an identifier of a proximal device (e.g., the medical device). In various examples, the mobile computing device can acquire 4002 the identifier through a variety of signals. Examples of these signals include audio signals, visual signals, and radio-frequency signals to name a few. For instance, in one example, the mobile computing devices acquires an identifier of the proximal device by scanning, with an integrated camera, a fiducial (e.g., a QR code or barcode) visible on the proximal device. In another example, the mobile computing device acquires an identifier of the proximal device by receiving and decoding sounds generated by the proximal device. Alternatively or additionally, in some examples, the mobile computing device acquires an identifier of the proximal device by receiving data stored within an NFC/RFID tag/chip located on or within the proximal device.

Next, the mobile computing device transmits 4004 a connection request to the medical device to establish an ad-hoc network connection. The mobile computing device receives 4006 a response from the medical device, thereby establishing a communication channel with the medical device. After establishing the communication channel, the mobile computing device exchanges 4008 data with the medial device. This data includes event logs and/or event log entries generated by the medical device.

Processes in accord with the communication process 4000 enable a mobile computing device and event log application to quickly and easily receive event logs accurately documenting patient treatment from multiple sources. As such, these processes enable the event log application to compile a more complete record of patient treatment than can be documented by an event log application that is a single source of documentation. In the examples described above the mobile computing device establishes a network connection with the medical device. Alternatively or additionally, in some examples, the medical device establishes the network connection with the mobile computing device via an approach in which the mobile computing device and the medical device exchange roles.

Figure 52:
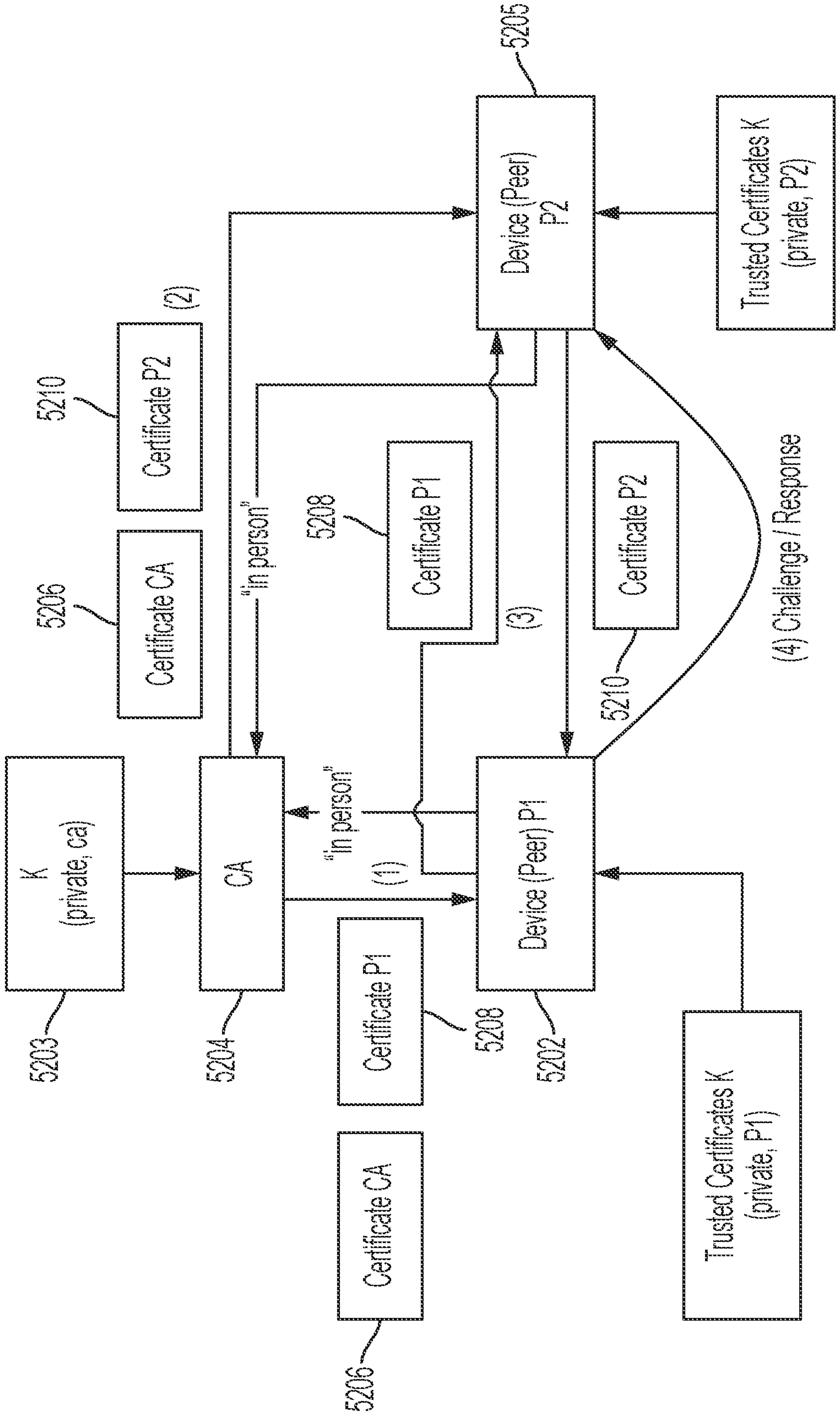
FIG. 52 is a diagram of public-key infrastructure (PKI) authentication architecture in accordance with at least one example disclosed herein.

In some examples, a secure ad-hoc network is established between the mobile computing device and the medical device. A public-key infrastructure (PKI) may be used for establishing a secure channel. In a public key infrastructure (PKI), certificates are used for the purpose of authentication. A certificate is a virtual document that allows an authenticator to verify the identity of a user without having any prior knowledge about the user, according to one example. Several forms of public-key infrastructures exist. FIG. 52 is one example of a PKI authentication architecture. In the figure, the numbers indicate the order of events. In FIG. 52, a PKI architecture is shown in simple form, in which one extra entity is involved called the certificate authority (CA) 5204. The setup process for all peers is to get a certificate at the CA. The CA is responsible for checking the identity one time 'in person'. In the case of a Near Field Communication (NFC) mobile phone for example, the setup process could be done during the manufacturing of the phone/secure element as the "in person" check in. After the CA 5204 has verified the identity of a requester, called peer 1 (P1) 5202, it creates and signs a certificate $C_{p1}$ 5208. A well-known standard for certificates is X.509 defined in RFC 2459. The information 1 on the certificate 5208 includes the identity information of the peer (which may be referred to as Ip1) and the CA that signed it (which may be referred to as Ica), a public key (Kpub, p1) and a signature (Sp1).

The signature is calculated by hashing and encrypting $K_{pub,\,p1}$ and $I_{p1}$ using the CA's private key ($K_{priv,\,ca}$) 5203. After signing, the CA 5204 gives the requester its certificate $C_{p1}$ 5208. Furthermore, the CA 5204 provides its own certificate ($C_{ca}$) 5206 to the requester containing the public key ($K_{pub,\,ca}$). $C_{CA}$ 5206 is a special type of certificate indicating that it can be used to sign other certificates but $C_{CA}$ is not signed itself, according to one example. After this, the setup process is finished, according to one example.

All peers keep a list of CA certificates that are trusted which, in this example, implies that every peer with a certificate signed by one of the CAs in its list is trusted. Therefore, this list may be chosen carefully and protected from unintended change, in such examples. When two peers, p1 5202 and p2 5205, want to authenticate each other, they first exchange certificates. They each verify that the certificate was signed by a CA that they trust. This is done by decrypting the signature on the peer's certificate with the public key of the CA (which is on the certificate of the CA). Subsequently, the peers each verify that the other owns the private key corresponding to the public key on the certificate. This can be done by a challenge/response mechanism. Private keys remain confidential to their owners, in this example, including the private key of the CA 5204. Though in the example discussed here, a PKI with one CA has been described, it is possible to have a hierarchical infrastructure of certificate authorities, in which certificate authorities in tier 2 have a certificate signed by a certificate authority in tier 1, which in turn is signed by the root certificate authority. The root certificate authority may have a self-signed certificate meaning that the signature is calculated from its own private key, in some cases, in which the certificate authorities below the root certificate authority inherit the trustworthiness of the root certificate authority. This architecture is useful in large systems for load balancing. PKI schemes like EAP-TLS, EAP-TTLS, EAP-IKEV2 may be employed, or other schemes known to those skilled in the art, based on the present disclosure.

Additional Examples

Figure 41:
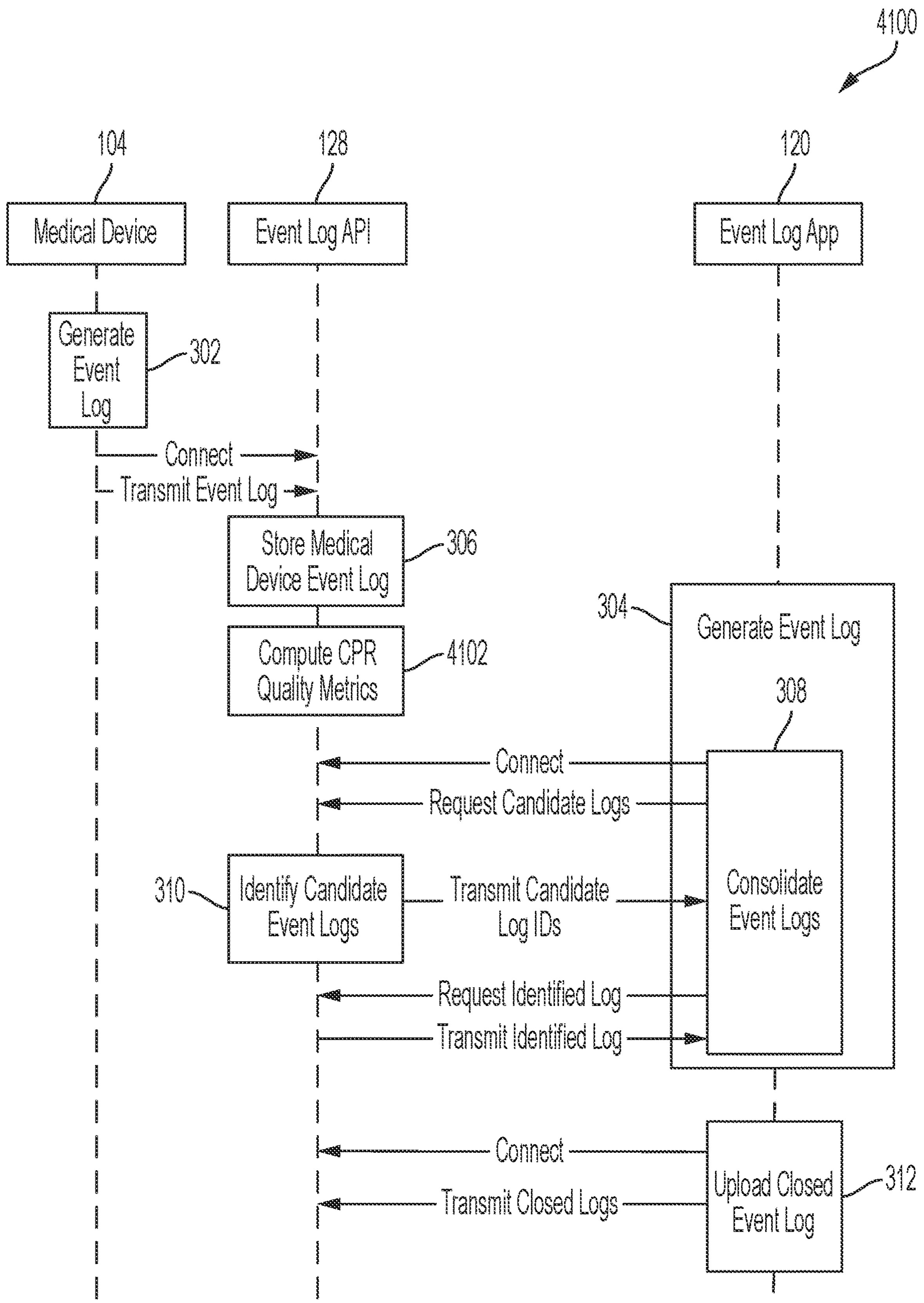
FIG. 41 is a sequence diagram illustrating another process of documenting emergency care in accordance with at least one example disclosed herein.

FIG. 41 illustrates a process 4100 for documenting emergency care that is executed by the configuration 200 of the distributed system 100. As shown in FIG. 41, the documentation process 4100 includes a sequence of actions that are collectively executed by a medical device (e.g., the medical device 104), an event log API (e.g., the event log API 128), and an event log application (e.g., the event log application 120). The documentation process 4100 includes the actions executed by the documentation process 300 described above. In addition, within the documentation process 4100, the event log API expressly computes 4102 CPR quality metrics after storing 306 the medical device event logs. The CPR quality metrics computed 4102 by the event log API (e.g., via the processing components described above with reference to FIG. 1) may include one or more of average compression quality, average post-shock pause, average compression depth, average compression rate, average ventilation tidal volume, average ventilation rate, average chest compression release velocity, average percentage of compression with depths in target, average percentage of compression rates in target, average percentage of ventilations with tidal volume in target, average percentage of ventilation rates in target, average chest compression faction, and average pre-shock pause. In some embodiments, the medical device 104 computes the CPR quality metrics and then transmits the CPR quality metrics to the event log API 128 for storage and, if desired, subsequent transmission to the event log application 120 running on the mobile computing device.

Figure 42:
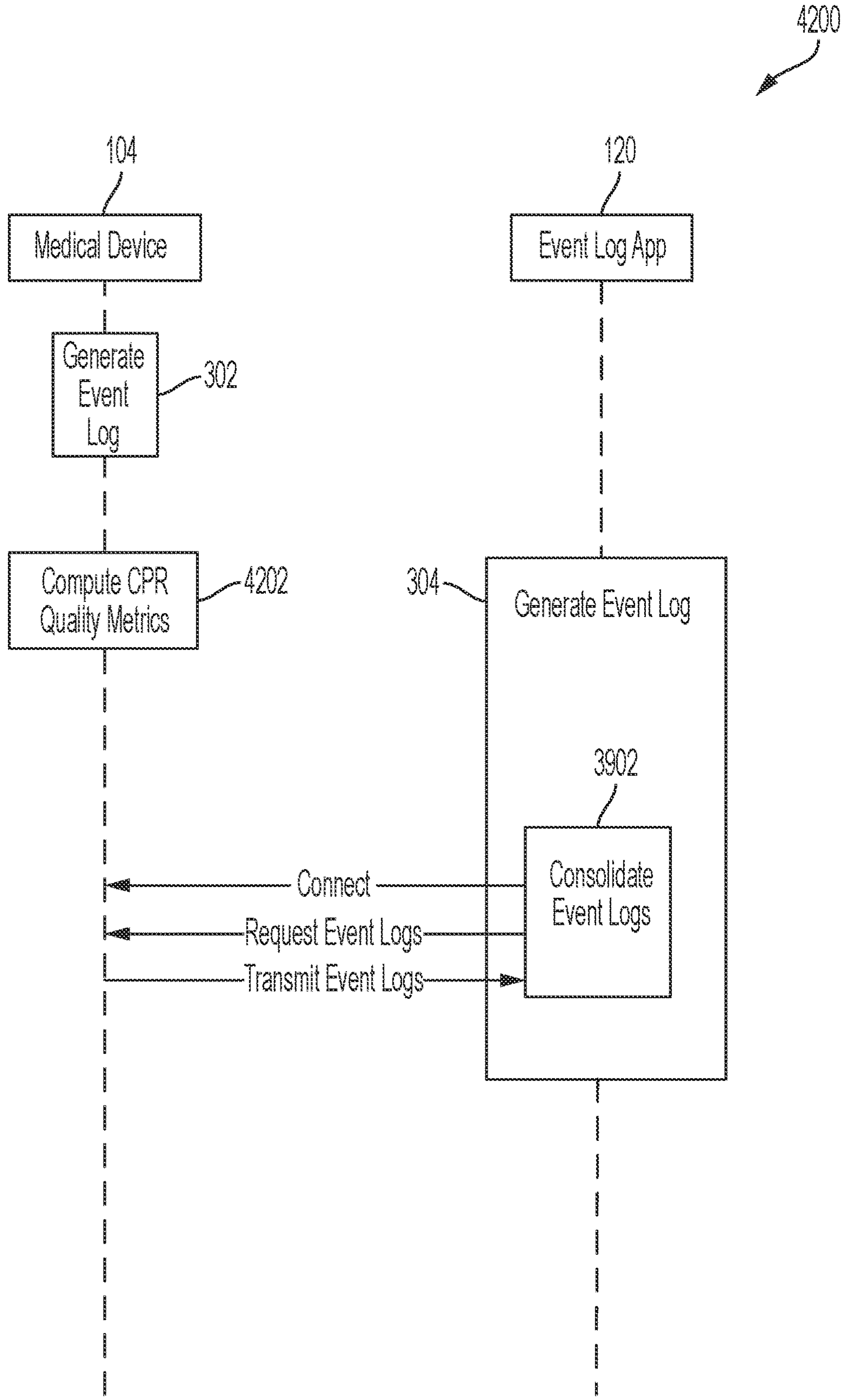
FIG. 42 is a sequence diagram illustrating another process of documenting emergency care in accordance with at least one example disclosed herein.

FIG. 42 illustrates a process 4200 for documenting emergency care that is executed by the configuration 3800 of the distributed system 100. As shown in FIG. 42, the documentation process 4200 includes a sequence of actions that are collectively executed by a medical device (e.g., the medical device 104) and an event log application (e.g., the event log application 120). The documentation process 4200 includes the actions executed by the documentation process 3900 described above. In addition, within the documentation process 4200, the medical device expressly computes 4202 CPR quality metrics after generating 302 the medical device event log. In some embodiments, discussed above, the CPR quality metrics may be computed by the medical device 104 and/or by the event log API 128, for subsequent transmission to the event log application 120 being executed on the mobile computing device. For example, the CPR quality metrics may be computed by the medical device 104 and then transmitted to the event log API 128, which may then be transmitted to the event log application 120 running on the mobile computing device. The CPR quality metrics computed 4202 by the event log API (e.g., via the processing components described above with reference to FIG. 1) may include one or more of average compression quality, average post-shock pause, average compression depth, average compression rate, average ventilation tidal volume, average ventilation rate, average chest compression release velocity, average percentage of compression with depths in target, average percentage of compression rates in target, average percentage of ventilations with tidal volume in target, average percentage of ventilation rates in target, average chest compression faction, and average pre-shock pause. In some examples, the CPR quality metrics computed 4202 are associated with the event log generated 302 by the medical device. In these examples, the CPR quality metrics are transmitted along with their associated event log to the event log application.

Figure 43:
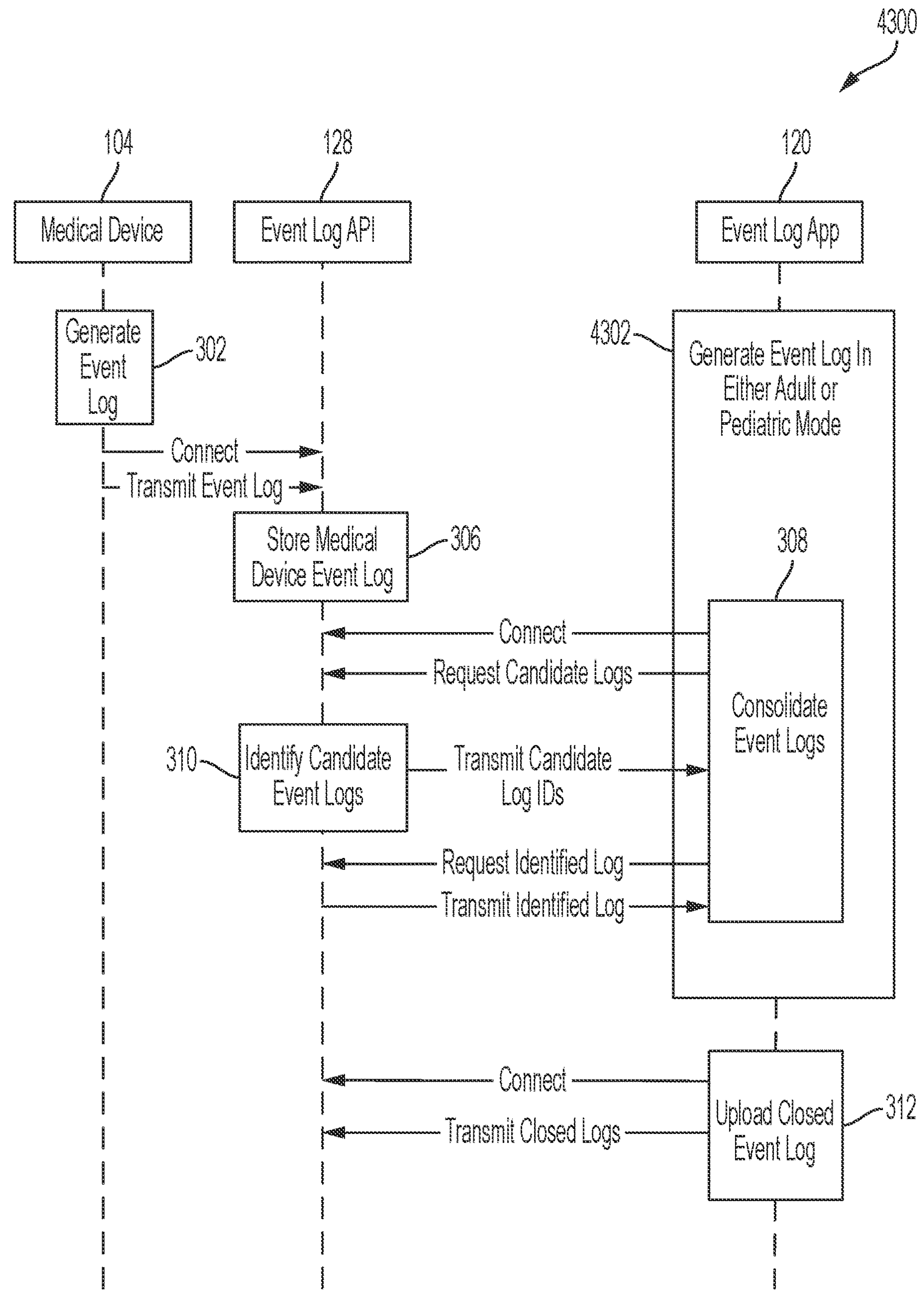
FIG. 43 is a sequence diagram illustrating another process of documenting emergency care in accordance with at least one example disclosed herein.

FIG. 43 illustrates a process 4300 for documenting emergency care that is executed by the configuration 200 of the distributed system 100. As shown in FIG. 43, the documentation process 4300 includes a sequence of actions that are collectively executed by a medical device (e.g., the medical device 104), an event log API (e.g., the event log API 128), and an event log application (e.g., the event log application 120). The documentation process 4300 includes the actions executed by the documentation process 300 described above. In addition, within the documentation process 4300, the event log application expressly operates in either adult mode or pediatric mode while generating 4302 entries for the duration of the event log. As such, the event log application provides screens with control altered to reflect either adult mode or pediatrics while the healthcare provider documents emergency care. As discussed above, when the event log application is in adult mode, the documentation screens and options associated therewith may reflect entries that are more common for adult patients than for pediatric patients. Conversely, when the event log application is in pediatric mode, the documentation screens and options associated therewith may reflect entries that are more common for pediatric patients than for adult patients. However, it should be appreciated that even though the event log application may exhibit distinct adult and pediatric modes, there may be a substantial overlap in the types of log entries generated for adult patients and pediatric patients. For example, a documented log entry to when chest compressions or ventilations are started may be the same for adult or pediatric patients. However, the technique of chest compressions is "encircling hands" would be more commonly associated for pediatric patients, more particularly neonatal patients (because it is not natural for encircling hands compressions to be applied to adults) than for adult patients, and so such a technique of chest compressions would be more easily selectable/chosen when the event log application is in pediatric mode.

Figure 44:
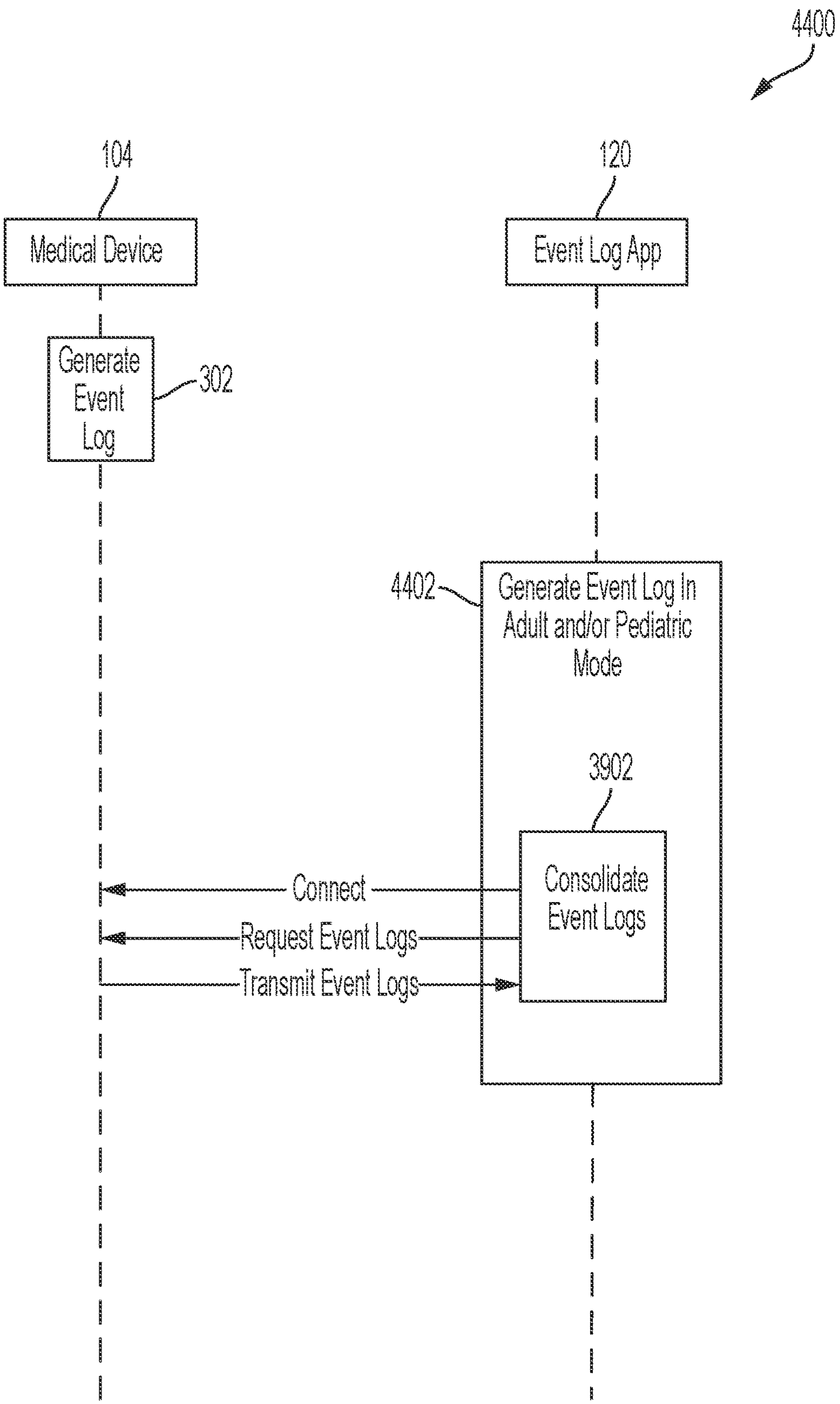
FIG. 44 is a sequence diagram illustrating another process of documenting emergency care in accordance with at least one example disclosed herein.

FIG. 44 illustrates a process 4400 for documenting emergency care that is executed by the configuration 3800 of the distributed system 100. As shown in FIG. 44, the documentation process 4400 includes a sequence of actions that are collectively executed by a medical device (e.g., the medical device 104) and an event log application (e.g., the event log application 120). The documentation process 4400 includes the actions executed by the documentation process 3900 described above. In addition, within the documentation process 4400, the event log application expressly operates in either adult mode or pediatric mode while generating 4402 entries for the duration of the event log. As such, the event log application provides screens with control altered to reflect either adult mode or pediatrics while the healthcare provider documents emergency care.

Figure 45:
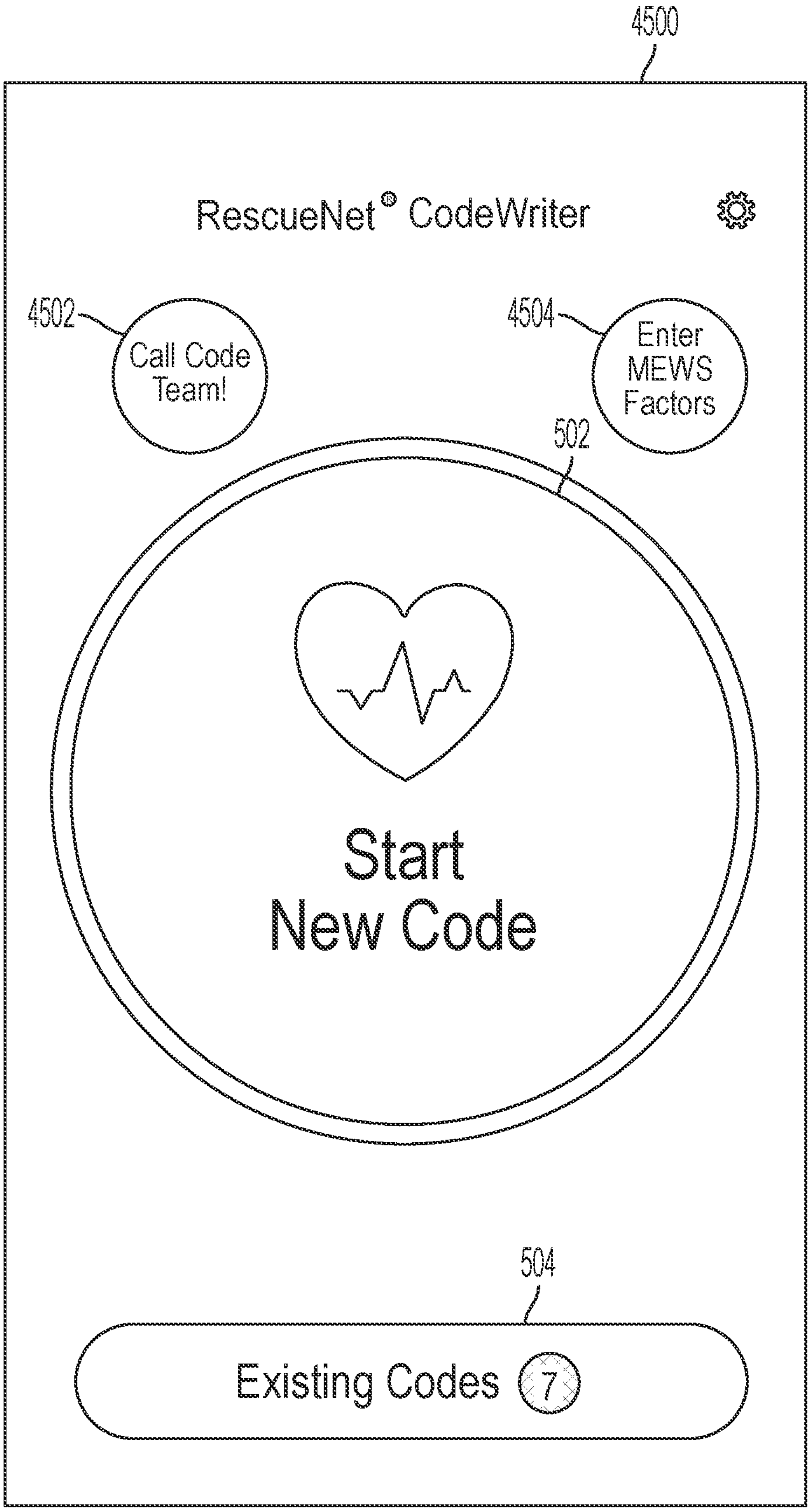
FIG. 45 is a view of another initial screen provided by an event log application in accordance with at least one example disclosed herein.

FIG. 45 illustrates one example of an initial screen 4500 that may be displayed as a result of providing 402 the initial screen in some examples. As shown in FIG. 45, the initial screen 4500 includes the controls of the initial screen 500 and further includes a code team control 4502 for calling a code team and a MEWS control 4504. In some examples, initial screen 4500 may be the initial screen of an early warning system used to estimate the risk of a patient undergoing acute physiologic deterioration and detect medical premonitory events. One way to implement such a system is by providing a MEWS score as discussed in more detail with regards to FIG. 46.

In response to receiving input selecting the code team control 4502, the event log application transmits a notification, via one or more channels, to a code team to indicate the need for emergency care. The one or more channels can include e-mail, text messaging, instant messaging apps, hospital notification systems, intercoms, and the like. The notification can include patient information and/or a location of the mobile computing device (as derived from various technologies, such as global positioning system, local area network connections, cellular network connections, etc.).

Figure 46:
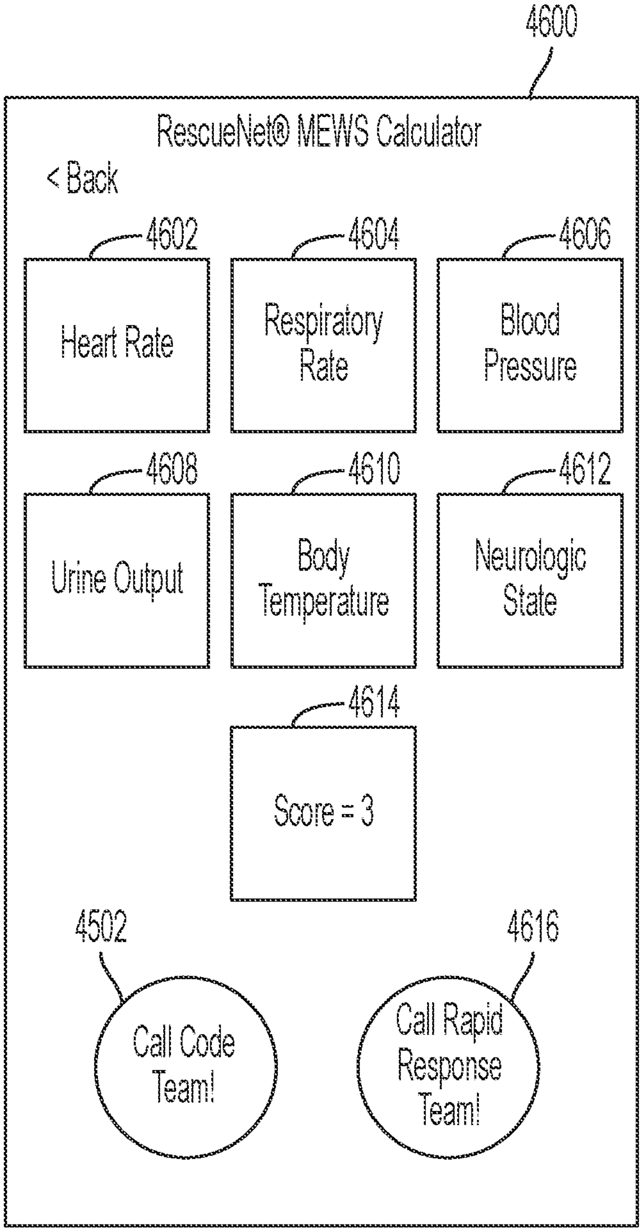
FIG. 46 is a view of a modified early warning score (MEWS) screen provided by an event log application in accordance with at least one example disclosed herein.

In response to receiving input selecting the MEWS control 4504, the event log application provides a MEWS screen, such as the MEWS screen 4600 illustrated in FIG. 46. As shown in FIG. 46, the MEWS screen 4600 includes a several controls to enable collection of MEWS factors. These controls include a heart rate control 4602, a respiratory rate control 4604, a blood pressure control 4606, a urine output control 4608, a body temperature control 4610, a neurologic state control 4612, and score control 4614. As shown in FIG. 46, the MEWS screen 4600 also includes a rapid response control 4616 for calling a rapid response team, and may optionally include a code team control 4502 for calling a code team.

Each of the controls 4602-4612 enable the healthcare provider to enter information used to calculate a MEWS for the patient, which is displayed in the score control 4614.

More specifically, each of the controls 4602-4612, when selected, provides a follow-up screen with controls configured to receive an indication of a measurement or observation of the factor listed in the label of the control. For instance, in response to receiving input selecting the heart rate control 4602, the event log application provides a follow-up screen with a control to receive a numeric value for the patient's observed pulse (e.g., 70 beats per minute). In response to receiving input selecting the neurologic state control 4612, the event log application provides a follow-up screen with a control to receive a selection of one of a set of neurologic state labels (e.g., alert, responds to sound, responds to pain, unresponsive, etc.).

In some examples, the event log application maps each indication received by each of the controls 4602-4612 to a MEWS for that factor and calculates an overall MEWS for the patient by summing the MEWSs of the factors. TABLE 1 is a cross-reference that maps measurements of each of the factors associated with the controls 4062-4612 to a MEWS for that factor.

TABLE 1

| Parameter | 3 | 2 | 1 | 0 | 1 | 2 | 3 |
|---|---|---|---|---|---|---|---|
| Heart Rate | | <40 | 41-55 | 56-105 | 106-115 | 116-130 | >130 |
| Resp. Rate | | <8 | | 9-15 | 16-21 | 22-30 | >30 |
| Blood Pressure | <70 | 71-81 | 82-100 | 101-200 | | >200 | |
| Urine Output | 0 | <0.8 | | | | | |
| Temp | | <35 | 35.1-37 | 37.1-38 | 38.1-38.7 | >38.7 | |
| Alertness | | | | Alert | Responds to sound | Responds to pain | Unresponsive |

In TABLE 1, the heart rate values are in beats per minute. The respiratory values are in breaths per minute. The blood pressure values are in millimeter of mercury. The urine output is in milliliters per hour. The body temperature is in degrees Celsius. According to one example, where a patient has a heart rate of 116 bpm, a respiratory rate of 16 breaths per minute, a systolic blood pressure of 150 mmHg, no urine output, a body temperature of 39 degrees Celsius, and is unresponsive, the score control 4614 would display an overall MEWS of 11 (2+1+0+3+2+3). In general, a patient's MEWS may be based on data derived from four physiological readings (e.g., systolic blood pressure, heart rate, respiratory rate, body temperature) and one observation (level of consciousness).

In response to receiving input selecting the rapid response control 4616, the event log application transmits a notification, via one or more channels, to a rapid response team to indicate the need for emergency care. The one or more channels can include e-mail, text messaging, instant messaging apps, hospital notification systems, intercoms, and the like. The notification can include patient information and/or a location of the mobile computing device (as derived from various technologies, such as global positioning system, local area network connections, cellular network connections, etc.). In some examples, the event log application is configured to monitor the MEWS listed in the score control 4614 and to automatically transmit a notification, via the one or more channels, to the rapid response team where the MEWS transgresses a threshold value.

In some examples, the event log application is configured to set default values accessible via one or more of the controls 4602-4612 to a measurement received by the event log application via another screen or source. For instance, where the blood pressure, heart rate, temperature, and/or respiration rate where entered via the vitals control 920 within a configurable time range from the current time, the event log application sets the default values of those parameters to the measurement entered via the vitals control 920.

Figure 47:
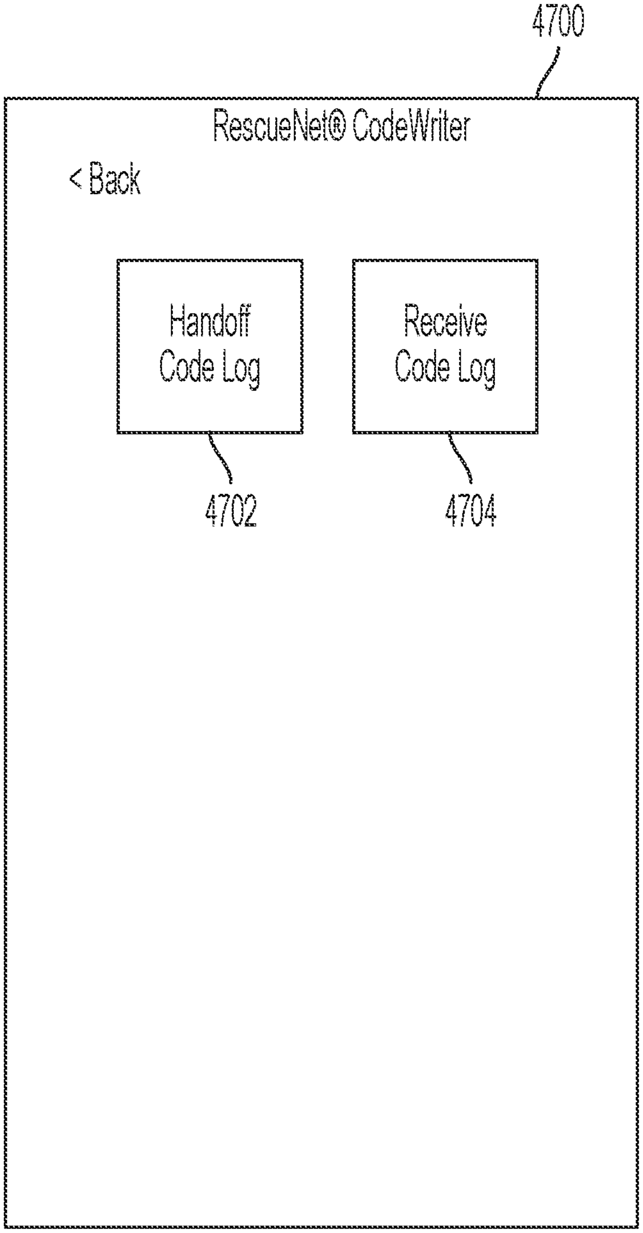
FIG. 47 is a view of a handoff screen provided by an event log application in accordance with at least one example disclosed herein.

In certain examples, the event log application is configured to provide a handoff screen that enables a healthcare provider to transfer an open code from a first mobile computing device to a second mobile computing device. FIG. 47 illustrates a handoff screen 4700 in accordance with these examples. As shown, the handoff screen 4700 includes a handoff control 4702 and a receive control 4704.

In some examples, in response to receiving input selecting the handoff control 4702, a first instance of the event log application, which is running on the first mobile computing device, generates and displays a fiducial. The fiducial identifies the first mobile computing device and the open code to be transferred to a second instance of the event log application executing on the second mobile computing device. In response to receiving input selecting the receive control 4704, the second instance of the event log application uses a camera or other image acquisition device of the second mobile computing device to scan the fiducial. Upon recognition of the fiducial, the second mobile computing device establishes a proximal connection, as described above, with the first mobile computing device. The second instance of the event log application generates a request to transfer the open event log and transmits the request to the first instance of the event log application. In response the first instance of the event log application transmits a copy of the open event log to the second instance of the event log application. The second instance of the event log application receives the copy of the open event log and provides an event log screen (e.g., the event log screen 900) to the healthcare provider (e.g., the healthcare provider 112) to enable the healthcare provider to continue documenting the code within the open event log.

Example Mobile Computing and Medical Devices

Figure 48:
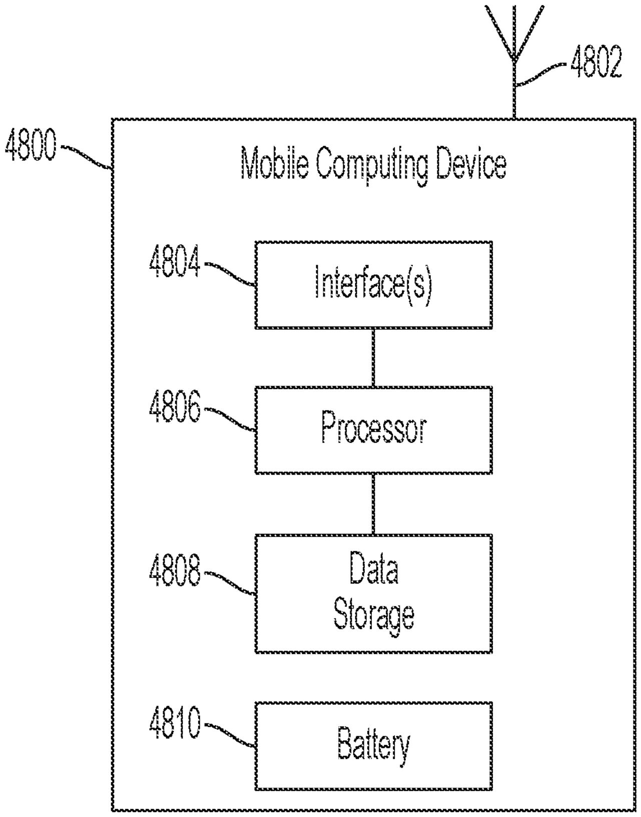
FIG. 48 is a schematic diagram illustrating a mobile computing device in accordance with at least one example disclosed herein.

FIG. 48 illustrates one examples of a mobile computing device 4800 that may be used to implement the event log application. In various examples, the mobile computing device 4800 is implemented using any of a variety of programmable devices (e.g., a device with data storage and at least one processor in data communication with the data storage). In some examples, the mobile computing device 4800 includes a plurality of interfaces 4804, one or more processors 4806, and a data storage device 4808 coupled to one another via a communication mechanism, such as a bus. In these examples, the mobile computing device 4800 also includes a battery 4810 to power the device and may include one or more antennas 4802. The data storage device 4808 can include a non-transitory data storage medium to store an operating system and one or more software applications or programs. These programs can include instructions executable by the one or more processors to implement the features disclosed herein and the methods that they execute. The plurality of interfaces in the mobile computing device 4800 include a user interface, a network interface configured to communicate with a network (e.g., the network 110), and/or a medical device interface configured to exchange information with a medical device (e.g., the medical device 104). For instance, the plurality of interfaces 4804 may include a touchscreen, a camera, an NFC tag, and/or an RFID tag.

Particular examples of the mobile computing device 4800 include medical devices, wearable devices, smart phones, tablet computers, and laptop computers. Wearable devices that may serve as the mobile computing device 4800 include various garments with integrated technologies, watches, anklets, necklaces, belt buckles, and glasses.

In examples where the mobile computing device 4800 is implemented via a smart phone, a dedicated software application (i.e., the event log application) may be downloaded to the smart phone to facilitate the interactions described herein. For instance, the event log application may be written for an Android, iOS, Windows, or other operating system of the smart phone.

Figure 49:
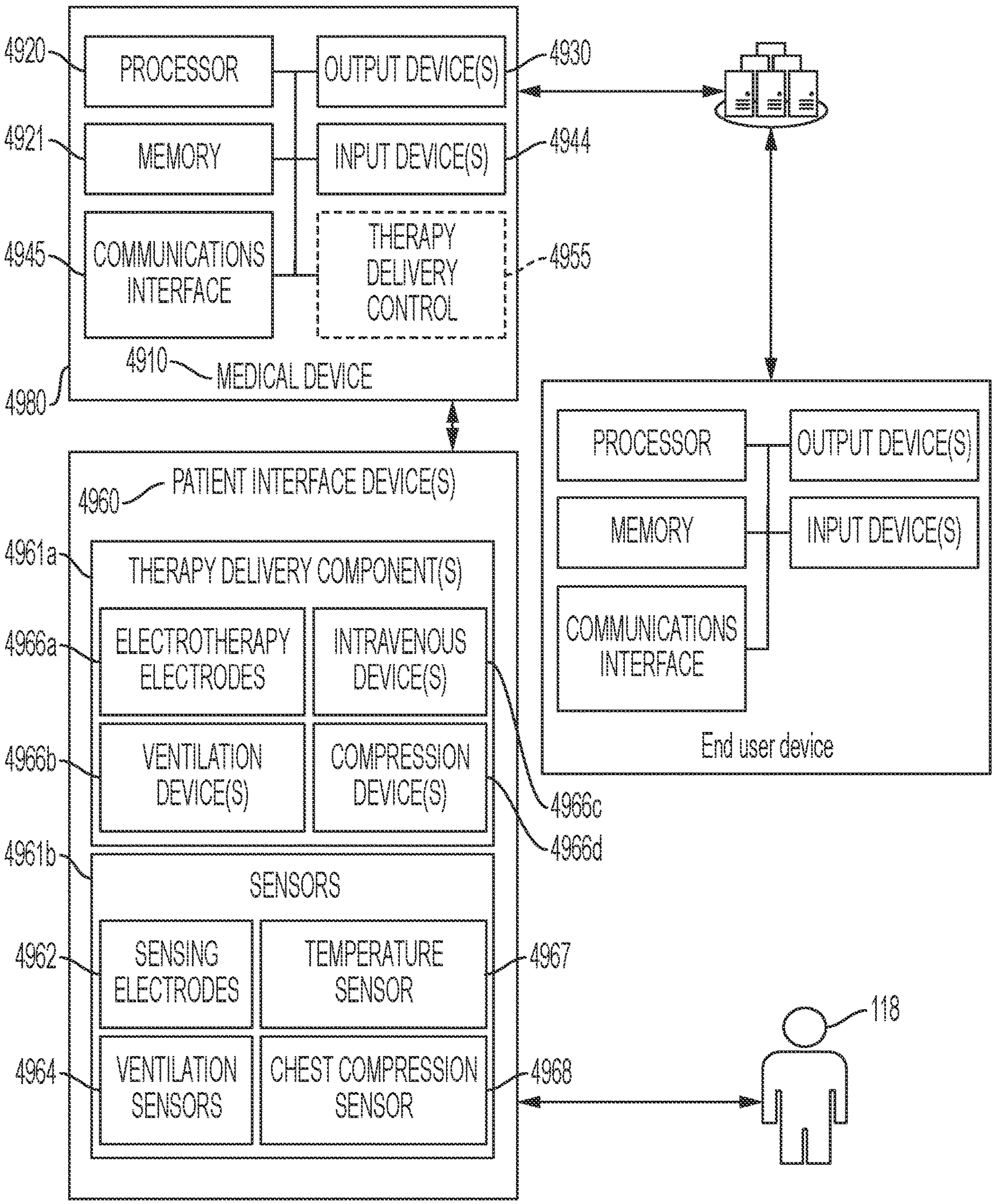
FIG. 49 is a schematic diagram illustrating a medical device in accordance with at least one example disclosed herein.

Referring to FIG. 49, examples of components of a medical device 4910 and are shown schematically. The medical device 4910 may include a processor 4920, a memory 4921, one or more output devices 4930, one or more user input devices 4944, and a communications interface 4945. The communications interface 4945 may include any of a variety of transmitters and/or receivers. For instance, in some examples, the communications interface 4945 includes one or more of an NFC tag, an RFID tag, a barcode and a QR code.

In various implementations, the medical device 4910 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 4910 may be an integrated therapy delivery/monitoring device within a single housing 4980. The single housing 4980 may surround, at least in part, the therapy delivery components and the monitoring components.

The patient interface device(s) 4960 may include one or more therapy delivery component(s) 4961*a* and/or one or more sensor device(s) 4961*b*. The medical device 4910 may be configured to couple to the one or more therapy delivery component(s) 4961*a*. In combination, the medical device 4910 and the one or more therapy delivery components may provide therapeutic treatment to the patient 118. In an implementation, the medical device 4910 may include or incorporate the therapy delivery component(s) 4961*a*. The therapy delivery component(s) 4961*a* are configured to deliver therapy to the patient and may be configured to couple to the patient. For example, the therapy delivery component(s) 4961*a* may include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 4910 may include the one or more therapy delivery component(s) 4961*a* and/or may be configured to couple to the one or more therapy delivery component(s) 4961*a* in order to provide medical therapy to the patient. The therapy delivery component(s) 4961*a* may be configured to couple to the patient 118. For example, a healthcare provider (e.g., the healthcare provider 114) may attach the electrodes to a patient 118 and the medical device 4910 (e.g., a defibrillator or defibrillator/patient monitor) may provide electrotherapy to the patient via the defibrillation electrodes. These examples are not limiting of the disclosure as other types of medical devices, therapy delivery components, sensors, and therapy are within the scope of the disclosure.

The first medical device 4910 may be, for example, a therapeutic medical device capable of delivering a medical therapy. For example, the medical therapy may be electrical therapy (e.g. defibrillation, cardiac pacing, synchronized cardioversion, diaphragmatic or phrenic nerve stimulation) and the first medical device 4910 may be a defibrillator, a defibrillator/monitor and/or another medical device configured to provide electrotherapy. As another example, the medical therapy may be chest compression therapy for treatment of cardiac arrest and the first medical device 4910 may be a mechanical chest compression device such as a belt-based chest compression device or a piston-based chest compression device. As other examples, the medical therapy may be ventilation therapy, therapeutic cooling or other temperature management, invasive hemodynamic support therapy (e.g. Extracorporeal Membrane Oxygenation (ECMO)), etc. and the medical device 4910 may be a device configured to provide a respective therapy. In an implementation, the medical device 4910 may be a combination of one or more of these examples. The therapeutic medical device may include patient monitoring capabilities via one or more sensors. These types of medical therapy and devices are examples only and not limiting of the disclosure.

The medical device 4910 may include, incorporate, and/or be configured to couple to the one or more sensor(s) 4961*b* which may be configured to couple to the patient 118. The sensor(s) 4961*b* are configured to provide signals indicative of sensor data (e.g., first sensor data) to the medical device 4910. The sensor(s) 4961*b* may be configured to couple to the patient. For example, the sensor(s) 4961*b* may include cardiac sensing electrodes, a chest compression sensor, and/or ventilation sensors. The one or more sensors 4961*b* may generate signals indicative of physiological parameters of the patient 118. For example, the physiological parameters may include one or more of at least one vital sign, an ECG, blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. Additionally or alternatively, the one or more sensors 4961*b* may generate signals indicative of chest compression parameters, ventilation parameters, drug delivery parameters, fluid delivery parameters, etc.

In addition to delivering therapy to the patient, the therapy delivery component(s) 4961*a* may include, be coupled to, and/or function as sensors and provide signals indicative of sensor data (e.g., second sensor data) to the medical device 4910. For example, the defibrillation electrodes may be configured as cardiac sensing electrodes as well as electrotherapy delivery devices and may provide signals indicative of transthoracic impedance, electrocardiogram (ECG), heart rate and/or other physiological parameters. As another example, a therapeutic cooling device may be an intravenous cooling device. Such a cooling device may include an intravenous (IV) device as a therapy delivery component configured to deliver cooling therapy and sense the patient's temperature. For example, the IV device may be a catheter that includes saline balloons configured to adjust the patient's temperature via circulation of temperature controlled saline solution. In addition, the catheter may include a temperature probe configured to sense the patient's temperature. As a further example, an IV device may provide therapy via drug delivery and/or fluid management. The IV device may also monitor and/or enabling monitoring of a patient via blood sampling and/or venous pressure monitoring (e.g., central venous pressure (CVP) monitoring).

The medical device 4910 may be configured to receive the sensor signals (e.g., from the therapy delivery component(s) 4961*a* and/or the sensor(s) 4961*b*) and to process the sensor signals to determine and collect the patient data. The patient data may include patient data which may characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data may characterize the delivery of therapy (e.g., chest compression data such as compression depth, compression rate, ventilation tidal volume, ventilation rate, etc.) and/or the patient data may characterize a status and/or condition of the medical equipment used to treat the patient (e.g., device data such as shock time, shock duration, attachment of electrodes, power-on, etc.).

The components of 4920, 4921, 4930, 4944, 4945, and 4955 of the medical device 4910 are communicatively coupled (directly and/or indirectly) to each other for bi-directional communication.

Although shown as separate entities in FIG. 49, the one or more of the components of the device 4910 may be combined into one or more discrete components and/or may be part of the processor 4920. The processor 4920 and the memory 4921 may include and/or be coupled to associated circuitry in order to perform the functions described herein.

In an implementation, the devices 4910 may be a therapeutic medical device configured to deliver medical therapy to the patient 118. Thus, the device 4910 may optionally include the therapy delivery control module 4955. For example, the therapy delivery control module 4955 may be an electrotherapy delivery circuit that includes one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 4955 may be a compression device electro-mechanical controller configured to control a mechanical compression device. As a further example, the therapy delivery control module 4955 may be an electro-mechanical controller configured to control drug delivery, temperature management, ventilation, and/or other type of therapy delivery. Alternatively, some examples of the medical device 4910 may not be configured to deliver medical therapy to the patient 118 but may be configured to provide patient monitoring and/or diagnostic care.

The medical device 4910 (e.g., a first medical device) may incorporate and/or be configured to couple to one or more patient interface device(s) 4960. The patient interface device (s) 4960 may include one or more therapy delivery component(s) 4961*a* and one or more sensor(s) 4961*b*. The one or more therapy delivery component(s) 4961*a* and the one or more sensor(s) 4961*b* sensor may provide one or more signals to the medical device 4910 via wired and/or wireless connection (s).

The one or more therapy delivery components 4961*a* may include electrotherapy electrodes (e.g., the electrotherapy electrodes 4966*a*), ventilation device(s) (e.g., the ventilation devices 4966*b*), intravenous device(s) (e.g., the intravenous devices 4966*c*), compression device(s) (e.g., the compression devices 4966*d*), etc. For example, the electrotherapy electrodes may include defibrillation electrodes, pacing electrodes, and/or combinations thereof. The ventilation devices may include a tube, a mask, an abdominal and/or chest compressor (e.g., a belt, a cuirass, etc.), etc. and combinations thereof. The intravenous devices may include drug delivery devices, fluid delivery devices, and combinations thereof. The compression devices may include mechanical compression devices such as abdominal compressors, chest compressors, belts, pistons, and combinations thereof. In various implementation, the therapy delivery component(s) 4961*a* may be configured to provide sensor data and/or be coupled to and/or incorporate sensors. For example, the electrotherapy electrodes may provide sensor data such as transthoracic impedance, ECG, heart rate, etc. Further the electrotherapy electrodes may include and or be coupled to a chest compression sensor. As another example, the ventilation devices may be coupled to and/or incorporate flow sensors, gas species sensors (e.g., oxygen sensor, carbon dioxide sensor, etc.), etc. As a further example, the intravenous devices may be coupled to and/or incorporate temperature sensors, flow sensors, blood pressure sensors, etc. As yet another example, the compression devices may be coupled to and/or incorporate chest compression sensors, patient position sensors, etc. The therapy delivery control module 4955 may be configured to couple to and control the therapy delivery component(s) 4961*a*.

In various implementations, the sensor(s) 4961*b* may include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos may be two-dimensional or three-dimensional.

The sensor(s) 4961*b* may include sensing electrodes (e.g., the sensing electrodes 4962), ventilation sensors (e.g., the ventilation sensors 4964), temperature sensors (e.g., the temperature sensor 4967), chest compression sensors (e.g., the chest compression sensor 4968), etc. For example, the sensing electrodes may include cardiac sensing electrodes. The cardiac sensing electrodes may be conductive and/or capacitive electrodes configured to measure changes in a patient's electrophysiology, for example to measure the patient's ECG information. In an implementation, the sensing electrodes may be configured to measure the transthoracic impedance and/or a heart rate of the patient 118. The ventilation sensors may include spirometry sensors, flow sensors, pressure sensors, oxygen and/or carbon dioxide sensors such as, for example, one or more of pulse oximetry sensors, oxygenation sensors (e.g., muscle oxygenation/pH), 02 gas sensors and capnography sensors, and combinations thereof. The ventilation sensor may provide signals indicative of ventilation data including air flow data, volume data, inspiratory flow, expiratory flow, etc. The temperature sensors may include an infrared thermometer, a contact thermometer, a remote thermometer, a liquid crystal thermometer, a thermocouple, a thermistor, etc. and may measure patient temperature internally and/or externally. The chest compression sensor may include one or more motion sensors including, for example, one or more accelerometers, one or more force sensors, one or more magnetic sensors, one or more velocity sensors, one or more displacement sensors, etc. The chest compression sensor may be, for example, but not limited to, a compression puck, a smart-phone, a hand-held device, a wearable device, etc. The chest compression sensor may be configured to detect chest motion imparted by a rescuer and/or an automated chest compression device (e.g., a belt system, a piston system, etc.). The chest compression sensor may provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes may include or be configured to couple to the chest compression sensor.

Figure 50:
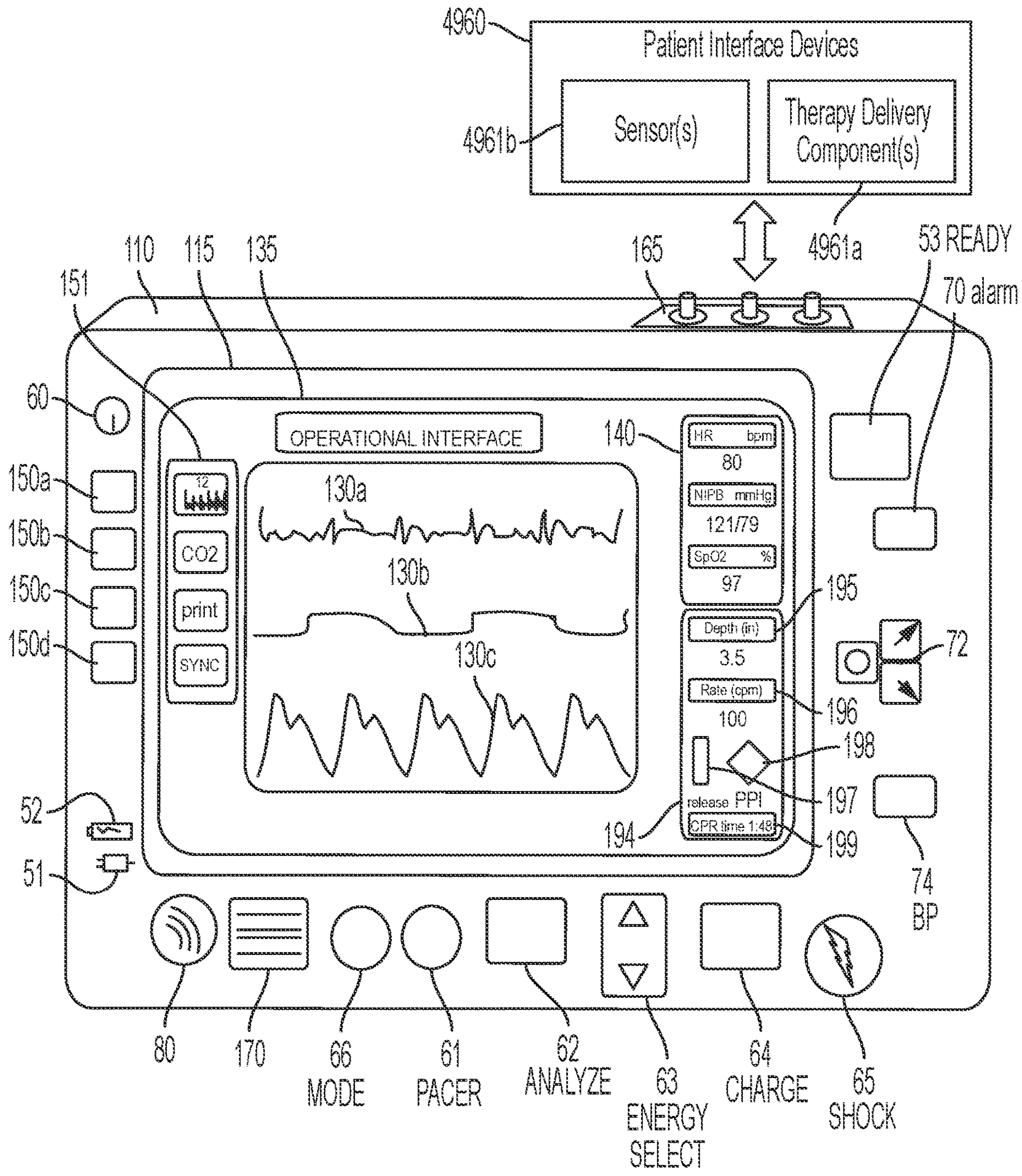
FIG. 50 is a schematic diagram illustrating another medical device in accordance with at least one example disclosed herein.

Referring to FIG. 50, an example of a medical device with an operational interface is shown. The medical device 4910 is shown in FIG. 50 as a patient monitor/defibrillator. This configuration of the medical device 4910 is an example only and not limiting of the disclosure. In various implementations, the medical device 4910 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 4910 may be an integrated therapy delivery/monitoring device that includes a single housing. The single housing may surround, at least in part, the therapy delivery components and the monitoring components. In an implementation, the medical device 4910 may be a modular therapy delivery/monitoring device.

The medical device 4910 may include one or more output or input/output devices, for example, a display screen 115. A processor of the medical device 4910 may control the display screen 115 to selectively display the operational interface 135. The operational interface 135 as shown in FIG. 50 is an example only and elements may be rearranged, combined, altered, or deleted. As discussed in further detail below, selective display refers to the ability of the processor to select amongst various available display modes which may include an operational interface only display mode.

The operational interface 135 may provide patient data received by the medical device 4910 from the patient interface device(s) 4960 (e.g., the therapy delivery component(s) 4961*a* and/or from the sensor(s) 4961*b*). For example, the medical device 4910 may be configured to couple to the patient interface device(s) 4960 via the one or more connection ports 165. The operational interface 135 may provide the patient data in real-time as the signals are received and processed by the processor 4920 of the medical device 4910.

The therapy delivery component(s) 4961*a* are configured to deliver therapy to the patient and may be configured to couple to the patient. For example, the therapy delivery component(s) 4961*a* may include one or more of electrotherapy electrodes including defibrillation electrodes and/or pacing electrodes, chest compression devices, ventilation devices, drug delivery devices, etc. In addition to delivering therapy to the patient, the therapy delivery component(s) 4961*a* may include, be coupled to, and/or function as sensors and provide signals indicative of sensor data (e.g., first sensor data) to the medical device 4910. For example, the therapy delivery component(s) 4961*a* may be defibrillation and/or pacing electrodes and may provide signals indicative of transthoracic impedance, electrocardiogram (ECG), heart rate and/or other physiological parameters.

The sensor(s) 4961*b* are configured to provide signals indicative of sensor data (e.g., second sensor data) to the medical device 4910. The sensor(s) 4961*b* may be configured to couple to the patient. For example, the sensor(s) 4961*b* may include cardiac sensing electrodes, a chest compression sensor, and/or ventilation sensors.

The medical device 4910 may be configured to receive the sensor signals (e.g., from the therapy delivery component(s) 4961*a* and/or the sensor(s) 4961*b*) indicative of patient data for the patient and configured to process the sensor signals to determine and collect the patient data. The patient data may include patient data which may characterize a status and/or condition of the patient (e.g., physiological data such as ECG, heart rate, pulse oximetry, non-invasive hemoglobin parameters, capnography, oxygen and CO2 concentrations in the airway, invasive and non-invasive blood pressures, tissue pH, tissue oxygenation, near infra-red spectroscopy, etc.). Additionally or alternatively, the patient data may characterize the delivery of therapy (e.g., chest compression data such as compression depth, compression rate, ventilation data such as ventilation tidal volume, ventilation rate, etc.) and/or the patient data may characterize a status and/or condition of the medical equipment used to treat the patient (e.g., device data such as shock time, shock duration, attachment of electrodes, power-on, etc.).

In addition to the display screen 115, the medical device 4910 may include one or more other output devices such as, for example, a speaker 170. The processor 4920 may be configured to control the speaker 170 to provide audible instructions, a metronome (e.g., a chest compression metronome), feedback, and/or physiological information for a user of the medical device 4910. The medical device 4910 may further include device status indicators and/or device operation controls. For example, device status indicators may include a power-on indicator 51, a battery charge indicator 52, and/or a device ready indicator 53. The device operation controls may include a power-on control 60, a pacer mode control 61, a heart rhythm analyze control 62, a defibrillation energy selection control 63, a charge control 64, a shock delivery control 65, an alarm control 70, one or more display navigation controls 72, and a sensor control 74. Activation of the sensor control 74 may cause an associated patient data sensor to capture patient data and provide the data to the medical device 4910. The display screen 115 may provide the captured patient data. For example, activation of the sensor control 74 may cause a blood pressure sensor to measure the patient's blood pressure and may cause the operational interface 135 to display the measured blood pressure in response to activation of the sensor control 74. The medical device 4910 may include one or more soft-keys 150*a*, 150*b*, 150*c*, 150*d*, one or more soft-key labels 151, and/or an NFC tag 80. The NFC tag 80 may enable the medical device 4910 to communicatively couple with another device, such as the mobile computing device 102.

The invention claimed is:

1. A system for providing documentation of emergency medical events related to treatment of a patient, the system comprising:

a defibrillator medical device having one or more cardiac sensing electrodes, one or more electrotherapy electrodes configured to deliver a therapy to the patient, at least one first processor, and a first memory, the at least one first processor and the first memory configured to:

obtain, repeatedly over time during the treatment of the patient, physiological information from the patient via the one or more cardiac sensing electrodes, obtain, at least once during the treatment of the patient, signals from the one or more electrotherapy electrodes regarding therapy delivery, automatically generate, responsive to obtaining the physiological information, one or more log entries of a first plurality of time-stamped log entries that mark events that occur during the treatment of the patient with the defibrillator medical device, and automatically generate at least one log entry of the first plurality of time-stamped log entries that mark at least one metric regarding the therapy delivered by the defibrillator medical device;

a mobile computing device having a user interface, at least one sensor, at least one second processor, and a second memory, the at least one second processor and the second memory configured to:

repeatedly over time during the treatment of the patient, (i) receive a plurality of one or more inputs entered by a user of the mobile computing device via the user interface, and (ii) responsive to receiving the one or more inputs, store, to the second memory by an event log application executing on the mobile computing device, one or more second log entries of a second plurality of time-stamped log entries, wherein the second plurality of time-stamped log entries mark further events that occur during the treatment of the patient, acquire, via the at least one sensor, an identifier associated with the defibrillator medical device, establish a secure connection, enabled by the identifier, to access the first plurality of time-stamped log entries, and after establishing the secure connection, receive, in real time via the secure connection, the one or more respective first log entries; and a server configured to:

receive at least the first plurality of time-stamped log entries, generate an event log data structure having a respective identifier field associated with each of the first plurality of time-stamped log entries, and populate the respective identifier field associated with each of the first plurality of time-stamped log entries with a unique identifier of the defibrillator medical device;

wherein the event log application executing on the mobile computing device is further configured to:

receive the event log data structure generated by the server, present, during the treatment of the patient, a single consolidated event log view updated in real-time for review by the user via the user interface, the single consolidated event log view comprising a plurality of events including:

a first plurality of events associated with at least a portion of the first plurality of time-stamped log entries, and a second plurality of events associated with at least a portion of the second plurality of time-stamped log entries, determine a source device associated with a given event of the plurality of events using the event log data structure generated by the server, and responsive to the determining, set a state of a control of the given event, wherein the state of the control is provided to maintain data integrity of the documentation of the emergency medical events, and setting the state of the control comprises:

in response to determining that the given event corresponds to one of the second plurality of time-stamped log entries, enabling edits via the single consolidated event log view in the user interface for the given event, and in response to determining that the given event is associated with an identifier field populated with the unique identifier of the defibrillator medical device, prevent edits via the single consolidated event log view in the user interface for the given event.

2. The system of claim 1, further comprising at least one additional computing device configured to:

establish a communicative connection with the defibrillator medical device to access the first plurality of time-stamped log entries; and establish a communicative connection with the mobile computing device to access the second plurality of time-stamped log entries.

3. The system of claim 2, wherein the at least one additional computing device has an additional user interface and is configured to present via the additional user interface a first set of events associated with the first plurality of time-stamped log entries and a second set of events associated with the second plurality of time-stamped log entries.

4. The system of claim 3, wherein the at least one additional computing device is configured to:

enable a first type of interaction via the additional user interface with the first plurality of events; and enable a second type of interaction via the additional user interface with the second plurality of events.

5. The system of claim 1, wherein the mobile computing device is configured to establish the secure connection based on a proximity-based detection, and the mobile computing device uses the at least one sensor for providing the proximity-based detection.

6. The system of claim 5, wherein the proximity-based detection comprises a detection based on a distance of less than 10 cm between the defibrillator medical device and the mobile computing device, and the at least one sensor comprises at least one of a camera, an NFC tag, and a RFID tag.

7. The system of claim 6, wherein:

the defibrillator medical device comprises a barcode or QR code; and the at least one sensor comprises the camera for capturing an image of the barcode or QR code to provide the proximity-based detection.

8. The system of claim 6, wherein the defibrillator medical device comprises an NFC tag corresponding to the NFC tag of the mobile computing device for providing the proximity-based detection.

9. The system of claim 6, wherein the defibrillator medical device comprises a RFID tag corresponding to the RFID tag of the mobile computing device for providing the proximity-based detection.

10. The system of claim 1, wherein the defibrillator medical device is configured to store patient identification information associated with the first plurality of time-stamped log entries.

11. The system of claim 10, wherein the mobile computing device is configured to access the patient identification information via the secure connection, wherein the secure connection is with the defibrillator medical device.

12. The system of claim 1, wherein the mobile computing device is configured to display on the user interface an option to select between an adult documentation mode and a pediatric documentation mode.

13. The system of claim 12, wherein:
- when the adult documentation mode is selected, the user interface provides adult-specific input options to include in the second plurality of events; and
- when the pediatric documentation mode is selected, the user interface provides pediatric-specific input options to include in the second plurality of events.

14. The system of claim 1, wherein:
- the mobile computing device is configured to display, in the single consolidated log view, an electrotherapy timer indicating a documented time elapsed since electrotherapy has been administered to the patient, wherein
  - the electrotherapy timer corresponds to an electrotherapy entry of one of the first plurality of time-stamped log entries or the second plurality of time-stamped log entries.

15. The system of claim 14, wherein the mobile computing device is configured to display, in the single consolidated log view, a documented indication of how many times electrotherapy has been administered to the patient, and the second plurality of time-stamped log entries comprises the electrotherapy entry indicating a documented time that electrotherapy has been administered to the patient.

16. The system of claim 1, wherein:
- the defibrillator medical device is configured to store a plurality of chest compression quality metrics; and
- the mobile computing device is configured to access the plurality of chest compression quality metrics via the secure connection, wherein
  - the secure connection is with the defibrillator medical device.

17. The system of claim 16, wherein the mobile computing device is configured to present via the user interface a summary of the chest compression quality metrics.

18. The system of claim 1, wherein:
- the mobile computing device is configured to display, in the single consolidated log view, a CPR timer indicating a documented time elapsed since chest compressions have been initiated, wherein the CPR timer corresponds to a CPR entry of one of the first plurality of time-stamped log entries or the second plurality of time-stamped log entries.

19. The system of claim 18, wherein the CPR timer provides a notification after 2 minutes have elapsed on the CPR timer.

20. The system of claim 18, wherein the mobile computing device is configured to display, in the single consolidated log view, a CPR idle timer indicating a documented time elapsed since chest compressions have paused.

21. The system of claim 20, wherein the CPR idle timer provides a notification after 10 seconds have elapsed on the CPR idle timer.

22. The system of claim 20, wherein the mobile computing device is configured to display, in the single consolidated log view, a documented indication of how many times chest compressions have been initiated and paused.

23. The system of claim 1, wherein the second plurality of time-stamped log entries comprises a CPR entry indicating a documented time that chest compressions have been initiated.

24. The system of claim 1, wherein the mobile computing device is configured to display, in the single consolidated log view, a drug timer indicating a documented time elapsed since a drug has been administered, wherein the drug timer corresponds to a drug entry of one of the first plurality of time-stamped log entries or the second plurality of time-stamped log entries.

25. The system of claim 24, wherein the drug timer provides a notification after 3 minutes have elapsed on the drug timer.

26. The system of claim 1, wherein the mobile computing device is configured to display, in the single consolidated log view, a documented indication of how many times a drug has been administered, wherein the documented indication of how many times the drug has been administered corresponds to one or more drug entries of the second plurality of time-stamped log entries.

27. The system of claim 1, wherein the second plurality of time-stamped log entries comprises a drug entry indicating a documented time that a drug has been administered.

28. The system of claim 1, the secure connection is established directly with the defibrillator medical device.

29. The system of claim 1, wherein secure connection enables receiving the first plurality of time-stamped log entries via at least one additional computing device.

30. The system of claim 1, wherein preventing editing for the given event comprises:
- receiving, via the user interface, input specifying a modification of one of the first plurality of time-stamped log entries; and
- ignoring the input.

31. The system of claim 1, wherein:
- enabling edits comprises providing an editing control in response to receiving a selection, via the user interface, of one of the second plurality of; and
- preventing editing comprises, in response to receiving a selection, via the user interface, of one of the first plurality of events, providing a graphical indication of the selection without providing the editing control.

32. The system of claim 1, wherein the at least one metric comprises one or more of a shock duration, a defibrillation energy delivered, a state of electrode attachment, a pacing duration, a pacing amplitude, or a pacing rate.

33. The system of claim 1, wherein each log entry of the at least one respective first log entry is generated responsive to obtaining the signals from the one or more electrotherapy electrodes.

* * * * *